(12) United States Patent
Zhang et al.

(10) Patent No.: US 10,883,962 B2
(45) Date of Patent: Jan. 5, 2021

(54) ELECTRICAL DOUBLE LAYER IN NANOPORES FOR DETECTION AND IDENTIFICATION OF MOLECULES AND SUBMOLECULAR UNITS

(71) Applicants: University of Kentucky Research Foundation, Lexington, KY (US); Clemson University Research Foundation, Clemson, SC (US)

(72) Inventors: Guigen Zhang, Lexington, KY (US); Samuel Bearden, Winston-Salem, NC (US)

(73) Assignees: University of Kentucky Research Foundation, Lexington, KY (US); Clemson University Research Foundation, Clemson, SC (US)

( * ) Notice: Subject to any disclaimer, the term of this patent is extended or adjusted under 35 U.S.C. 154(b) by 337 days.

(21) Appl. No.: 15/875,398

(22) Filed: Jan. 19, 2018

(65) Prior Publication Data
US 2018/0202969 A1    Jul. 19, 2018

Related U.S. Application Data

(60) Provisional application No. 62/448,166, filed on Jan. 19, 2017.

(51) Int. Cl.
| | | |
|---|---|---|
| *G01N 27/447* | (2006.01) | |
| *G01N 33/487* | (2006.01) | |
| *C12Q 1/6869* | (2018.01) | |

(52) U.S. Cl.
CPC ..... *G01N 27/44756* (2013.01); *C12Q 1/6869* (2013.01); *G01N 33/48721* (2013.01)

(58) Field of Classification Search
CPC ......... G01N 27/44791; G01N 27/4473; G01N 33/48721; G01N 33/48728; Y10S 977/852; Y10S 977/733; Y10S 977/72; Y10S 977/721; C12Q 1/6813; C12Q 1/6876; C12Q 1/6825; C12Q 1/6869; C12Q 1/68; C12Q 2563/116; C12Q 2565/631
See application file for complete search history.

(56) References Cited

U.S. PATENT DOCUMENTS 8,860,438 B2    10/2014   Zhang

OTHER PUBLICATIONS

Bearden, S.; McClure, E.; Zhang, G. Detecting and Identifying Small Molecules in a Nanopore Flux Capacitor. Nanotechnology (2016) 27, pp. 1-11.
Bearden, S., Manipulation of the Electrical Double Layer for Control and Sensing in a Solid State Nanopore, dissertation, Clemson University, Aug. 2015 (Embargoed until Aug. 2017), 261 pages.
Bearden S, Simpanen E and Zhang G, Active current gating in electrically biased conical nanopores; Nanotechnology, 2015, 26, pp. 1-11.
Bearden, S.; Zhang, G. Actively Controlled Ionic Current Gating in Nanopores. COMSOL Cont 2013, 3-7.
(Continued)

*Primary Examiner* — Gurpreet Kaur
(74) *Attorney, Agent, or Firm* — Stites & Harbison PLLC; Mandy Wilson Decker; Summer E. Young

(57) ABSTRACT

Systems for detecting analytes in electrical double layer nanopore devices and methods of use are provided.

14 Claims, 18 Drawing Sheets

(56) References Cited

OTHER PUBLICATIONS

Yang X and Zhang G; The effect of an electrical double layer on the voltammetric performance of nanoscale interdigitated electrodes: a simulation study; Nanotechnology (2008) 19; pp. 1-8.

Yang X and Zhang G; Simulating the structure and effect of the electrical double layer at nanometre electrodes Nanotechnology 18 (2007); pp. 1-9.

Zhang G; Simulating the electrical double layer capacitance COMSOL Conf. (2010) (Boston, MA).

Bearden, S.; Zhang, G. A Solid-State Nanopore as Biosensor. In Computational Bioengineering; Zhang, G., Ed.; CRC Press, 2015; pp. 355-376.

Timp, W.; Comer, J.; Aksimentiev, A. DNA Base-Calling from a Nanopore Using a Viterbi Algorithm. Biophys. J. 2012, 102, L37-9.

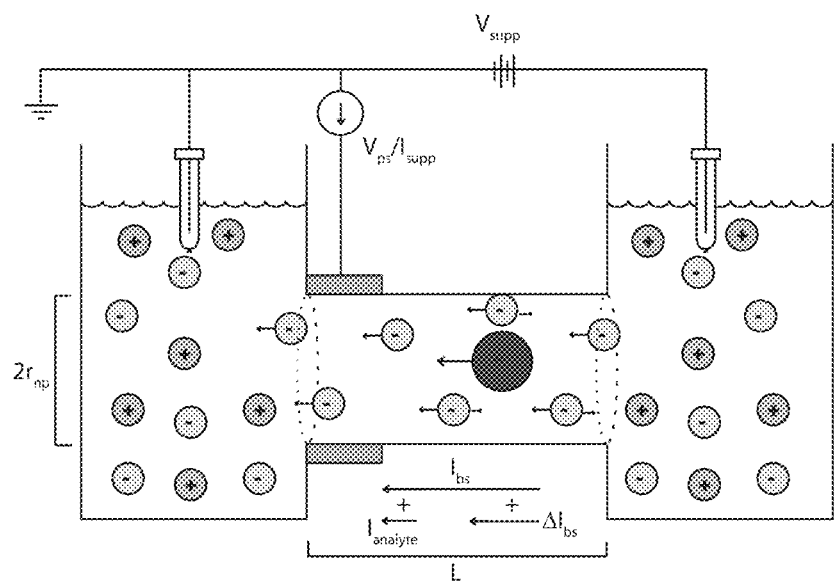
FIG. 7B
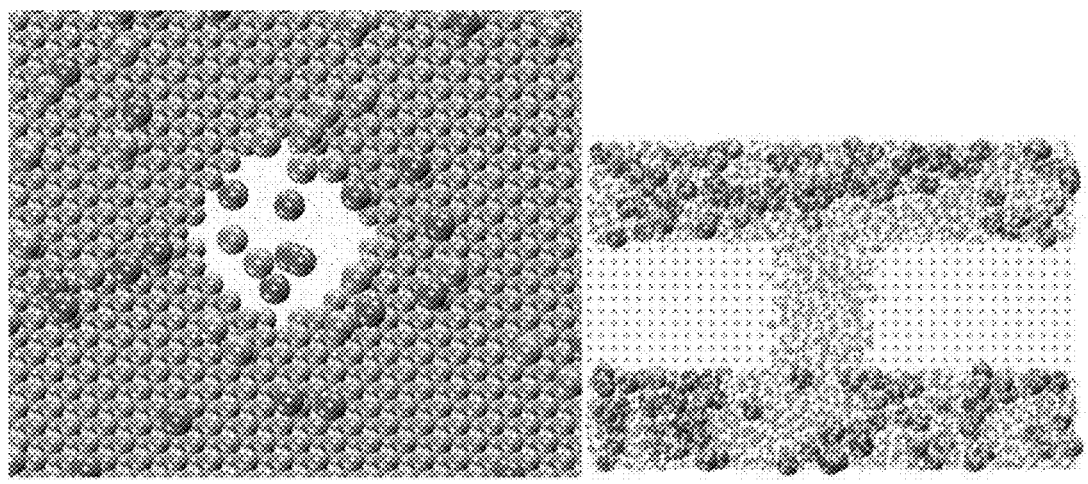
FIG. 7C  FIG. 7D

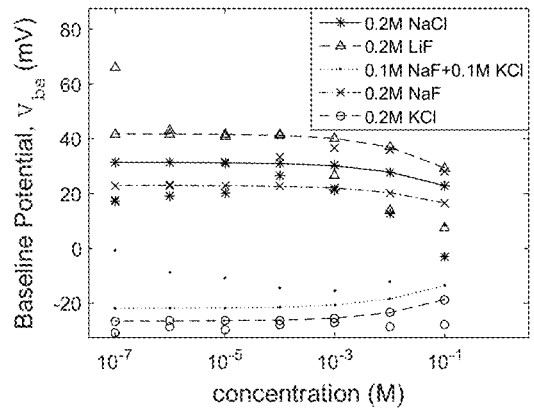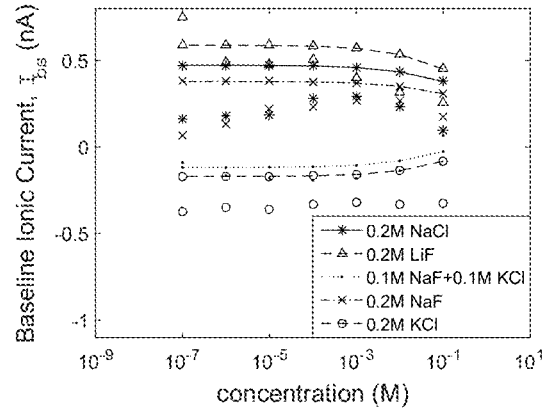
FIG. 8A  FIG. 8B
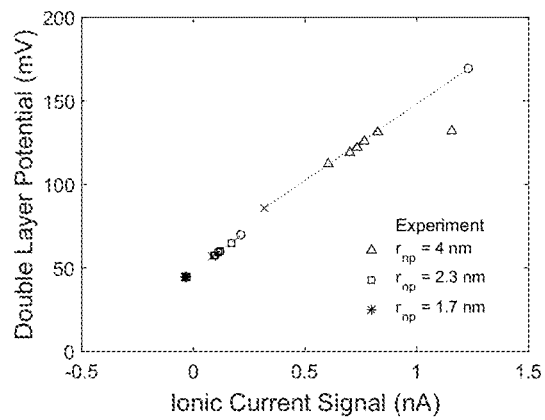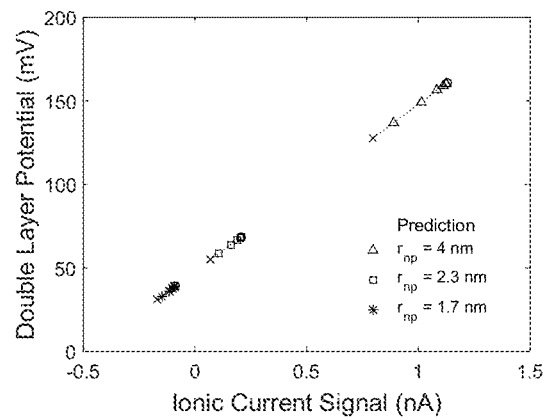
FIG. 8C  FIG. 8D
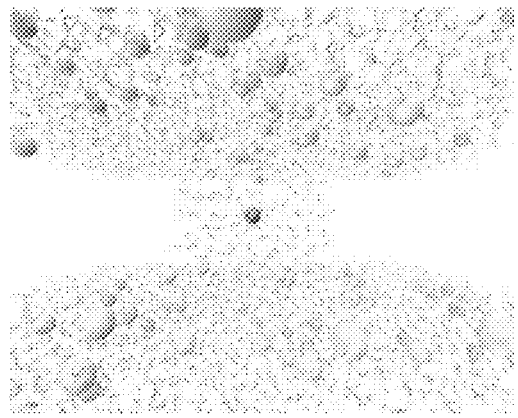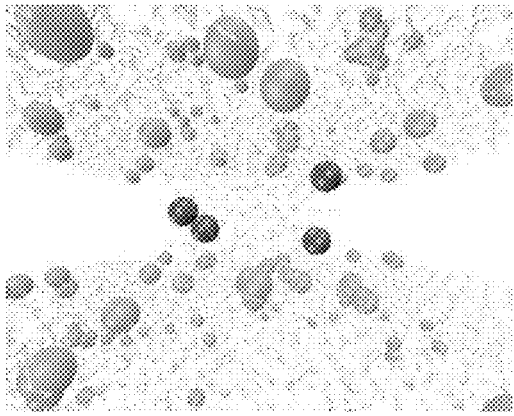
FIG. 9A  FIG. 9B

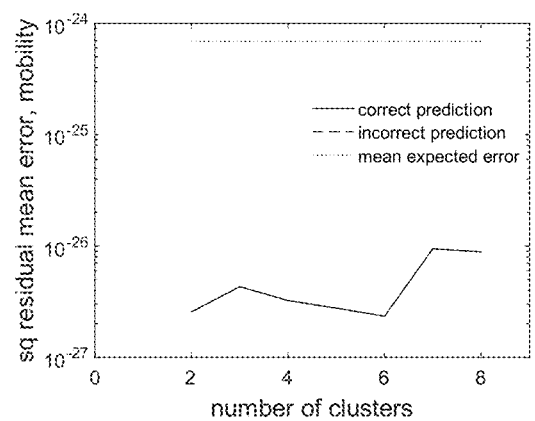
FIG. 19C
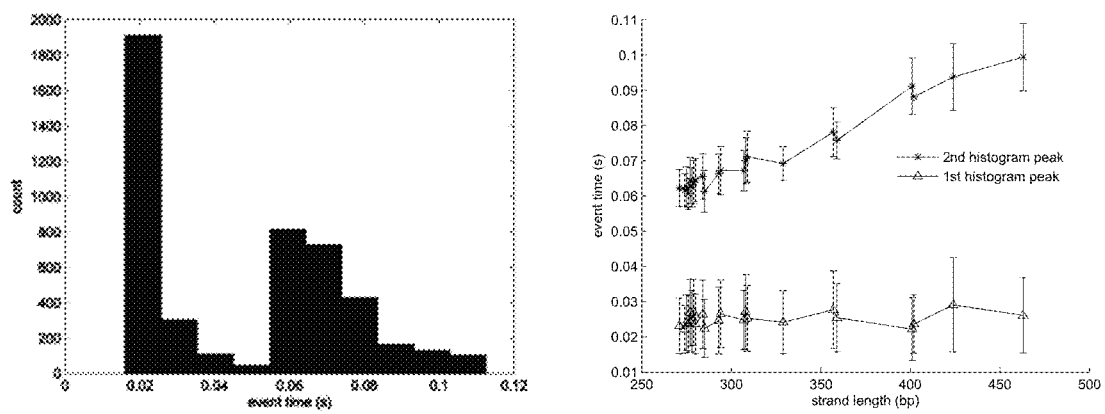
FIG. 20A          FIG. 20B
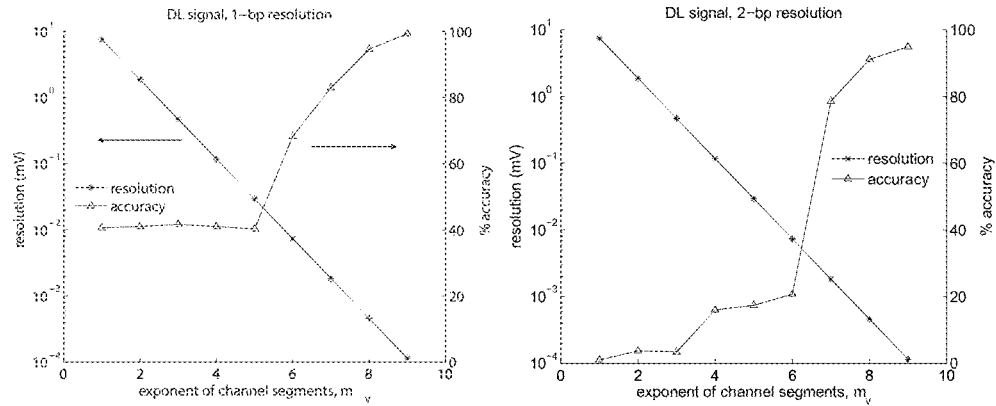
FIG. 21A          FIG. 21B

ELECTRICAL DOUBLE LAYER IN NANOPORES FOR DETECTION AND IDENTIFICATION OF MOLECULES AND SUBMOLECULAR UNITS

RELATED APPLICATIONS

This application claims priority from U.S. Provisional Patent Application No. 62/448,166, filed Jan. 19, 2017, the entire disclosure of which is incorporated herein by this reference.

TECHNICAL FIELD

The presently-disclosed subject matter relates to a method of molecular detection utilizing a metallic-semiconductor nanopore. In particular, embodiments of the presently-disclosed subject matter relate to a system and methods for detecting and/or measuring analytes in a system.

INTRODUCTION

Nanopore devices for detecting and identifying small molecules and sub-molecular units have been developed with a range of mechanisms and applications. The most commonly cited use for nanopore sensors is in nucleic acid sequencing. Because of the very small (nanoscale) sampling volume of this type of sensor, it is possible to temporally and spatially isolate individual molecular and sub-molecular analytes. One example is shown in U.S. Pat. No. 8,860,438 (incorporated by reference). However, a reliable method of transducing the translocating analyte into signals with physical and chemical relevance is needed that relies upon more than just EDL capacitance with nanopores for accuracy.

Nanopores used for sensing may be biological in origin (for example, based on α-hemolysin proteins) or solid-state devices. Biological nanopores have so far fallen short of their expected performance. They are difficult to customize, and have limited possibilities for signal transduction. Alternatively, solid-state nanopores are highly customizable and in many cases are compatible with standard thin-film fabrication techniques. Nanopores developed for molecular sensing applications typically rely on measurements of the ionic through-current as a signal transduction mechanism, where the signal arises due to occlusion of the nanopore by the analyte. Transverse detection methods have been developed in order to overcome the high noise level of the ionic current signal, however, these methods typically result in an inherent sensitivity to the orientation of the analyte within the nanopore, which limits the usefulness of any derived signal.

Thus far in the study of nanopores, the electrical double layer (EDL) has primarily been considered with regards to transport properties, rather than any sensing applications. In the small space within the nanopore, the EDL occupies the entire volume, resulting in regions of charge selectivity which can cause enhanced ionic current and current gating effects. It has been shown that many of the transport properties of nanopores may be explained in terms of the structure of the EDL within the lumen. In any sufficiently small nanopore, the analyte must move through the EDL during translocation.

Nanopores have long been considered as the future of DNA sequencers, where DNA is passed through a nanopore and each nucleotide base is read as it translocates. Many varieties of nanopores with variations in structure, materials, and signal transduction mechanisms have been introduced since the idea was first published in 1995. The accuracy of the sequences produced by these methods does not yet compete with state-of-the-art next generation sequencers. The range of transduction mechanisms that have been developed with the goal of producing a nanopore DNA sequencer include monitoring the ionic current through the nanopore (the blockade signal), functionalized sites within the nanopore, tunneling electrodes across the nanopore, and transverse conductance measurements in a molecularly thin material. However, in all cases there have been some limiting factors which preclude high accuracy basecalls, such as high noise levels, non-constant translocation factors, limited nucleotide resolution, or proneness to analyte orientation in the nanopore.

In the typical case, nanopore sensors rely on measurement of the ionic current through the nanopore, which arises due to the transport of charged species. Changes in the ionic current occur due to physical occlusion of the nanopore and the translocation of charged analytes. In DNA sequencing applications, a chain of negatively charged nucleotides move through the nanopore, but the translocation rate may vary depending how much of the strand has passed through the nanopore. This limitation means that the ionic current signal from a given nucleotide may be sensitive to both the particular nucleotide properties and the location of the nucleotide on the strand, as well as the physical and electrical conditions of the nanopore. Because of this sensitivity, along with high noise levels in the sub-molecular measurement, DNA sequencers relying on this method alone typically require additional systems to control translocation rate.

Nanopore devices are complex systems with a wide range of applications, from nanofluidic valves and actuators, to high-resolution molecular sensors. A complete analytical model would improve the ability to analyze these devices on the fly and to validate more complex models. In order to describe the underlying physical processes within these sorts of devices, many different models have been created primarily relying on computational methods due to the difficulty of fully parameterizing these systems. Computational modeling is most often done using finite element methods, molecular dynamics, or some combination of modeling modalities. Often there are too many unknown boundary conditions to empirically validate all aspects of a given model. While these complex models can provide interesting and relevant information about a nanopore system, the complexity can be a hurdle to wide application of the model or to adapting the model to different systems.

With the advent of commercial nanopore sequencers, other classes of analytes have sparked interest, such as small molecules, peptides, and RNA. Many signal transduction methods have been developed for nanopore sensors, including the ionic current (blockade) signal, tunneling electron signals, functionalization with recognition sites, as well as others.

An empirical model based on measurable parameters is needed to quantify the underlying physics in a general and useful way and to assist in the design and analysis of nanofluidic devices.

Therefore, it is an object of the present invention to provide for a reliable method of transducing the translocating analyte into signals with physical and chemical relevance. It is another object of the present invention to simultaneous collect ionic current and double layer potential signals to improve error rates.

SUMMARY

Provided herein are methods utilizing the double layer potential, ionic current, and mobility signals measured simultaneously from a single molecule, and an approach for multi-channel detection in which the sensing modalities may be used individually or in combination. In mixture analysis, all three signal-types may be considered, where increasing the number of signals per analyte detection will provide additional characterization of the analytes. In the case of DNA sequencing, where the nucleotide analytes are physically joined together in the DNA strand, mobility is not expected to be a strongly predictive signal mechanism and analysis is limited to the ionic current signal and double layer potential signal. The consideration of probability distributions in HMMs to link the input sequences and the observed signals in a probabilistic manner provides tolerance to the inherent noisiness of these measurements. Additional advantages of this multi-signal system with a solid-state nanopore are that the nanopore may be produced by nanoscale fabrication techniques with conventional solid-state materials, the device is reusable with a long operational life, and signal acquisition requires only minimal reagents consisting of an aqueous electrolyte solution with analytes.

In previous patent, U.S. Pat. No. 8,860,438, incorporated herein by reference, measurements utilizing an electrical double layer (EDL) capacitive device is provided that includes an insulating substrate defining a nanopore therethrough with a nanopore electrode exposed in a portion of the nanopore, and wherein the nanopore electrode defines a conductive ring surface exposed around an inner surface of the nanopore. However, this nanopore device is limited to measurements of electrical double layer (EDL) capacitance, whereas the presently disclosed subject matter measures the charging potential of the EDL capacitance. This distinction is important because, as disclosed herein, the EDL capacitance is not directly measured as in the prior device, and the charging potential (the double layer potential) measured is dependent on both the EDL capacitance and the charge accumulation in the nanopore. The measurement of multiple signals, i.e. the double layer potential, ionic current, and analyte mobility, individually or in any combination provides improved identification and evaluation of the properties of the molecule or analyte evaluated in the device.

Methods of utilizing the nanopore device are also provided. For example, in some embodiments, methods of using the double layer potential for DNA sequencing is provided. Moreover, methods of using multiple simultaneous signals (ionic current and double layer potential signals) for DNA sequencing are provided. Based on the disclosure herein, selection of high quality translocation signals by requiring a high degree of concurrency between ionic current and double layer potential signals can be achieved. Based on the nanopore device and the present disclosure, methods of detecting and identifying multiple analytes in a mixture are disclosed, including the steps of measuring double layer potential, ionic current, and/or mobility signals individually or in combination; grouping the signals by analyte by a clustering algorithm; identifying an analyte in the mixture by comparing the expected double layer potential signal of the analyte with the grouped double layer potential signals form a mixture. In some embodiments, accuracy is maximized by considering all three signal-types in combination. A particular advantage of the presently disclosed methods allows identification of analytes in mixtures without chemical tagging of the analytes prior to detection which would limit their sensitivity.

Disclosed herein are improved electrical double layer (EDL) nanopore devices including an insulating substrate defining a nanopore therethrough; a nanopore electrode exposed in a portion of the nanopore wherein the nanopore electrode defines a conductive ring surface exposed around an inner surface of the nanopore along its depth in a conductive ring; an electrolyte in contact with the nanopore electrode; a reference electrode in contact with the electrolyte; and a meter electrically coupled between the nanopore electrode and the reference electrode, wherein the meter is configured to measure the charging potential of the EDL capacitance, ionic current, analyte ability and combinations thereof and to correlate the measurements with one or more properties of the analyte and/or the identity of the analyte.

In some embodiments, the conductive ring has a thickness in a range of about 0.1 to 10 nm. In some embodiments, the ring electrode of the nanopore device is axisymmetric.

The nanopore diameter can vary according to the application of the nanopore device. In some embodiments, the nanopore diameter is between about 0.1 nm and 1000 nm.

A variety of analytes can be evaluated by the methods and devices disclosed herein, including polymers, polynucleotides and other chemical and biological analytes such as peptides, small molecules, toxins, and viruses. Further, depending on the analytes and other detection variables, the electrolyte can be, in some instances NaF, KCl, NaCl, LiF, or a mixture of NaF and KCl.

In some embodiments, the insulating substrate of the nanopore device includes a first and second insulating layer. In some instances, the nanopore electrode includes a conductive layer on the first insulating layer. In some instances, there is a second insulating layer on the conductive layer so that the conductive layer is between the first and second insulating layers. The nanopore can extend through the first and second insulating layers and through the conductive layer so that portions of the conductive layer are exposed in the nanopore between the first and second insulating layers.

The first and second insulating layers can include at least one insulating material selected from the group consisting of silicon dioxide, silicon nitride and polyxylylene polymers. The conductive layer can include at least one material selected from the group consisting of platinum, gold, titanium, copper, carbon, indium tin oxide and a conductive polymer.

Methods of determining physical properties such as the size and charge of analytes are provided including the steps of inducing an analyte to translocate through a nanopore of a nanopore device of the presently disclosed subject matter; measuring the signals comprising double layer potential, ionic current, mobility signals, or a combination thereof; and quantitatively determining the size and charge of the analyte by correlating the measured signals to an analytical model.

In some embodiments, the methods of detecting analytes includes an analytes provided in a mixture of analytes. One advantage of the presently disclosed methods is the ability to quantitatively identify analytes in such a mixture.

Methods of detecting and identifying a plurality of analytes in a mixture are provided including the steps of inducing each of the plurality of analytes to translocate through the nanopore of a nanopore device as disclosed herein; measuring the signals comprising double layer potential, ionic current, mobility signals, or a combination thereof of each analyte it translocates the nanopore; grouping the signals by a clustering algorithm executed by the meter; and comparing signals of the analyte with grouped signals from the mixture thereby identifying each of the plurality of analytes based on their signals.

Methods of quantitatively determining the physical properties—for example, the size and charge-of molecular analytes are also provided. In some embodiments the method includes detecting the nanopore signals; fitting the detected nanopore signals to an analytical model of the system, thereby providing quantitative measurements of the size and charge of the molecular analytes. This method offers more complete analyte characterization than any other nanopore method, and is believed to be the first method capable of determining analyte characteristics in a quantitative way.

DESCRIPTION OF THE DRAWINGS

Illustrative aspects of embodiments of the present invention will be described in detail with reference to the following figures wherein:

The following drawings, which are incorporated in and from a part of the specification, illustrate embodiments of the present invention and, together with the description, serve to explain the principles of the invention.

FIG. 7B Perturbed-state conditions during analyte translocation, for illustrative purposes drawing is not to scale. The signals associated with the molecular analyte (dark grey) are due to physical displacement and electrical interaction with the supporting electrolyte within the nanopore. The interactions result in a change to the number of ions within the nanopore (a change in charge density) and a change to the drift velocity of those ions (reverse velocity arrows in this diagram); FIG. 7C An MD model was created with a nanopore in an Au membrane; and FIG. 7D Supporting ions were scattered throughout the equilibrated waterbox taking care not to place any inside the nanopore at the initial condition;

FIG. 8A The baseline double layer potential is a function of concentration and supporting electrolyte. The predicted potentials for different supporting electrolytes have similar trend and magnitude to the measured potentials; FIG. 8B The baseline ionic current is related to the supporting electrolyte through the empirical relation (Equation 2) and the predicted baseline double layer potential (Equation 1). There is good agreement between predicted and experimental values; FIG. 8C The empirical relationship between the baseline ionic current and double layer potential (Equation 2) holds for nanopores with radii in the range of 1.7 nm to 4 nm and for concentrations from $10^{-7}$ M to 1 M in each nanopore. For each nanopore in this figure, the low concentration ($10^{-7}$M) is marked by an 'x' and the high concentration (1M) is marked with an 'o' to denoted the general trend of the concentration; and FIG. 8D The baseline potential and ionic current predicted from the activity of the solutions, the nanopore size, and the empirical relationships (Equations 1 and 2) closely matches experimental values.

FIG. 9A When NaF is introduced to an uncharged gold nanopore, the smaller $F^-$ ion quickly enters the nanopore first. $Na^+$ ions are shown in yellow and $F^-$ ions are shown in green vdW representation; water is shown in transparent CPK representation. For clarity the gold surface is not displayed, and the ions in the nanopore are shown in glossy vdW representation, whereas the ions outside the channel are shown in transparent vdW representation. FIG. 9B The negatively charged gold nanopore in NaF solution only attracts positive ions, overruling the 'size effect'.

FIG. 17D The normalized error is comparable across all signals. FIG. 17E The point-by-point analysis shows that the predicted clusters typically include more than 50% of the correct signal vectors. The fact that the error rate remains consistent (a-c) while the proportion of signal vectors correctly assigned varies suggests that most of the mis-assignment occurs in overlapping or bordering regions of different clusters. FIG. 17F Predicted characteristic signal distributions for a 4-analyte artificial mixture. FIG. 17G The actual characteristic signal distributions for the same 4-analyte artificial mixture.

FIG. 18D The normalized error is comparable across all signals.

FIG. 19A-19C includes charts of FIG. 19A charting Mean residual error between a target analyte centroid and the predicted cluster centroids in the double layer potential signal. FIG. 19B The mean residual error between target and predicted centroids in the ionic current signal are indicative of the presence of the target only for solutions containing more than 4 analytes. FIG. 19C The mean residual error between target and predicted centroids in the mobility signal are indicative of the presence of the target only for solutions containing more than 4 analytes, similar to the ionic current signal.

FIG. 20A The bi-modal distribution of translocation events observed in the double layer potential signal trace. Translocation events that occurred at the same time with similar duration in the ionic current and double layer potential were considered as meaningful sensor output. FIG. 20B The time duration associated with the second histogram peak is linearly related to strand length, indicating that events captured in the second peak are due to complete translocation of DNA samples. The time duration of the first histogram peak was not proportional to the length of the DNA, indicating that these events were not complete translocations.

FIG. 21A-21I detail the sequencing accuracy and output resolution of the sensor. This includes sequencing accuracy and output resolution for the double layer potential signal, including FIG. 21A with 1 nucleotide resolution, FIG. 21B showing 2 nucleotide resolution, and FIG. 21C showing 3 nucleotide resolution in the DNA evaluation set. In the evaluation data set, the 1 nucleotide resolution has the highest sequencing accuracy in the double layer potential signal. The sequencing accuracy and output resolution of the sensor for the ionic current signal is detailed with FIG. 21D showing 1 nucleotide resolution, FIG. 21E showing 2 nucleotide resolutions, and FIG. 21F showing 3 nucleotide resolution in the evaluation data set. The 2 nucleotide resolution has the highest sequencing accuracy in the ionic current signal. The effect of independently changing the size of the output spaces of the ionic current (triangles) and double layer potential (stars) on the dual channel (mesh) sequencing accuracy is detailed in FIG. 21G showing with 1 nucleotide resolution, FIG. 21H showing 2 nucleotide resolutions, and FIG. 21I showing 3 nucleotide resolution. The sequencing accuracy of the combined data channels tends to be better than either of the individual channels for low to moderate quantization of the individual channels. At high quantization levels of the double layer potential signal, the single channel sequencing accuracy is better than the dual channel sequencing accuracy. However, relatively high sequencing accuracy in the dual channels can be attained when both individual channels are at moderate quantization levels.

DESCRIPTION OF EXEMPLARY EMBODIMENTS

Figure 1A:
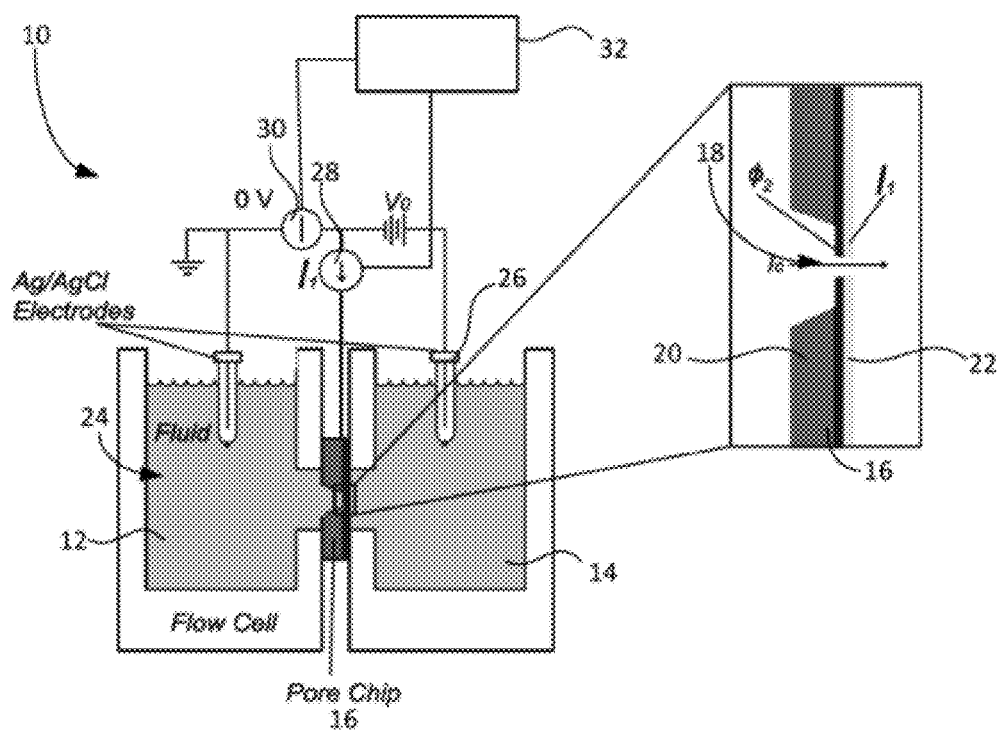
FIG. 1A. is an exemplary schematic of the nanopore system that includes includes a Si3N4/gold membrane with nanopore and a supporting solution. The solution contains the analyte of interest and supporting electrolyte which are transported through the nanopore. An electric field is generated across the nanopore by application of a voltage clamp, allowing the ionic current through the nanopore to be monitored. A constant electrical current is supplied to the gold layer of the nanopore.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding, and no unnecessary limitations are to be understood therefrom.

A unique double layer technique sensitive to the charging potential of the electrical double layer capacitance within a nanopore with a ring-electrode was developed. This double layer potential can be detected at the same time as the ionic current signal and the single-molecule mobility. Since the three signals considered in this technique (ionic current, double layer potential, and mobility) are obtained simultaneously from single-molecules, they may be considered in combination to improve the overall robustness of the sensor system. The nanopore sensor presents itself as a platform for physics-based molecular characterization and analysis of complex solutions is demonstrated.

In order to develop a general purpose, non-functionalized molecular sensor with a high level of reliability, machine learning techniques may be implemented for multi-signal characterization of single molecule targets. Supervised and unsupervised techniques are adapted to take advantage of the characteristics of specific types of analytes. For example, in order to identify characteristic signals from a mixture of small molecules, an unsupervised classification method such as hierarchical clustering is sufficient. When relating the observed signals to a limited molecular input such as individual nucleotides in DNA sequencing, a supervised method may be used. Machine learning techniques are particularly well suited for this type of task which depends on recognizing correlations in noisy, multi-dimensional data.

The purpose of analyzing solution is often to determine the presence of some particular analyte which may be a contaminant, toxin, biomarker or some other species of interest in a complex mixture like a blood or water sample. Clustering techniques offer a method of naively dividing datasets into subsets, such as to separate signals from several mixed analytes into the characteristic signals of each type of analyte. By selecting an appropriate clustering method with internal and external validation criteria, the characteristic signals from each type of analyte detected in a mixture may be identified and considered in analysis of a test solution. Targeted analyte detection can be accomplished in a non-functionalized way by identifying characteristic signals in a solution and comparing to a database or computing molecular properties.

Supervised machine learning techniques such as Hidden Markov models (HMMs) have been proposed for nanopore DNA sequencing. A HMM is a probabilistic model consisting of transitions between hidden states where each state produces some observable emission. In the case of nanopore DNA sequencing, the hidden states are short n-nucleotide segments of a DNA strand as they pass through the nanopore, where n is the nucleotide resolution of a given nanopore. The emissions are the observed ionic current and double layer potential signals that correlate with the translocating nucleotide segments. The HMM will link an emission to a state through a probability distribution, where the most probable sequence of states corresponding to a sequence of observed signals may be found by implementing a Viterbi algorithm over the HMM. Since the probability of transitioning between states (n-nucleotide segments) is accounted for in a HMM along with the emission probability, the sequence of the DNA can be reconstructed from observed signals with high reliability. Where the nucleotide resolution of a nanopore is greater than 1 (n>1), considering the state transition probability dramatically reduces the uncertainty of the predicted state since there will be overlap between the current and next state as the DNA strand progresses through the nanopore. For example, an n=3 nucleotide resolution nanopore could sample a segment such as 'ATC', which is likely to transition to 'GAT', 'CAT', 'AAT', or 'TAT', where the 'A' and 'T' nucleotides advance one position and only the trailing nucleotide is unknown. As a result, the number of likely following states is reduced from $4^3=64$ to $4^1=4$. The probability distribution linking DNA segments with signals and the probabilities for transitions between states in a nanopore sensor may be determined by training HMMs with measured ionic current and double layer potential signals from known DNA sequences. Once these probabilities are determined, the model may be used to predict the sequence of hidden states (which is the sequence of the DNA sample) from a sequence of observed signals.

A new system and method for detecting and identifying small molecular analytes in a nanopore has been developed, as described herein. The double layer potential signal is dependent on the change in Debye potential of the solution within the nanopore due to the valence charge and size of the analyte molecule. The magnitude of the double layer potential signal is insensitive to pH and influenced by the concentration of the supporting electrolyte. The ionic current signal is sensitive to pH, indicating that the overlapped double layer region in this nanopore is primarily populated by positively charged species. The relative magnitude of the double layer signals from different analyte molecules is only weakly sensitive to the concentration of the analyte in solution, which together with modeling results indicates that the signal is due to single molecules translocating the nanopore. The double layer potential signal calculated from the converged computational model of the system reflected the experimental trends, confirming the dependence of the signal on the charge of the analyte with weak dependence on the size of the molecule. In computational and experimental studies, the potential signal was found to be consistent with Debye's analysis of the electrical atmosphere due to charged species in solution. The double layer potential signal offers a fundamental improvement over the ionic current signal in that the potential signal is independent of the solution pH and the transport parameters of the analyte molecule.

Referring to FIG. 1a, a nanopore device system for molecular detection in a solid-state nanopore is shown generally as 10. The first reservoir 12 is in fluid communications with a second reservoir 14. A nanopore or pore chip 16 is disposed between the two reservoirs. The nanopore can include an opening 18 that is defined in a first layer 20 and second layer 22. In one embodiment, the opening is less than 1000 nm in diameter. There can be an electrolyte shown, generally as 24, in contact with an electrode 26 and the second layer. A first sensor 28 can be disposed between the electrode and the second layer to measure EDL potential signal between the second layer and the electrode. A second sensor 30 can be included to measure the ionic current between the first reservoir and the second reservoir; in some embodiments one meter contains multiple sensors and provides all detection. A processing assembly 32 can be in electrical communications with the first sensor and second sensor. The processing assembly can include a computer process for executing computer readable instructions for filtering a first sensor output and a second sensor output using a digital passband filter, determining a drop in the EDL capacitance between the second layer and the electrode, determining a spike in the ionic current between the first reservoir and the second reservoir, temporally correlating the drop and spike, performing an analysis selected from the group consisting of: comparing the drop in the EDL capacitance with a property of an analyte, comparing a spike in the ionic current with a property of an analyte, comparing the drop in the EDL capacitance with an identity of an analyte, comparing a spike in the ionic current with an identity of an analyte, and any combination thereof.

Figure 1B:
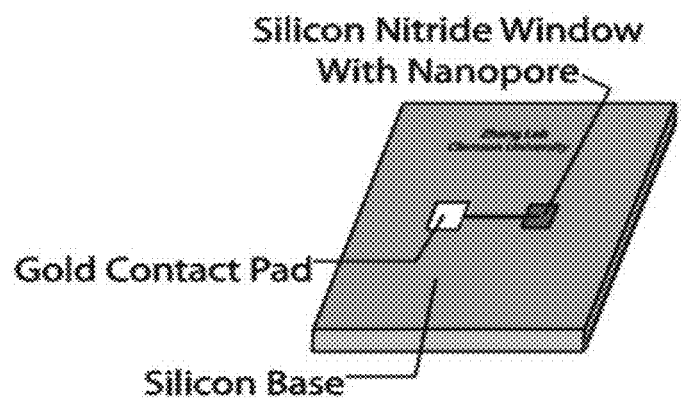
FIG. 1B is an exemplary nanopore/pore chip that includes the $Si_3N_4$/gold membrane, where $Si_3N_4$ is gray, gold is light gray.
Figures 1C, 1D:
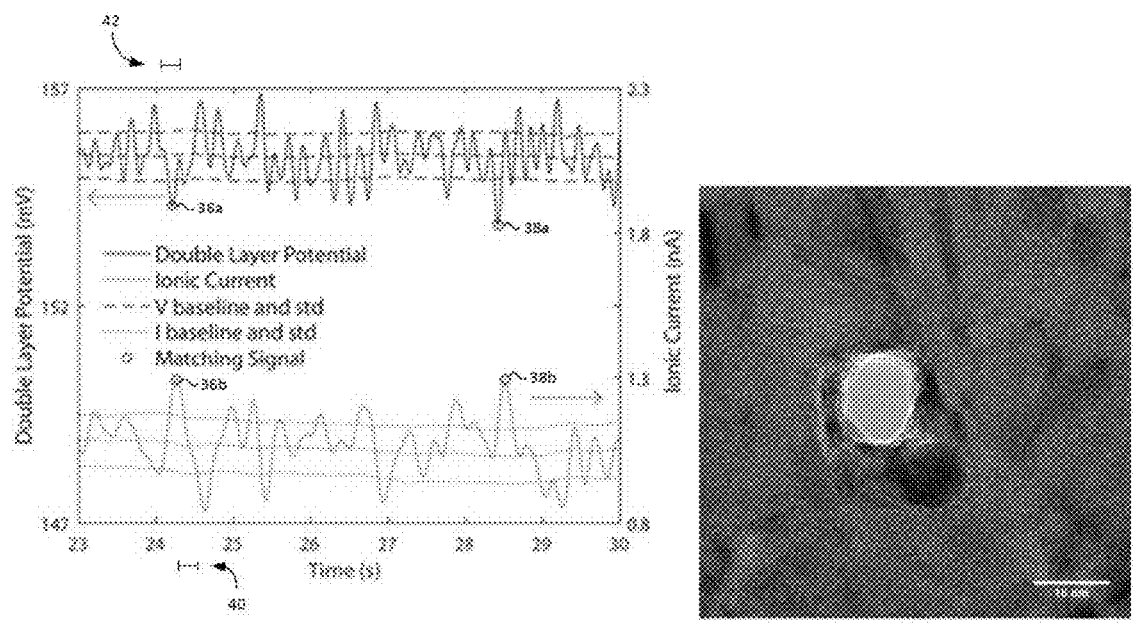
FIG. 1C shows how the signals collected were difference measurements occurring in tandem, measured from the local baseline of the ionic current and double layer potential traces. Note that the circles in the two signals mark the matching event signals.
FIG. 1D includes a transmission electron microscopy (TEM) image of a nanopore with 10 nm diameter in the Si3N4/gold membrane. The pictured nanopore was fabricated by direct TEM e-beam drilling instead of ICP etching (the silicon substrates of devices prepared with the latter method were too large and too thick to insert into a TEM for imaging). However, fluidic evaluation of the devices indicates that the imaged TEM nanopore is comparable in size to the ICP etched nanopore used in this study.

An embodiment of the nanopore system is also shown. This embodiment includes a $Si_3N_4$/gold nanopore and a supporting solution. The solution can contain the analyte of interest and supporting electrolyte which are transported through the nanopore. An electric field can be generated across the nanopore by application of a voltage clamp, allowing the ionic current through the nanopore to be monitored. A constant electrical current is supplied to the gold layer of the nanopore. The signals collected were difference measurements occurring in tandem, measured from the local baseline of the ionic current and double layer potential traces as shown in FIG. 1c. Note that the circles (36a, 36b) and (38a and 38b) in the two signals mark the matching event signals and show a temporal correlation.

In one embodiment, the width of the ionic charge signal 40 can be compared to the EDL signal width 42 and if these widths are within a predetermined range, it represents that the ionic charge and EDL signals are due to the same molecule passing through the nanopore.

The invention can also be used to provide for a dual channel DNA sequencing system in which measurements are made in parallel for the ionic current and the electrochemical potential of the electrical double layer within a solid-state nanopore. By increasing the quantization of the two measurement channels and considering a multi-nucleotide DNA input with a hidden Markov model approach, the nanopore sensor system can be tuned for higher sequencing accuracy. The double layer potential signal alone was sufficient to produce DNA base calling accuracy of >99% in the evaluation set of short DNA. In one embodiment, the maximum sequence accuracy of the ionic current signal alone was found to be limited to less than 80% with the same evaluation set of DNA. When the resolution of the measurement channels (and therefore the sequencing accuracy) was at a sub-maximal value, higher accuracy is provided than in either individual channel by combining the measurements in parallel. By establishing this approach of dual channel sequencing with consideration of the multi-nucleotide resolution of the nanopore sensor, a new method of high accuracy DNA sequencing with unmodified DNA in a non-functionalized, solid-state, nanopore is provided. This method requires only minimal reagents consisting of the electrolyte solution and DNA sample. No operational life-time for the device has been noted, with measurements made from the same device over a timescale of months with no noticeable degradation.

Since it is possible to simultaneously measure the double layer potential and ionic current through the nanopore, the prevent invention can provide an error tolerant DNA sequencing method in which the two sensing modalities that can be used individually or in combination. By manipulating the quantization of the outputs in the sensor design, the invention can account for the situation where multiple nucleotides are interrogated by the sensor (1 or 2 nucleotide combinations).

An advantage of this invention is that the nanopore may be produced by nanoscale fabrication techniques with conventional solid-state materials, the device is reusable with a long operational life, and requires only minimal reagents (aqueous electrolyte solution and DNA). By taking a computational and machine learning approach with a dual-channel signal, a method of improved nanopore sequencing is accomplished without chemical modification of the DNA or sophisticated translocation controls.

The presently disclosed subject matter is directed to an improvement to a solid-state nanopore device. In some embodiments, the electrical double layer (EDL) nanopore devices include an insulating substrate defining a nanopore therethrough; a nanopore electrode exposed in a portion of the nanopore; and an electrolyte in contact with the nanopore electrode. In particular embodiments, the nanopore electrode defines a conductive ring exposed around an inner surface of the nanopore.

According to some embodiments of the invention, the insulating substrate includes a first insulating layer, the nanopore electrode includes a conductive layer on the first insulating layer, and the nanopore device further includes a second insulating layer on the conductive layer so that the conductive layer is between the first and second insulating layers. The nanopore extends through the first and second insulating layers and through the conductive layer so that portions of the conductive layer are exposed in the nanopore between the first and second insulating layers.

According to some embodiments of the invention, the solid-state nanopore device also includes a reference electrode in electrical contact with the electrolyte; and a meter or sensor configured to measure multiple electrical signals in the nanopore device. In some embodiments, the meter or sensor is a multiple channel device capable of measuring the signals, including by two or more separate parallel channels. In some embodiments, the meter or sensor is electrically coupled between the nanopore electrode and the reference electrode. The meter or sensor may be comprised of more than one meter or sensor. In some embodiments, the meter or sensor is configured to measure or detect the double layer potential, or charging potential. In some embodiments, the meter or sensor is configured to measure or detect an ionic current. In some embodiments, the meter is further configured to correlate different measurements, for example, with different monomers of a polymer, or an analyte from a mixture of analytes.

The signals that can be measured can be measured individually or in any combination and include measurements of the double layer potential, ionic current and analyte mobility. In some embodiment, multiple simultaneous signals are measured and used for analyte identification. In single analyte characterization where results will depend on repeatability, high precision measurements are desired, and the algorithmic approach can be tuned for a given task by optimizing for high accuracy (using a multi-signal approach) or high precision (using the double layer potential alone).

In some embodiments, ionic current and double layer potential signals are measured for DNA sequencing. In some embodiments, the measurements are correlated with the different monomers of a polymer, such as the nucleotides of a polynucleotide. Furthermore, in some embodiments, the nanopore device further includes a driver circuit configured to generate a biasing potential across the nanopore of the device to induce an analyte, such as a polynucleotide, to translocate through the nanopore.

Provided according to some embodiments of the invention are methods of determining the nucleotide sequence of a polynucleotide. Such methods include measuring multiple simultaneous signals of ionic current and double layer potential as the polynucleotide translocates through the nanopore; and correlating the measured signals with nucleotides of the polynucleotide. In some embodiments, one nucleotide of the polynucleotide translocates at the surface of the nanoelectrode at a particular time. In particular embodiments, methods of determining a nucleotide sequence of a polynucleotide include (i) inducing the polynucleotide to translocate through a nanopore of the nanopore device according to an embodiment of the invention; (ii) measuring simultaneous signals of ionic current and double layer potential; and (iii) temporally correlating the signals as the polynucleotide translocates through the with the nucleotides of the polynucleotide. In some embodiments, reagents such as NaF, NaOH and $H_2O$ are used.

In some embodiments, a method is provided for determining the presence and/or a property of an analyte in a mixture of analytes that includes (i) inducing the analyte to translocate through a nanopore of a nanopore device; (ii) measuring signals comprising double layer potential, ionic current and/or analyte mobility as the analyte translocates through the nanopore; and (iii) correlating the signals as the analyte translocates through the nanopore with the identity and/or property of the analyte. In some embodiments, such measurements can be assessed with clustering techniques.

The term "meter" or "sensor" is meant to encompass one or more devices such as a voltmeter, multi-meter or other measurement equipment, as well as other electronic equipment used to obtain, process or analyze data obtained from the measurements. The meter can be configured to apply an AC electrical signal between a nanopore electrode and a reference electrode, and to use the applied electrical signal to determine a measurement. A driver circuit can be configured to generate a biasing potential that induces analytes to translocate the nanopore, as is well-recognized in the art.

The devices and methods described herein may also be used with other polymers, whether organic or inorganic, analytes, or other mixtures to determine the monomer sequence of the polymer or the composition of a mixture of analytes. In some embodiments, the polymer is a linear polymer. For example, a polypeptide or oligopeptide, including both natural and/or synthetic amino acids, may be sequenced after denaturizing to form a linear polymer chain. An analyte includes any chemical or biological entity that can be identified, detected and/or quantified by the methods disclosed herein.

Biological analytes include microorganism, cells, cell products, or biological molecules, or any other biological analyte known to those of ordinary skill in the art.

Microorganisms encompass microscopic living systems. Examples of microorganisms include viral particles such as virions, prions or viriods; bacteria; fungi; archea; protists; microscopic algae; plankton; and planarian. Cells can include both prokaryotic and eukaryotic cells, including both natural and recombinant cells. Cell products include constituents of cells such as cell membranes and organelles. Biological molecules refer to molecules produced by a living organism, and the synthetic analogs of such molecules. Examples of biological molecules include carbohydrates such as glucose, disaccharides and polysaccharides; proteins; lipids (including lipid bilayers); and nucleic acids (polynucleotides), such as any type of DNA and RNA. Biological molecules may also be small molecules, including monomers and oligomers of other biological molecules, e.g., nucleic acids, nucleotides, fatty acids, etc. The biological molecules may be naturally occurring or synthetic, or may include both naturally occurring and synthetic portions. Thus, the term biological molecule also includes derivatives such as conjugated nanoparticles of biological molecules. Other biological polymers may also be sequenced by methods described herein.

Non-biological analytes and chemical analytes refers to molecules and entities that are not a biological molecules, as defined above. Such molecules may be organic in some embodiments, or inorganic in some embodiments, or a combination of organic and inorganic moieties. A non-biological molecule may be synthetic or naturally occurring. As an example, some synthetic polymer nanoparticles may be non-biological in nature. Some other polymers that may be sequenced by the methods described herein may also be non-biological in nature.

Those of ordinary skill in the art will recognize factors and methods for reducing systemic noise, decreasing physical resolution of the nanopore, increasing the number of data channels obtained from the sensor or meter, and utilizing one or more signals according to the application and as taught herein.

EXAMPLES

The presently-disclosed subject matter is further illustrated by the following specific but non-limiting examples. The examples may include compilations of data that are representative of data gathered at various times during the course of development and experimentation related to the presently-disclosed subject matter. Furthermore, some of the examples described herein may be prophetic examples.

Example 1

The energetic properties of the EDL have been largely neglected in nanopore sensing applications, even though the electrochemical potential of the EDL within a nanopore is determined by the molecular contents of the solution. A general analytical approach to considering the electrochemical potential of a solution of charged molecules was considered by Huckel and Debye. This approach offers insight into the relevant parameters to consider in nanopore sensing. When an electrolyte is dissolved, the free energy of the solution is a function of the concentration, valence charge, permittivity, and radius of the components of the electrolyte solution. The expression for the potential energy stored in an electrolyte solution can be expressed as a sum of the thermodynamic potential of the molecules in solution and the electrical atmosphere created by the charges of those molecules: $(\emptyset = \emptyset_k + \emptyset_e)$, where $\emptyset$ is the total electrochemical potential of the solution, $\emptyset_k$ is the physical potential, and $\emptyset_e$ is the electrical atmosphere. The total potential may be calculated as sum of the contributions of all types of molecule (j) in the solution from j=0 to s, where j=0 refers to the solvent. The physical potential ($\emptyset_k$) is the sum of the number of molecules of type/with thermodynamic potential $\emptyset_j$ for all s types of molecules in the solution. Physical potential was described by Planck as $(\emptyset_k = \Sigma_0^s N_j (\emptyset_j - k_B \log(X_j)))$ (where $N_j$ is the number of molecules of type j, $\varphi$ is the thermodynamic potential of molecules of type j, $k_B$ is the Boltzmann constant, and $X_j$ is the mole fraction of j.

The contribution of the electrical atmosphere as defined by Huckel and Debye includes consideration of the size, permittivity, number, and charge of the molecules in the solution. The potential of the electrical atmosphere was found by summing the distributed electric field of each molecule in the solution and may be written:

$$\left( \phi_e = \sum_0^s N_j \frac{z_j^2 q^2}{\varepsilon T} \frac{x}{3} X_j \right)$$

where $z_j$ is the valence charge of j, q is the elementary charge $\varepsilon$ is the permittivity of the solution, T is the temperature, an x is the inverse of the Debye length ($x=1/\lambda_D$). The term $X_j$ is an expansion of a complicated integral and is a function of x and the radius $r_j$ of molecules of type j:

$$\left( X_j = 1 - \frac{3}{4} x r_1 + \frac{3}{5} x r_j - \dots \right)$$

The physical potential ($\emptyset_k$) accounts for the free energy and Brownian motion of uncharged molecules, while the electrical term ($\emptyset_e$) considers the contribution of the charge of each molecule in solution to the electrical atmosphere of the solution. In this study, electrical interactions are probed, and our system will be determined by the electrocal atmosphere term ($\emptyset_e$).

When an electrolyte solution is placed in contact with an electrode, a charge gradient forms in response to the electrical potential of the surface. The charge gradient is described using the Gouy-Chapman-Stern model of the EDL. The electrochemical potential stored in the EDL must be balanced by the potential of the electrode. In a system in which the electrode potential is not fixed, the energetic balance is determined by the electrochemical potential of the electrical double layer and the charge accumulated on the electrode. According to Planck, Huckel, and Debye, the energetic balance may be expected to be a function of the valence, size, concentration, and identity of the constituent species of the solution. By measuring the potential at a nanopore electrode, we may get a signal that represents the structure and properties of the constituent species within the nanopore. Because the analyte molecules must move through the EDL within a nanopore, we may detect alterations to the EDL structure due to the physical and electrical differences between the supporting electrolytes and analyte molecules. With such a sensing mechanism, analyte orientation has less effect on the measured signal than in other nanopore sensors like the tunneling or conductance types due to the axisymmetry of the measurement in a nanopore EDL ring electrode. Additionally, the mechanism responsible for the ionic current signal is not precluded by the acquisition of the EDL signal. This mechanism should provide complementary measurements of individual molecular analytes by allowing simultaneous collection of both ionic current and double layer potential signals. By exploiting the changes that occur in the EDL structure when an analyte translocates a nanopore, we demonstrate a new double layer detection method sensitive to transient alterations to the electrochemical potential within the nanopore.

Methods

Experimental Methods

The fabrication and arrangement of the nanopore system is similar to what has been described in our previous work. Briefly, a thin membrane was fabricated by depositing LPCVD $Si_3N_4$ (50 nm thick) over a silicon substrate. The silicon substrate was etched in 45% KOH solution to release the $Si_3N_4$ membrane. An electrode layer of gold (15 nm), bonded by a thin titanium adhesion layer, was deposited and patterned over the $_{Si3N4}$ membrane. A nanopore was formed in the gold/$Si_3N_4$ membrane with e-beam lithography and inductively coupled plasma (ICP) etching. E-beam resist (350 nm of ZEP-520a) was patterned with e-beam lithography as a nanopore with a 10 nm diameter. A range of e-beam doses were considered in the range of 1000 to 40 000 $\mu C/cm^2$ where the highest quality devices resulted from doses of <10 000 $\mu C/cm^2$. The device considered in this study was patterned with an e-beam dose of 3000 $\mu C/cm^2$. Nanopores were etched with ICP for 60 s using the etch parameters listed in Table 1.

TABLE 1

ICP etch settings.

| Etch Parameter | Value | Unit |
| --- | --- | --- |
| Coil power | 2600 | W |
| Platen power | 45 | W |
| Pressure | 5 | mT |
| Temperature | 10 | C. |
| $CHF_3$ | 20 | sccm |
| $O_2$ | 5 | sccm |
| Ar | 30 | sccm |

A single etch recipe was used for both the $Si_3N_4$ and gold layers. Nanopores formed in this way were evaluated in 100 mM NaF solution and those with a conductivity of <2 nS were selected for further experimental evaluation, where conductance <20 nS typically corresponds to a diameter of <10 nm in solid-state nanopores (FIG. 1(a)) [7]. A nanopore diameter of 1-10 nm was estimated by noting that rectification and EDL overlap effects (such as conductance gating) are typically only observed in nanopores smaller than 10 nm and that the size of the analytes considered approach a maximum diameter of 0.8 nm.

The nanopore device was installed in a flow cell which included two fluid reservoirs and access to the gold electrical contact of the nanopore (FIG. 1(a)). A constant trans-pore potential (10 mV) was applied across the nanopore between the two reservoirs of the fluidics cell. The gold layer of the nanopore was charged by a constant electrical current (37.4±3.2 pA). The ionic current through the nanopore and the electrical potential measured at the gold layer were digitized and recorded. The trans-pore potential and ionic current were produced and acquired, respectively, by a patch clamp amplifier (Molecular Devices, Axopatch 200B, CA) and two silver/silver chloride (Ag/AgCl) electrodes. The constant charging current was produced with an external potentiostat (Princeton Applied Research, Versastat MC, TN). The signal traces were recorded at 80 000 samples per second using custom software (Mathworks, Matlab 2012a, MA). All experiments were performed in triplicate and conducted at room temperature with system components operating relative to a common electrical ground.

With a focus on translocation events, we developed an algorithm to identify transient spike signals in the double layer potential and ionic current. The particular signals we sought to quantify were deviations from the baseline due to a disparity in the number of molecules that translocate through the nanopore. The baseline double layer potential can be attributed to the equilibrium between the solution and the nanopore electrode and the baseline ionic current to the steady-state ionic flux through the nanopore. In both cases, the steady-state value will be influenced by the concentration and chemical makeup of the solution. We expect that the transient spike signals that we detect will be due to the stochastic translocation of one or a few analyte molecules. A sliding window filter was implemented with a width of 5 s in order to detect and quantify simultaneous transient spike signals in the ionic current and double layer potential traces (FIG. 1(c)). Signal magnitude was calculated as the difference between the central point and mean level within the sliding window. In order for a spike to be recorded as a transient signal, the spike must occur simultaneously in both the ionic current and double layer potential traces, be at least twice the standard deviation of the baseline, and a local extrema. In this way, random noise is screened and translocation events are confirmed by matching the ionic current signal and double layer signal. The algorithm was implemented in a custom software package (Mathworks, Matlab 2012a, MA) and all data analysis occurred in post-processing.

Computational Methods

Figure 2A:
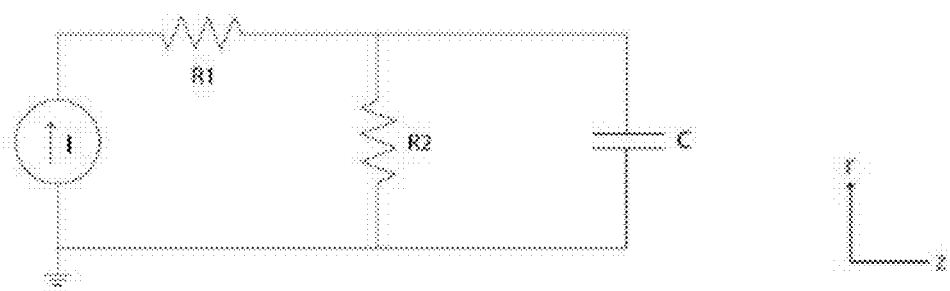
FIG. 2. A. A circuit model is shown for the system response to charging of the double layer. R1 is the input resistance and R2 is the leakage resistance. C is the double layer capacitance at the nanopore/solution interface. A charged spherical particle was evaluated within the nanopore lumen at charges levels of $z_j$=0, −1, −2, and −3 and radii of 0.2, 0.3, and 0.4 nm.
FIG. 2B shows the system was modeled as a conical nanopore in an axisymmetric coordinate system. A compact layer was explicitly defined as region of adsorbed ions and solvent at the wall of the nanopore. The electrical permittivity within the compact layer smoothly varied from the permittivity of the electrolyte cation to the solution permittivity (left inset). The corners of the compact layer were rounded at the nanopore openings to reduce computational load (right inset)
FIG. 2C provides a 3D view of the rotated conical geometry of the computational model.
Figure 2B:
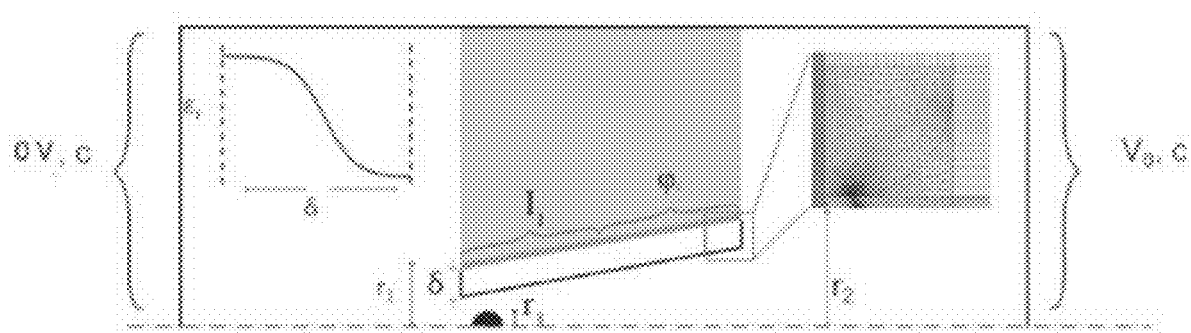

To have a better understanding of the underlying physics, a computational model of the nanopore system was developed by extending our previous modeling work in a finite element multiphysics modeling package (Comsol 4.4) [20]. The model was constructed in two-dimensions with axisymmetry, to take advantage of the rotational nature of the nanopore (FIGS. 2(a)-(c)). Fully coupled Nernst-Planck, Stokes, and Poisson equations were solved over the appropriate model domains, as discussed in our previous work (model parameters are listed in Table 4). The electrolyte solution consisted of aqueous NaF. The surface potential ($j_2$) of the $Si_3N_4$ layer of the nanopore was defined in a manner consistent with previous studies and the work function potential of $Si_3N_4$. In order to simulate the charging of the EDL capacitance, the surface of the gold layer was defined in terms of the potential across a capacitor in an equivalent circuit [20, 24, 25]. The overall charging behavior observed in the experimental system was modeled as an equivalent circuit in the computational model (FIG. 2(a)). The equivalent circuit was necessary to account for the system impedance and the steady-state charging behavior of the nanopore. The capacitor voltage (VDL) was considered in the computational model with a potential defined by the capacitor charge and the double layer capacitance:

$$\left( C_{EDL} = \varepsilon\varepsilon_0 \left( \frac{\delta^2 V}{\delta r \delta V_{DL}} \right) \right).$$

The double layer capacitance was coupled to the governing equations in the model and self-consistently and iteratively solved. The permittivities of the supporting ions and analytes were calculated by solving the Clausius-Mossotti relation for permittivity using polarizability ($\alpha'$) values (Table 2).

TABLE 2

Molecular analytes and supporting ion characteristics

|  | Citric Acid | L-Ascorbic acid | Oxalic acid | Hydroquinone | $K^+$ | $Na^+$ | $Cl-$ | $F-$ |
|---|---|---|---|---|---|---|---|---|
| pKa 1 | 3.14 | 4.1 | 1.23 | 10.35 | | | | |
| pKa 2 | 4.75 | 11.7 | | | | | | |
| pKa 3 | 6.39 | | | | | | | |
| Expected valence charge | −3 | −2 | −1 | −1 | 1 | 1 | −1 | −1 |
| Molar mass (g mole$^{-1}$) | 210.14 | 176.12 | 90.03 | 110.11 | 39.1 | 22.99 | 35.45 | 19.00 |
| Density (g cm$^{-3}$) | 1.67 | 1.65 | 1.90 | 1.30 | 0.86 | 0.97 | 1.56 | 1.51 |
| Estimated spherical radius (nm) | 0.37 | 0.35 | 0.27 | 0.32 | 0.26 | 0.21 | 0.21 | 0.17 |
| Polarizability (Bohr$^3$) | 69.87 | 83.33 | 55.22 | 61.42 | 32.7 | 7.64 | 1.25 | 0.26 |
| Permittivity | 1.78 | 2.23 | 3.31 | 2.11 | 2.10 | 1.41 | 1.06 | 1.02 |

TABLE 3

The valence charge of the molecular analytes at different pHs.

| | pH | | | | | | |
|---|---|---|---|---|---|---|---|
| | 1 | 2, 3 | 4 | 5, 6 | 7, 8, 9, 10 | 11 | 12 |
| Citric acid | 0 | 0 | −1 | −2 | −3 | −3 | −3 |
| L-Ascorbic acid | 0 | 0 | 0 | −1 | −1 | −1 | −2 |
| Oxalic acid | 0 | −1 | −1 | −1 | −1 | −1 | −1 |
| Hydroquinone | 0 | 0 | 0 | 0 | 0 | −1 | −1 |

Figure 2C:
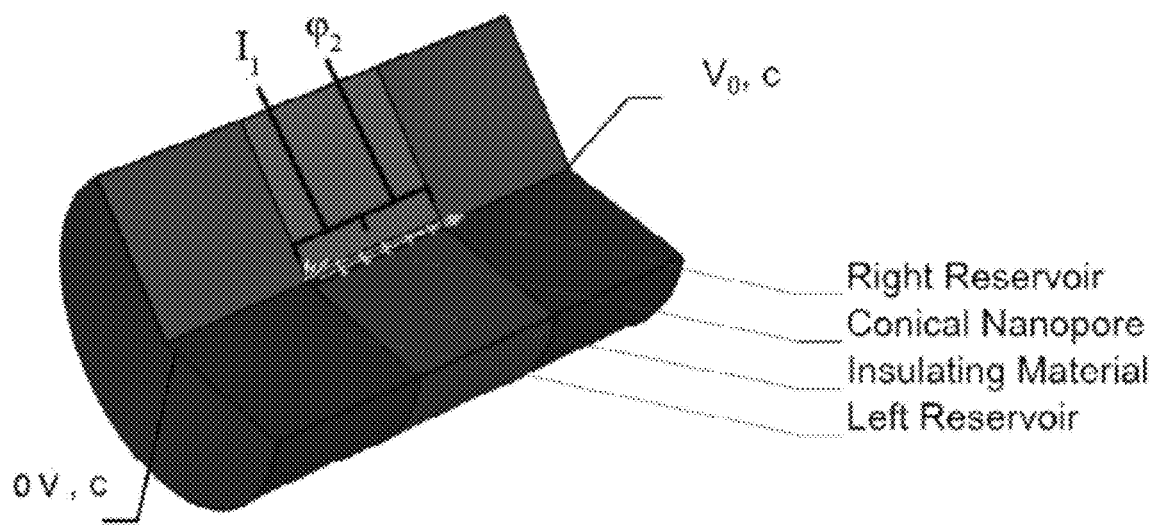

Polarizability was obtained from density functional theory calculations performed with Gaussian quantum mechanical modeling software (Gaussian, Gaussian 09, CT). The permittivity of the supporting cation defined the permittivity of the compact layer at the nanopore surface. The time domain response of the double layer potential in our system is described by the expression:

$$V_{DL}(t) = I\left(\frac{e^{-\frac{t}{R_2 C_{EDL}}}}{C_{EDL}} + R_1(\delta(t) - 1)\right)$$

where the terms correspond to the electrical elements in the equivalent circuit shown in FIGS. 2c and $d(t)$ is the Dirac-delta function. Experimentally, the potential across the constant current source ($V_I(t)$) is recorded for evaluation. The difference between these terms ($V_I$ and $V_{DL}$) is the potential across the resistor $R_1$ ($V_1 = IR_1$), which disappears in the difference measurement of the double layer signal. The time dependent potential measured at the current source is:

$$V_I(t) = I\left(\frac{e^{-\frac{t}{R_2 C_{EDL}}}}{C_{EDL}} + R_1\delta(t)\right).$$

TABLE 4

Constants, variables, and values.

| Symbol | Description | Unit |
|---|---|---|
| $a_j$ | Activity of j | 1 |
| A | Minimum cross sectional area of the conical nanopore | nm$^2$ |
| a' | Polarizability volume | Bohr$^3$ |
| c | Concentration of the bulk solution in the reservoirs | millimolar |
| $c_j$ | General concentration term for solvated electrolytes | millimolar |
| $C_{EDL}$ | Electrical double layer capacitance | F m$^{-2}$ |
| d | Density | g cm$^{-3}$ |
| $D_j$ | Diffusion coefficient for solvated electrolytes  $D_{Cl}$ | 2.03 × 10$^{-5}$ (cm$^2$ s$^{-1}$) |
| | $D_K$ | 1.96 × 10$^{-5}$ (cm$^2$ s$^{-1}$) |
| | $D_{Na}$ | 1.334 × 10$^{-5}$ (cm$^2$ s$^{-1}$) |
| | $D_F$ | 1.475 × 10$^{-5}$ (cm$^2$ s$^{-1}$) |
| | $D_{H+}$ | 7.9 × 10$^{-5}$ (cm$^2$ s$^{-1}$) |
| δ | Thickness of the compact layer | nm |
| e | Electronic charge | 1.602 × 10$^{-16}$ C |
| $\varepsilon_r$ | Relative permittivity | |
| $\varepsilon_0$ | Permittivity of free space | 8.8542 × 10$^{-32}$ (F m$^{-1}$) |
| $\varepsilon_p$ | Permittivity at the wall of the nanopore | 2 |
| $\varepsilon_s$ | Nominal permittivity of the electrolyte solution | 80 |
| $F_c$ | Faraday's constant | 96 485.34 (C mole$^{-1}$) |
| $F_V$ | Volume force | N m$^{-3}$ |
| g | Fitting term for smoothly varying permittivity in the compact layer | |
| γ | Fluid viscosity | Pa s |
| $\gamma_j$ | Activity coefficient of j | 1 |
| h | Fitting term for smoothly varying permittivity in the compact layer | |
| I | Identity matrix | |
| $I_l$ | Electrical current applied to gold layer | pA |
| $k_B$ | Boltzmann constant | 1.381 × 10$^{-23}$ (m$^2$ kg s$^{-2}$ K$^{-1}$) |
| Kn | Knudsen number | 1 |
| L | Nanopore length | nm |
| $\lambda_D$ | Debye length | nm |
| M | Molar mass | g mole$^{-1}$ |
| μ | Electrochemical energy of a solution | J mole$^{-1}$ |

TABLE 4-continued

Constants, variables, and values.

| Symbol | Description | Unit |
|---|---|---|
| $\mu^0$ | Standard electrochemical energy of a solution | J mole$^{-1}$ |
| $\mu_{en}$ | Electroosmotic mobility | m$^2$ (V$^{-1}$ s$^{-1}$) |
| $\mu_{m,j}$ | Mobility of solvated electrolytes $\mu_{m,Cl}$ | 8.23 × 10$^{-13}$ (s mole kg$^{-1}$) |
|  | $\mu_{m,K}$ | 7.95 × 10$^{-13}$ (s mole kg$^{-1}$) |
|  | $\mu_{m,Na}$ | 5.48 × 10$^{-13}$ (s mole kg$^{-1}$) |
|  | $\mu_{m,F}$ | 6.05 × 10$^{-13}$ (s mole kg$^{-1}$) |
| $N_{AV}$ | Avogadro's number | 6.022 × 10$^{23}$ |
| $N_j$ | Number of molecule j in solution | 1 |
| P | Pressure | Pa |
| $\varphi_2$ | Unbiased surface potential due to the material work functions | −0.2 V |
| $\varphi_e$ | Debye electrical potential of a solution | V |
| $\varphi_j$ | Thermodynamic potential of molecule j | V |
| $\varphi_k$ | Classical Planck potential of a solution | V |
| $Q_D$ | Double layer electrode charge | C m$^{-2}$ |
| $r_a$ | Radius of the nanopore at an arbitrary position | nm |
| $r_1$ | Radius of the small opening of the nanopore | nm |
| $r_2$ | Radius of the large opening of the nanopore | nm |
| $r_3$ | Radius of the simulated molecule | nm |
| $r_j$ | Radius of molecule j | nm |
| R | Gas constant | 8.314 (J mole$^{-1}$ K$^{-1}$) |
| $R^2$ | Coefficient of determination | 1 |
| $R_j$ | Rate of production of solvated electrolytes | mole (s$^{-1}$ m$^{-3}$) |
| $\rho_e$ | Distribution of charge carriers within the model | C m$^{-3}$ |
| $\rho_m$ | Fluid mass density | kg m$^{-3}$ |
| T | Temperature | 296.65 (K) |
| $\tau$ | Viscous stress tensor |  |
| u | Fluid velocity | m s$^{-1}$ |
| V | General potential trem within model | Volts |
| $V_0$ | Potential applied across the length of the channel | 0.15 (V) |
| $V_{DL}$ | Double layer potential | V |
| x | Inverse of the Debye length | 1/nm |
| $X_j$ | Mole fraction of j | 1 |
| $z_j$ | Valence of charged molecules $z_{Cl}$ | −1 |
|  | $z_K$ | +1 |

3. Results

3.1. Consideration of the Supporting Electrolyte Solutions

The prepared nanopore chip was placed in a fluidics cell containing an analyte solution consisting of an aqueous mixture of the analyte molecule (citric acid, hydroquinone, oxalic acid, or ascorbic acid in this study) at a low concentration (10$^{-8}$ M) and a supporting electrolyte (NaF) in a range of concentrations from 10$^{-7}$ to 1 M with logarithmic increments. In order to investigate any dependency of the signal on the analyte concentration, the concentrations of the molecular analytes were varied from 10$^{-8}$ to 10$^{-2}$ M in 10$^{-5}$ M NaF solution. Because NaF dissociates into Na$^+$ and F$^-$, and F$^-$ will form HF in solution (due to HF being a weak acid), it was important to ensure that the concentration of HF was negligible compared with the concentration of the molecular analytes and supporting electrolytes. Within the nanopore, the solution was determined to have a pH of 12 due to the relative magnitudes of the analyte signals (see discussion). The concentration of HF at this pH is expected to be at least an order of magnitude smaller than the concentration of the analyte molecules, and we treat this as negligible. The specific analytes used in this study were chosen to have distinct acid dissociation constants (pKas) and to be relatively similar in size (Table 2). In order to explore the effect of solution pH, citric acid was evaluated at pH 2.8, 3.9, 5.5, and 8.5 (values chosen to fall on distinct valence charge levels relative to the pKa) with and without NaCl as a supporting electrolyte. NaCl was chosen as the supporting electrolyte in this pH experiment in order to maintain a homogeneous ion population with the titration reagents, NaOH and HCl. It was desirable to avoid using HF as a titration reagent, due to the risk of damaging the nanopore device and because HF is a weak acid. In low pH conditions, the concentration of undissociated HF would increase to non-negligible levels. Since HCl and NaOH are a strong acid and base, respectively, there was no risk of producing undissociated molecules at low or high pHs.

3.2. The EDL Signal in Various Concentrations of Supporting Electrolyte

Figure 3A:
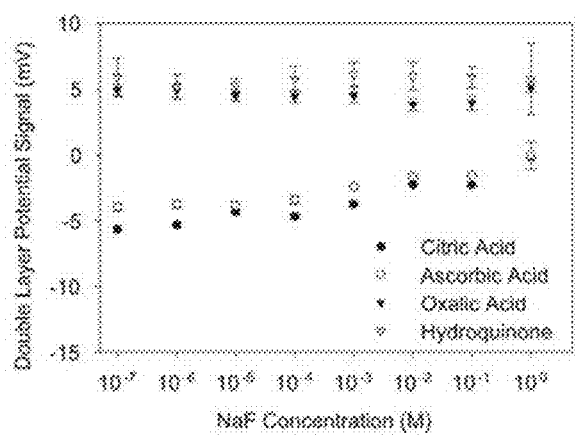
FIG. 3A shows the double layer potential signal from the molecular analytes maintains a consistent relative magnitude across a wide range of electrolyte concentrations. In NaF, sensitivity decreases at high concentrations.
Figure 3B:
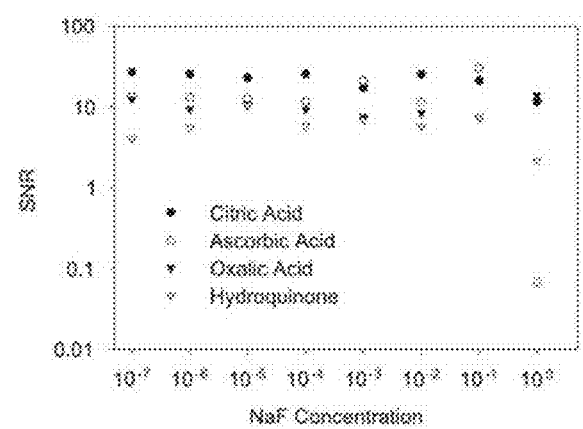
FIG. 3B shows the signal to noise ratio (SNR) varies by supporting electrolyte concentration and analyte species in NaF. The SNR drops off precipitously at 1 M NaF (corresponding to saturation of the NaF solution)
Figure 3C:
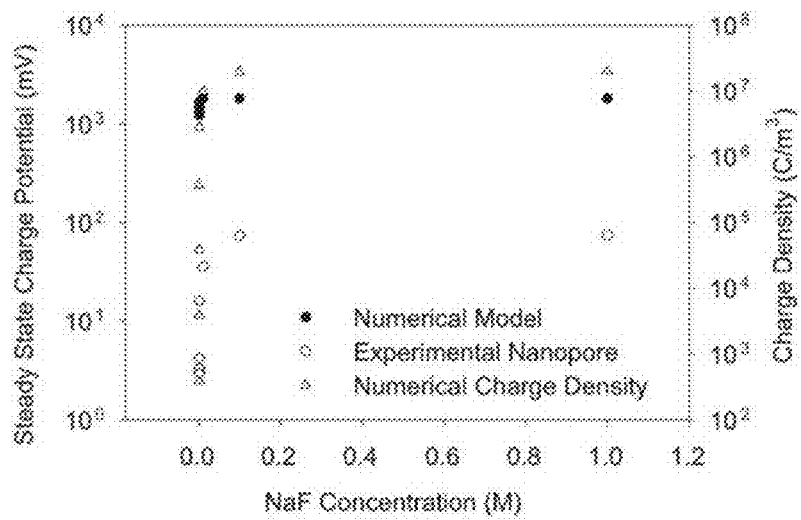
FIG. 3C demonstrates the loss of signal sensitivity at high concentrations is correlated to the saturation of the steady-state potential in both experimental and modeling systems. Saturation of the charge density within the biased region of the nanopore was observed in the computational model, corresponding to the loss of signal quality at high concentrations of supporting electrolyte.

The measured double layer potential signals for the analytes are shown in FIG. 3(a). The magnitude of the double layer signals for citric acid (CA) and ascorbic acid (AA) have logarithmic relationships with supporting electrolyte concentration (with coefficients of determination: ($R^2$=0.9084 for CA and $R^2$=0.9033 for AA). The logarithmic relationship was a poor fit for the double layer signals for oxalic acid (OA) and hydroquinone (HQ), which appeared to be constant for all supporting electrolyte concentrations considered. All comparisons between different analytes were significant within any given concentration (p<10$^{-5}$), including the lowest quality (lowest signal to noise ratio, SNR) measurements at the 1 M condition. The standard deviation of the signals increases at high supporting electrolyte concentrations with a corresponding decrease in SNR near 1 M in NaF (FIG. 3(b)). However, the relative signal magnitude for the analytes is consistent at all concentrations of NaF. Overall, hydroquinone was observed to produce the most positive signal magnitude, with oxalic acid producing a smaller positive signal. Ascorbic acid and citric acid produced negative signals, with citric acid producing the larger negative magnitude. At concentrations near solution saturation, the quality (SNR) of the signal decreases. Saturation of the solution at high concentrations was observed as saturation of the steady state double layer potential in both computational and experimental nanopores and as saturation of the charge density within the biased region of the nanopore in the computational model (FIG. 3(c)).

The Effect of pH on the EDL Signal

Figure 4A:
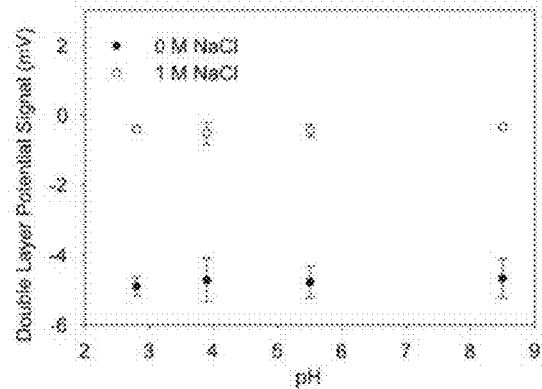
FIG. 4A indicates the double layer potential signal of citric acid is insensitive to pH at both high and low supporting electrolyte concentrations.
Figure 4B:
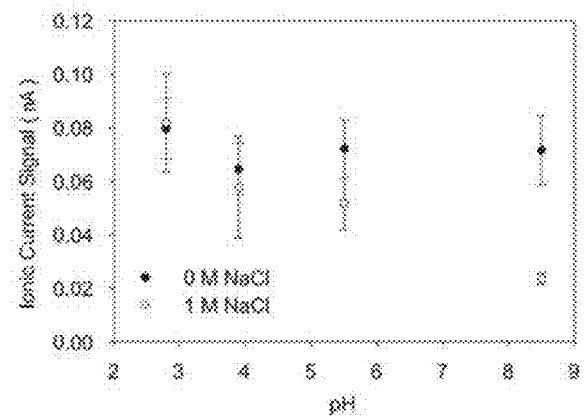
FIG. 4B The ionic current signal is sensitive to the pH of the solution, increasing in magnitude at low pH.

The double layer potential signal appears to be insensitive to change in pH of the solution while the ionic current signal tends to decrease with increasing pH, especially in the 1 M NaCl case (FIGS. 4(a) and (b)). Linear regression indicates that the double layer potential signal is not dependent on pH (p>0.2) for citric acid in solution with pH of 2.8, 3.9, 5.5, or 8.5. These pH values were chosen in order to produce different levels of charge on the citric acid analyte based on the analyte's dissociation constants (pKas). FIG. 4(b) shows that the ionic current signal is affected by the electrolyte concentration and pH, where the signal has an inverse relationship to pH (the signal decreases for higher pH values, p<0.05 for the 1 M case). The ionic current is weakly related to pH at low concentrations (p >0.05 for the 0 M case).

3.4. The Effect of Analyte Concentration on the EDL Signal

Figure 5A:
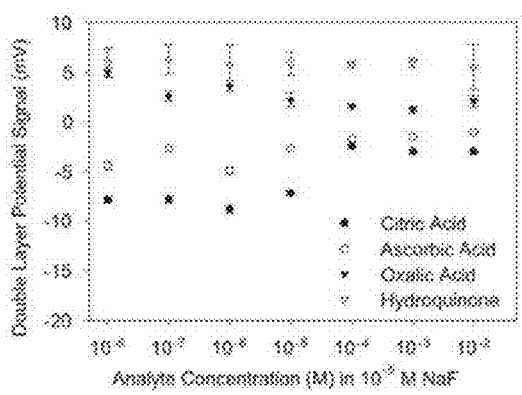
FIG. 5A The relative magnitude of the signals from the molecular analytes in $10^{-5}$ M NaF was consistent for a wide range of analyte concentrations. The signal range is decreased at concentrations greater than $10^{-5}$ M, corresponding to the transition from NaF dominant solution to molecular analyte dominant solution. The decrease in signal range may be explained by an increase in probability that additional molecular analytes may be present near the nanopore.
Figure 5B:
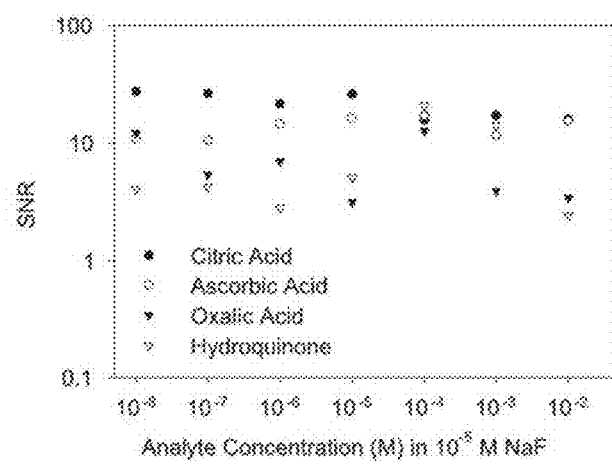
FIG. 5B The signal to noise ratio of the double layer potential signal at all analyte concentrations was comparable with the original measurements in varying concentrations of supporting electrolyte.
Figure 5C:
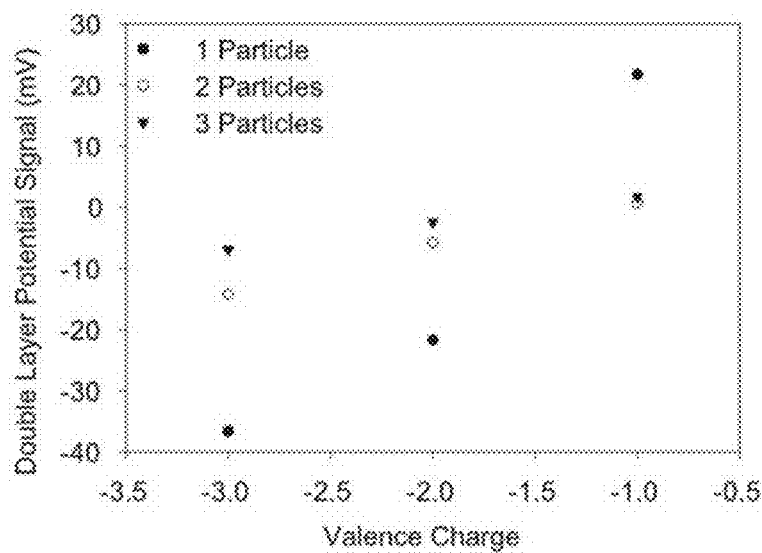
FIG. 5C Our computational results indicate that the presence of additional molecules within the unbiased lumen of the nanopore reduces the range of the double layer signal.

The double layer potential signals exhibited weak dependence on the concentration of the analyte (FIG. 5(a)). The relative magnitude of the double layer potential signals exhibited the same relative magnitude, regardless of the concentration of analyte or supporting electrolyte (FIG. 5(b)). The signal range between the highest and lowest double layer potential signals (the signals from hydroquinone and citric acid, respectively) decreased when analyte concentrations are higher than $10^{-5}$ M (from ~15 mV for analyte concentrations below $10^{-5}$ M to ~10 mV for analyte concentrations above $10^{-5}$ M). The decrease in signal range indicates an increase in the number of analyte molecules near the nanopore, consistent with our modeling results of multiple analyte particles near the nanopore (FIG. 5(c)), where the cases with 2 or 3 additional analyte particles near the sensing region yielded a reduced range for the double layer signal.

The Effect of Analyte Size and Charge in the Computational Model

Figure 6A:
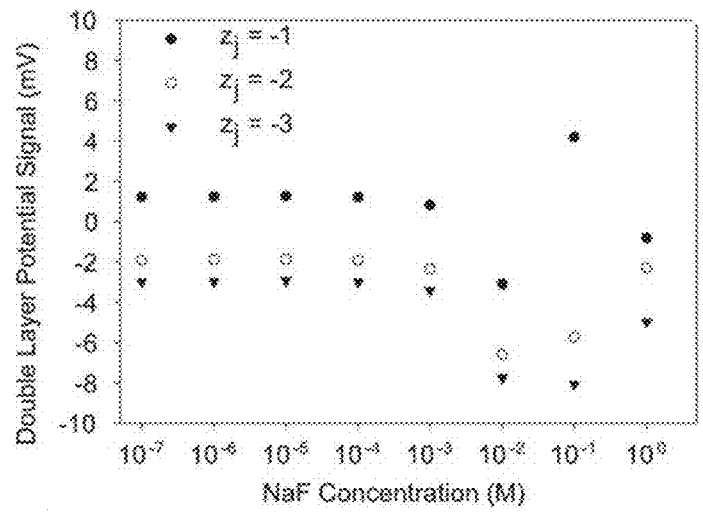
FIG. 6A The modeled double layer potential signal for analyte particle of radius 0.3 nm in NaF indicates that the sensitivity to particle charge is consistent with the experimental observations. More negative valence charge results in a more negative signal. Sensitivity is lost at high concentrations in NaF.
Figure 6B:
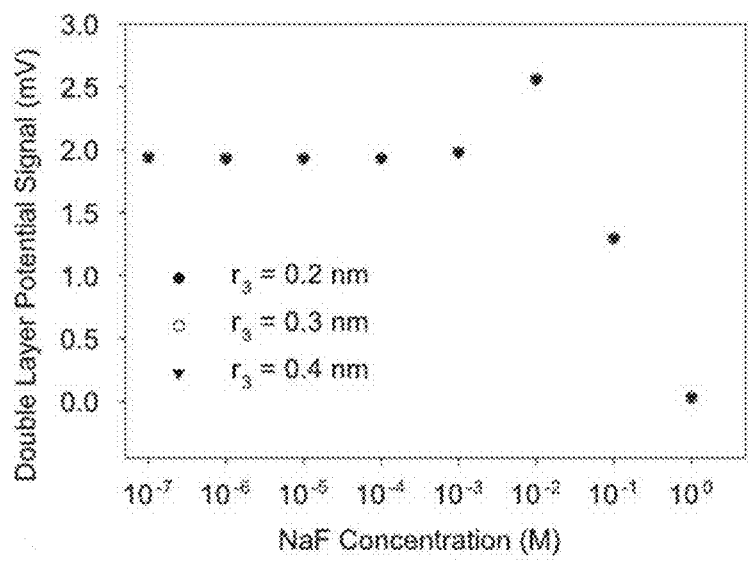
FIG. 6B. The modeled double layer potential is perturbed by the presence of an analyte particle with finite size. Size of the particle had little influence on the double layer potential in the model and did not contribute much to the separation of analyte signals.

FIG. 6(a) shows the double layer potential response in the computational model for particles with charges of $z_j = -1, -2,$ and $-3$ in NaF, which shows a similar trend as that observed experimentally for analytes with different valence charges. More negatively charged analyte particles produce more negative double layer potential signals. FIG. 6(b) shows the double layer potential signal caused by uncharged analyte particles of various sizes in NaF solution. At all concentrations, the effect of the analyte size only minimally contributes to the difference between signals. The magnitude of a signal due to an uncharged particle decreases dramatically at high electrolyte concentrations. Changing the permittivity of the analyte particle had no effect on the double layer potential signal (data not shown). However, considering the permittivity of the electrolyte ions at the surface of the nanopore (within the compact layer) was a critical factor in producing agreement between experimental and computational signals.

Discussion

Consideration of Analyte Effect on the EDL Signal

Through perturbation of the EDL by a translocating analyte molecule, we examined the effect of the size, permittivity, and charge of an analyte molecule on the charging potential of the EDL within the nanopore, keeping in mind Debye's analytical result for the electrical potential of a solution. The double layer potential signal at a given concentration of supporting electrolyte is primarily proportional to the expected charge of the analyte, however the difference between the signals generated by oxalic acid and hydroquinone (both of which are expected to carry the same valence charge) indicate that other physical parameters also have measurable influence. The effect of changing the size of the molecule in the computational model is small, indicating that the difference in signal between analytes is only weakly influenced by the size of the analyte molecule in the range considered. The size effect in the model is much smaller than observed experimentally between oxalic acid and hydroquinone, indicating a possible limitation of the model. Huckel and Debye's analytical characterization of the electrical potential of an electrolyte solution can be related to the effect of molecule size and charge; where changing the size of the analyte molecule alters the electrical atmosphere of the solution ($\phi_e$) through the displacement effect described by Huckel and Debye, while changing the charge of the analyte molecule affects the electrical atmosphere through both the addition of the analyte valence charge and the compensatory charge accumulation within the solution. We observed analyte dependent relationships to concentration of supporting electrolyte in the double layer potential signal. The logarithmic relationship between supporting electrolyte concentration and the signals produced by citric acid and ascorbic acid (CA and AA, respectively) may be due to screening of the relatively high valence charge at higher supporting electrolyte concentrations. The relatively constant signals of oxalic acid and hydroquinone (OA and HQ, respectively) may indicate less influence of screening due to their lower valence charge (FIG. 3(a)). We hence speculate that the species-dependent relationship between the double layer potential signal and supporting electrolyte concentration is related to the charge and size of analytes.

The Chemical Conditions of the EDL in a Nanopore

We consider the physical source of the double layer potential signal in terms of charge balance between the nanopore electrode and the solution within the nanopore. The charge density and structure of the EDL is related to the valence charge and size of the molecular analyte per our experimental observation and computational modeling. Since the valence charges of the analytes are dependent on the local pH, one might expect the double layer potential to be dependent on the intraluminal pH. We explored the relationships between pH, valence charge, and signal magnitude by varying the pH of the supporting electrolyte solution. Our experimental observations indicate that the double layer signal is insensitive to the solution pH while the ionic current signal is negatively correlated to pH at high supporting electrolyte concentrations. The dependence of the pH effect on supporting electrolyte concentration in the ionic current signal is likely related to buffering of the solution at high concentrations. The amount of titration reagent needed to change the pH in the high concentration case is larger than in the low concentration case, amplifying the pH effect. When the pH is lowered, the number of hydrogen ions ($H^+$) is increased while the ionic current signal tends to increase and the double layer potential signal remains nearly constant. This correlation implies that the ratio of charge carriers ($H^+:Na^+$) in the nanopore increases at low pH while the total number of charge carriers is governed by the electrical balance between the surface and solution. The ionic current signal increases due to a relative increase in diffusion coefficient because of the increased proportion of $H^+$ ions in the nanopore volume ($D_{H^+} > D_{Na^+}$, Table 4). Since the double layer potential signal is a function of the density of charge carriers within the nanopore, it does not ($\Sigma z_j n_j$) change as a function of pH. We speculate that the double layer signal is mediated by the balance of charge density in the EDL and the potential at the electrode. In order to characterize this energetic balance, we estimate the pH of the intraluminal environment by considering the variable valence charges and pKas of the analytes. Table 3 lists the expected charge on each analyte at different pHs based on the pKas of the individual analytes. The ordering of the double layer signal magnitudes implies that the observed signal is consistent with an intraluminal pH of 12, at which point the analytes can be expected to carry a maximal negative charge.

Evidence of a Single Molecule Source

It is believed that the experimentally measured double layer potential signal is the result of the translocation of single molecules. Because the signal we detect is a deviation from the baseline double layer potential or ionic current, our observation of stable relative magnitudes of the signals for various different analytes over a wide range of concentrations indicates that the analytes translocate in fixed proportions. That is, if the signal is due to a single molecule, it is always a single molecule that produces the spike signal, and if it is a few molecules, the number of molecules that produce the spike signal is believed to be consistent across analytes over a wide range of concentrations. Our modeling results show that adding molecules in the non-sensing (unbiased) region of the nanopore will result in a narrower signal range while adding molecules in the sensing region will result in a wider signal range (where signal range is defined as the difference between the signals of citric acid and hydroquinone or the difference between valence charge −3 and −1 molecules in this study). Experimentally we can see that the signal range appears to decrease when the analyte concentration is greater than the supporting electrolyte concentration, $10^{-5}$ M (FIG. 5(a)). Because there is good agreement between our modeling and experiment signals in terms of signal range and magnitude, we explain the change in signal range by considering the increased probability of multiple analyte molecules near the nanopore at high analyte concentrations. It is likely that additional analyte molecules are near the nanopore at high analyte concentrations, while the stable relative magnitude of the signals indicates that the presence of these molecules do not strongly alter the signal. These results strongly suggest that the signals occur due a single analyte molecule translocating per detected event.

Effects of Saturation of the Solution

It is believed that the decrease in SNR at high supporting electrolyte concentrations occurs due to saturation of the solution within the nanopore (saturation of NaF is near 1 M in standard conditions, 0.96 M at 21° C.; saturated solution was reached at approximately 1 M in this study). The SNR is consistent for electrolyte concentrations <1 M, and the sudden decrease in SNR at 1 M NaF is indicative of a saturation effect, where saturation of the solution would preclude significant changes to the electrochemical potential of the EDL. By considering the charge density and steady state double layer potential as response curves, we can explain the loss of signal quality at high concentrations of supporting electrolyte (FIG. 3(c)). The increase in steady-state potential and charge density (calculated from the model) slows at high concentrations, and a similar effect occurs experimentally to the steady state double layer potential. The decrease in slope of the response curves at high concentration will result in smaller signals from the analytes, resulting in the decrease in SNR observed at high concentrations of supporting electrolyte. Since the measured steady state potential and solution saturation follow similar curves, this may be a useful method for quantitatively characterizing solutions, as well as a method of characterizing individual analyte molecules.

Conclusion

A new modality for detecting and identifying small molecular analytes in a nanopore was developed. The double layer potential signal is dependent on the change in Debye potential of the solution within the nanopore due to the valence charge and size of the analyte molecule. The magnitude of the double layer potential signal is insensitive to pH and influenced by the concentration of the supporting electrolyte. The ionic current signal is sensitive to pH, indicating that the overlapped double layer region in this nanopore is primarily populated by positively charged species. The relative magnitude of the double layer signals from different analyte molecules is only weakly sensitive to the concentration of the analyte in solution, which together with our modeling results indicates that the signal is due to single molecules translo-cating the nanopore. The double layer potential signal calculated from the converged computational model of the system reflected the experimental trends, confirming the dependence of the signal on the charge of the analyte with weak dependence on the size of the molecule. In computational and experimental studies, the potential signal was found to be consistent with Debye's analysis of the electrical atmosphere due to charged species in solution. The double layer potential signal offers a fundamental improvement over the ionic current signal in that the potential signal is independent of the solution pH and the transport parameters of the analyte molecule.

Example 2

An empirical model for predicting nanopore transport and signaling phenomena has been developed based on measurements of multiple electrical signals in a solid-state nanopore device. With this model, it is shown that the ionic current and double layer potential from the nanopore are related conveniently to the size, charge, concentration and mobility of translocating ionic and molecular species in electrolytic solution. With such relationships defined, this model allows quick interpretation and prediction of the behavior of a nanopore system and provides a method for quantitative prediction of the properties of analytes. As a demonstration of the quantitative capability of this method, properties of nanoceria are predicted in a range of oxidative solutions and compared to predictions from physicochemical characterization methods.

When a translocating analyte in a supporting electrolyte passes through the EDL within the nanopore, the resulting ionic current and double layer potential signal must be dictated by the size and charge of the transporting species, particularly when the analyte diameter is smaller than the nanopore diameter and wall interactions are not expected to dominate translocation characteristics. Since translocation through the nanopore considered in this study is hindered due to a gating effect, analyte dwell times are often in the range of milliseconds and easily resolved by conventional electronics.

To capture the crucial underlying physics with a simplified model would provide significant assistance in the design of nanofluidic devices and analysis of molecular analytes. To realize this, we developed a model based on properties of the supporting electrolyte solution and nanopore geometry. This model will enable convenient and quantitative prediction of the behavior of such nanofluidic devices and the associated molecular signals. Particularly, it will allow the ionic current, double layer potential, and nanopore structure to be related to the transporting species, their valence charge, and solution strength. With this model, one can interpret and predict the behavior of a nanopore system based on experimental conditions alone, hence accelerating practical applications of the nanopore technology.

cally NaF) was driven through the nanopore, the corresponding ionic current was registered as the baseline ionic current ($I_{bs}$) and the EDL potential as the baseline EDL potential ($V_{bs}$). When the supporting electrolyte solutions also contained analyte molecules as highlighted in FIG. 1b, the translocation of a single analyte molecule through the nanopore would cause spike signals to occur simultaneously

TABLE 5

Terminology used in Example 2

| Symbol | Description | Unit |
|---|---|---|
| $a_{nanopore}$ | Activity of solution within the nanopore | Mole L$^{-1}$ |
| $a_{reservoir}$ | Activity of solution within the reservoir | Mole L$^{-1}$ |
| A | Cross sectional area of the nanopore | m$^2$ |
| $c_i$ | Concentration of species i | Mole L$^{-1}$ |
| $C_{EDL}$ | Double layer capacitance | F |
| D | Diffusion coefficient | m$^2$ s$^{-1}$ |
| $D_{Kn}$ | Knudsen diffusion coefficient | m$^2$ s$^{-1}$ |
| E | Electron charge | C |
| $\varepsilon$ | Permittivity | F m$^{-1}$ |
| E | Driving electric field | V m$^{-1}$ |
| $f_a^i$ | Activity coefficient of species i in solution | 1 |
| F | Faraday's constant | C mole$^{-1}$ |
| $I_{analyte}$ | Ionic current due to the analyte | A |
| $I_{ps}$ | Ionic current signal | A |
| $I_{ps\_total}$ | Total ionic current during translocation (baseline and signal) | A |
| $I_{bs}$ | Baseline ionic current | A |
| $\Delta I_{bs}$ | Change to the current carried by the supporting electrolyte | A |
| $k_B$ | Boltzmann's constant | m$^2$ kg s$^{-2}$ K$^{-1}$ |
| L | Length of the nanopore | m |
| $L_{Au}$ | Length of the metal layer in the nanopore | m |
| $\mu$ | Mobility | m$^2$v$^{-1}$ s$^{-1}$ |
| $\mu_{ion}$ | Mobility of the majority ion within the nanopore | m$^2$v$^{-1}$ s$^{-1}$ |
| $n_{analyte}$ | Charge density of the analyte | C m$^{-3}$ |
| $n_{bs}$ | Baseline charge density within the nanopore | C m$^{-3}$ |
| $\Delta n_{bs}$ | Change to the charge density in the supporting electrolyte | C m$^{-3}$ |
| $\Delta n_{bsE}$ | Change in charge density due to the charge of the analyte | C m$^{-3}$ |
| $\Delta n_{bsV}$ | Change in charge density due to the volume of the analyte | C m$^{-3}$ |
| $N_{Av}$ | Avogadro's number | Mole$^{-1}$ |
| $P_{bs}$ | Partition coefficient | 1 |
| r | Ionic radius | m |
| $r_m$ | Ionic radius of majority ion | m |
| $r_{analyte}$ | Ionic radius of analyte particle | m |
| $r_F$ | Ionic radius of Fluoride ion | m |
| $r_K$ | Ionic radius of Potassium ion | m |
| $r_{Stokes}$ | Stokes radius of analyte particle | m |
| R | Gas constant | J K$^{-1}$mole$^{-1}$ |
| T | Temperature | K |
| $t_{dl}$ | Translocation time measured in the double layer potential signal | s |
| $t_{ic}$ | Translocation time measured in the ionic current signal | s |
| $V_{analyte}$ | Volume of the analyte | m$^3$ |
| $\vec{v}_{analyte}$ | Drift velocity of the analyte | m s$^{-1}$ |
| $V_{dl}$ | Double layer potential signal | V |
| $V_{bs}$ | Baseline double layer potential | V |
| $\vec{v}_{bs}$ | Baseline drift velocity within the nanopore | m s$^{-1}$ |
| $\Delta \vec{v}_{bs}$ | Change to the drift velocity in the supporting electrolyte | m s$^{-1}$ |
| $V_{supp}$ | Volt-clamp potential | V |
| $V_{total}$ | Volume inside the nanopore | m$^3$ |
| X | Inverse Debye length | m$^{-1}$ |
| $Z_{analyte}$ | Valence charge of the analyte | 1 |
| $z_i$ | Valence charge of species i | 1 |
| $Z_{bs}$ | Baseline majority ion valence | 1 |

Methods

Experimental System:

The design and fabrication of a solid-state nanopore device, the experimental apparatus, and the signal extraction algorithms have been discussed in detail in our previous work. In brief, a nanopore with a radius of 1.6 nm was formed in a supporting layer of silicon nitride (50 nm thick) and a conducting metal layer of gold (5 nm thick). During experiments, the metal layer was charged with a small constant electrical current ($I_{supp}$=37.4±3.2 pA). As depicted in FIG. 1a, when an aqueous supporting electrolyte (typiin both the ionic current and EDL potential and these signals were regarded as the perturbed ionic current and EDL potential, or $I_{ps}$ and $V_{ps}$, respectively. In order to further characterize the detected spike signals, the translocation times of analytes ($t_{ic}$) were also determined as the full duration at half maximum (FDHM) of the ionic current signals.

Measurements were first made for baseline $I_{bs}$ and $V_{bs}$ in solution containing either NaF, KCl, NaCl, LiF, or a mixture of NaF and KCl as supporting electrolyte(s), each within a concentration range from 10$^{-7}$ M to 10$^{-1}$ M with logarithmic increments. Then measurements for perturbed $I_{ps}$ and $V_{ps}$ along with the associated translocation times ($t_{tc}$) were made for four well-characterized small molecule analytes, namely, citric acid, ascorbic acid, oxalic acid, and hydroquinone, at 10 nM in a supporting electrolyte solution of NaF with concentration of $10^{-7}$ M to 1 M in logarithmic increments.

Aside from measuring the baseline and perturbed signals using the above described electrolytes, colloidal solutions of nanocrystalline cerium dioxide ($CeO_2$) with two particle sizes were also considered. The samples were synthesized according to the protocol adapted from elsewhere. Briefly, aqueous solutions of cerium (III) nitrate with different concentrations (0.1-0.5 M) were mixed with citric acid, and added dropwise to 3M ammonia solution under constant stirring. The resulting purple suspension that corresponds to the formation of $(Ce^{+3},Ce^{+4})O_y(OH)z$ was kept at room temperature for 2 hours to facilitate oxidation and, thus, formation of $CeO_2$ (ceria). The obtained samples were rinsed several times with deionized water to remove an excess of ammonia and ammonium citrate. Ceria particle size was determined by means of dynamic light scattering (DLS) (Brookhaven 90 plus, Holtsville, N.Y.). Two ceria samples were chosen to be analyzed in the present study: 1) the first samples with the relatively small nanoparticles (1-1.5 nm), 2) the second sample with larger particles (2-3 nm).

Prior to the analysis with the nanopore, the ceria stock solutions were diluted to a final concentration of 20 µM in 1 mM NaF at pH 2.1, titrated with concentrated hydrochloric acid. Since redox properties of cerium oxide vary depending on the surrounding medium, the altered oxidized states of the nanoparticles were also evaluated after adding either microliter quantities of hydrogen peroxide solution (0.044 M $H_2O_2$) or ammonium hydroxide solution (0.044 M $NH_4OH$) to 10 ml aliquots of prepared nanoparticle solution.

Molecular Dynamics Study of the Size Selection Effect in the Baseline-State:

An MD study was performed to explore the relationship between supporting ion size and baseline measurements (double layer potential and ionic current) as well as to visualize the process of ions entering the nanopore. In the MD study four situations were considered: NaF and KCl solutions in a gold nanopore that is either neutral or partially charged. For the partially charged cases, a valence charge of 0.2 was imposed to each gold atom. Note that imposing this partial charge larger than expected was for accelerating the immediate effect on the passage of ions through the nanopore.

Figure 7A:
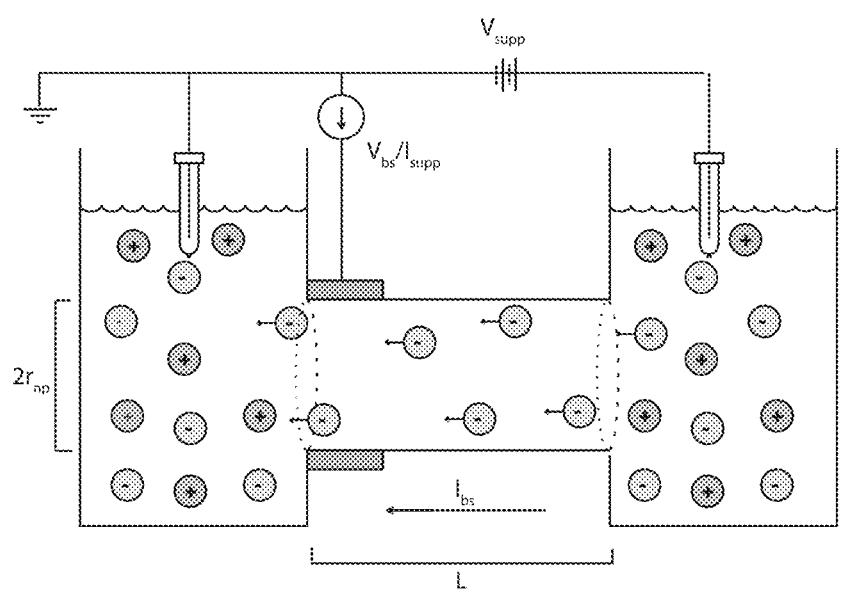
FIG. 7A A diagram of the nanopore in baseline conditions, for illustrative purposes drawing is not to scale. The net charge within the nanopore has a polarity opposite of the nanopore surface potential and has a given charge density and average drift velocity. The double layer potential is measured at the gold ring electrode around the nanopore ($V_{bs}$, grey block), while the ionic current ($I_{bs}$) is measured through the nanopore. A supporting, constant cross-pore potential is applied ($V_{supp}$) in order to measure the ionic current. A small electrical current is supplied to the gold ring electrode ($I_{supp}$), and the double layer charging potential ($V_{bs}$) is measured. The nanopore is fabricated with a given length (L) and cross-sectional area ($A=\pi r_{np}^2$)

The molecular model of the gold surface was constructed using the Avogadro program.[20] A square-shaped unit cell in x-y plane approximately 80 Å on each side (x and y directions) and 18 Å thick (z direction) was generated. A channel with radius of ~10 Å in the center of the x-y plane along the z-axis was created by removing Au atoms to mimic experimental conditions (FIG. 7c). CHARMM simulation program[21] was used for further model construction and simulations. The CHARMM22 protein force field[22] was used for the aqueous solution phase of the system (water and ions) and metal force field[23] was used for the atoms of gold. A large water box was initially equilibrated at 1 atm pressure and 298 K temperature in NPT ensemble for 1.0 ns using the leapfrog integrator. The gold surface slab was then placed in the middle of the equilibrated water box. The water box was sliced to fit the size of the gold surface in the x-y plane, leaving 17 Å solution layer on each side of the surface in z-direction to contain water and ions. To simulate the experimental solution concentration of 100 mM, 81 molecules of salt ($Na^+$ or $K^+$ and $F^-$ or $Cl^-$, respectively) were then added to the water phase by randomly replacing water molecules with the FIG. 7d).

Three dimensional periodic boundary conditions were applied during the simulations. The system was minimized using the steepest decent algorithm (first the gold surface keeping the solution phase constrained, then the solution phase locking the material surface). Then the gold atoms were constrained and the rest of the system was equilibrated. MD production runs were performed in the canonical ensemble using the modified velocity-Verlet integrator[24] and a Nosé-Hoover thermostat.[25] Van der Waals (vdW) interactions were represented by 12-6 Lennard-Jones potential with a group-based force-switched cutoff, while the Coulombic interactions were represented using a group-based force-shift cutoff. For both of the nonbonded interactions the cutoff started at 8 Å and ended at 12 Å with a pair-list generation at 14 Å. SHAKE algorithm[26] was used to constrain the hydrogen bonds which enabled MD simulations with 2 fs timestep. For each system, simulation was performed for 2 ns and the frames were saved every 5 ps to monitor the entrance and behavior of the ions in the nanopore.

Empirical Model Based on Experimental Observations

Empirical Relationships of the Baseline-State:

The baseline-state double layer potentials and ionic currents in various supporting electrolytes decrease in magnitude as the concentration of the supporting electrolyte increases and may have positive or negative polarity (FIG. 8a,b). We observe a selection effect due to a supporting electrolyte in the baseline-state potentials as seen in FIG. 8a and baseline-state ionic currents as seen in FIG. 8b. By considering activities of several electrolyte solutions (NaF, KCl, NaCl, LiF, or a mixture of NaF and KCl) and iteratively fitting experimentally observed baseline potentials, a relationship for the baseline double layer potential is calculated through the following equation:

$$V_{bs} = -\text{sgn}(z_{bs})P_{bs}\frac{RT}{F}\frac{a_{reservoir}}{a_{nanopore}} \quad (1)$$

where R is the gas constant, T is the temperature, F is Faraday's constant, $z_{bs}$ is the valence of the majority ion within the nanopore, a is activity which can be found as $a=cf_a$ in which c is the solution concentration, and $P_{bs}$ is a baseline partition coefficient that is dependent on the supporting electrolyte and nanopore radius. The sign function (sgn) returns the polarity (1 or −1) of the argument. A negative sign is included in Equation 1 because it is observed that the surface potential has polarity opposite of the majority ion within the nanopore. The difference in the baseline-states when different supporting electrolytes are considered arises from differences in the molecular weight or size of the supporting ions, where molecular weight and size are correlated.

The measured baseline double layer potential is linearly related to the baseline ionic current, both of which increase in magnitude with nanopore size and solution concentration (FIG. 8c). From experimental observation of the baseline-state in different sized nanopores ($r_{np}$=1.7, 2.3, and 4.0 nm) and solutions of varying concentration ($10^{-7}$ M to 1 M), it is noted that the baseline ionic current ($I_{bs}$) seems to be related to the baseline double layer potential ($V_{bs}$) in a linear relationship ($R^2$=0.9735 in units of volts and amperes):

$$I_{bs}=10^{-8}V_{bs}-4.8 \cdot 10^{-10} \quad (2)$$

The baseline-state current and potential as calculated from equations 1 and 2 is shown in FIG. 8d and demonstrates the same dependence on concentration and nanopore radius as seen in the experimental measurements of FIG. 8c. The baseline double layer potential and baseline ionic current as predicted from the empirical model (equations 1 and 2, respectively) closely follow the experimental measurements.

Activity in Equation 1 can be determined from concentration and activity coefficient, where the activity coefficient is determined using Debye's method as a function of the concentration, ionic radius, and valence charge of the ions in the solution:[27,28]

$$\ln(f_a) = -0.849 z_i^2 \sqrt{\Sigma c_i z_i^2} \frac{1}{1 + 0.235 r \sqrt{\Sigma c_i z_i^2}} \quad (3)$$

where $f_a$ is the activity coefficient of the solution at room temperature, r is the average ion radius, $z_i$ and $c_i$ are valence charge and concentration of species i, respectively. The activity in the nanopore ($a_{nanopore}$) is calculated from the activities of the majority ions within the nanopore (considering only the positive or only the negative ions), whereas the activity in the reservoir ($a_{reservoir}$) accounts for all ions in solution. The partition coefficient ($P_{bs}$) in Equation (1) is defined as a unitless coefficient $$P_{bs} = \frac{D_{Kn,b}}{D_{Kn,a}} \frac{r_{np}}{L_C},$$

where $D_{Kn,a}$ is the Knudsen diffusion coefficient $$\left( D_{Kn} = \frac{2 r_{np}}{3} \sqrt{\frac{8 k_B T}{\pi M_w}} \right)$$

of the majority ion within the nanopore, $D_{Kn,b}$ is the Knudsen diffusion coefficient of the minority ion within the nanopore, $r_{np}$ is the radius of the nanopore, $k_B$ is Boltzmann's constant, and $L_C$ is the characteristic length scale of the system, which is taken as 1 nm in this study. Since particle size tends to correlate to molecular weight, it is expected that this ratio of Knudsen diffusion coefficients should also be proportional to the ratio of ionic radii in an electrolyte pair:

$$\frac{D_{K,b}}{D_{K,a}} \propto \left( \frac{M_{w,a}}{M_{w,b}} \right)^{0.5} \propto \left( \frac{r_a}{r_b} \right)^{1.5}.$$

The dependence on the relative size of the supporting ions is consistent with the observation that the majority ion in the nanopore was consistently the smaller of the ions in the supporting electrolyte pair. The electrolyte dependence in FIGS. 8a and 8b indicate that including the ratio Knudsen diffusion coefficients in the partition coefficient holds for many salts and concentrations by considering measurements from several different electrolytes (NaF, KCl, NaCl, LiF, and NaF+KCl mixtures, FIG. 8a, b. In mixtures of monovalent electrolytes, $$P_{bs} = \prod_i P_i$$

which is a general expression for mixtures as well as single salt solutions. Should the influence of supporting ion size in the partition coefficient ($P_{bs}$) be neglected (as in $$P_{bs} = \frac{r_{np}}{L_C} \Bigg),$$

for all electrolytes the predicted baseline-state values of the surface potentials and ionic currents would have similar magnitudes and be perfectly symmetrical around 0V. The baseline double layer potential appears to be due in part to a size selection against larger ions in the nanopore, where larger ions are restricted from entering the nanopore compared to smaller ions. In order to investigate, an MD model is considered to observe the size selection effect.

Figure 9C:
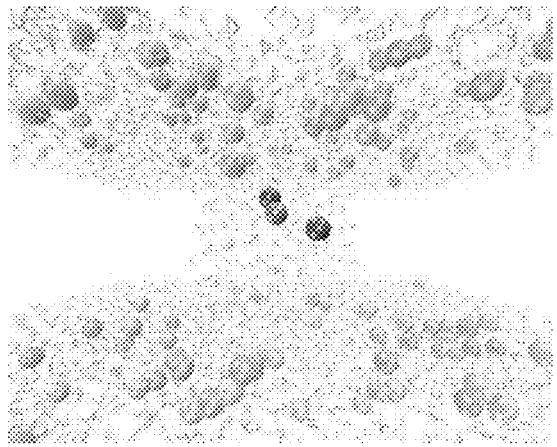
FIG. 9C Because the ions in KCl solution are of approximately similar size, the size selection has little effect in a neutral nanopore. $K^+$ ions are shown in tan and $Cl^-$ ions are shown in blue.
Figure 9D:
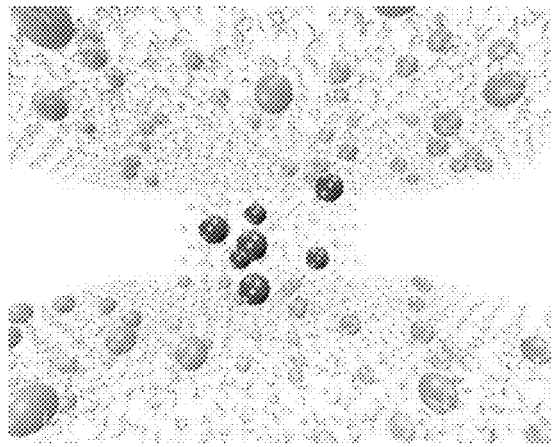
FIG. 9D In the negatively charged gold nanopore, the positive ion is selectively introduced into the nanopore, indicating that there is an electrostatic selection effect that occurs when the size selection effect is weak due to the similar sizes of the ions.

Molecular Dynamics Results:

The molecular dynamic (MD) results indicate that a size selection effect is strongest when there is a large difference in the size of cations and anions, but when the sizes are similar, additional electrical effects can contribute to the separation of ions, preferentially introducing cations into the nanopore (FIG. 9). In the MD model containing NaF in an uncharged nanopore, Fluoride ($F^-$) clearly enters the nanopore first and exclusively, since there is a large size difference between the ions (FIG. 9a). When a strong negative charge is applied to the nanopore in NaF solution, the positive Sodium ($Na^+$) ions make up the charge within the nanopore due to electrostatic interaction (FIG. 9b) which is dissimilar to the experimental measurement and arises because of the artificially fixed charge distribution in simulation. When considering KCl in an uncharged nanopore, both ions enter the nanopore at the similar rates because the ions are very similar in size and there is no electrostatic selection (FIG. 9c). As with the charged NaF model, when a charged nanopore is evaluated with KCl solution, the positive ion makes up the majority of the charge due to electrostatic interactions (FIG. 9d) which is consistent with the expectation that the majority ion is a cation in KCl solution. From these simulations, it can be seen qualitatively that when ionic radii of the supporting electrolyte are sufficiently different, the smaller ion enters the nanopore first, inducing the nanopore surface to carry a potential of opposite polarity which continues charging until equilibrium is reached. When the ions are similar in size, there must be an initial electrostatic effect that selects for positive ion polarity before charging to the equilibrium potential. However, to be consistent with experimental observation, the electrostatic selection effect must be considerably weaker than the size selection effect. These results are in line with the trends observed in the experimental data, where the smaller supporting ion typically has opposite polarity to the baseline surface potential (FIG. 9a).

Further Predictions Based on the Empirical Relationships
Baseline-State:

In the baseline-state, the ionic current ($I_{bs}$) described empirically by Equation 2 can also be expressed in terms of the velocity and density of the charges moving through the cross section of the nanopore (FIG. 7a):

$$I_{bs} = \text{sgn}(z_{bs}) n_{bs} A \vec{v}_{bs} \quad (4)$$

where $n_{bs}$ is the net charge density within the nanopore (in units of C/m³), A is the cross-sectional area of the nanopore, and $\vec{v}_{bs}$ is the drift velocity of the net charge. The drift velocity of the supporting charges ($\vec{v}_{bs}$) can be determined from the electric field across the nanopore and the mobility of the majority ion:

$$\vec{v}_{bs} = -\text{sgn}(z_{bs})\mu_{ion}EF \tag{5}$$

where $\mu_{ion}$ is the mobility of the supporting ion and E is the electric field which is considered as the baseline potential over the length of the metal layer ($E = V_{bs}/L_{Au}$).

With Equations 2 and 4, the charge density ($n_{bs}$) within the nanopore can be determined as:

$$n_{bs} = \text{sgn}(z_{bs})\frac{V_{bs} - 0.048}{10^8 A \vec{v}_{bs}} \tag{6}$$

Since both drift velocity ($\vec{v}_{bs}$) and charge density ($n_{bs}$) are functions of $V_{bs}$, which is in turn a function of activity, one can relate the baseline-state ionic current to experimental conditions through the solution activity by substituting Equations 5 and 6 into Equation 4.

The capacitance of the electrical double layer can be found as the derivative of baseline charge in the nanopore (baseline charge is the product of the nanopore volume and charge density, $V_{total}n_{bs}$) with respect to the double layer potential:

$$C_{EDL} = V_{total}\frac{\delta n_{bs}}{\delta V_{bs}} \tag{7}$$

Perturbed-State:

When an analyte translocates the nanopore inducing the perturbed-state, the total change to the charge density of the supporting ions within the nanopore is due to the summation of volumetric and electrical interactions between the analyte and supporting solution:

$$\Delta n_{bs} = \Delta n_{bsV} + \Delta n_{bsE} \tag{8}$$

The charge density of the supporting electrolyte is altered by partial occlusion of the nanopore by the analyte molecule and compensatory charge accumulation due to electrostatic interaction with the valence charge of the analyte. The volume exclusion is known as the blockade effect and is commonly considered the primary source of the ionic current signal in nanopores. The change in charge density due to analyte volume was calculated by considering the amount of baseline charge that must be displaced:

$$\Delta n_{bsV} = -\frac{n_{bs}V_{analyte}}{V_{total}} \tag{9}$$

In this case, the volume of the analyte ($V_{analyte}$) occludes a portion of the total nanopore volume, and the total charge within the nanopore is reduced by the amount of supporting charge that occupied the analyte volume in the baseline-state. The analyte volume is calculated in this study as a sphere $$\left(V_{analyte} = \frac{4}{3}\pi r_{Stokes}^3\right)$$

with the radius ($r_{stokes}$) defined as the average radius of the analyte ($r_{analyte}$) with a water layer (Stokes radius).

The charge density within the nanopore is also altered by electrical interactions with the analyte molecule, where supporting ions are either attracted or repelled by the valence charge of the analyte:

$$\Delta n_{bsE} = -\frac{z_{analyte}e}{V_{total}} \tag{10}$$

A number of charges proportional to valence and with polarity opposite to that of the analyte will be accumulated within the nanopore due to the charge of the analyte. Alternatively and equivalently, one could consider $\Delta n_{bsE}$ as due to charges of the same polarity as the analyte being repelled.

The change in supporting ion drift velocity ($\Delta \vec{v}_{bs}$) was calculated from Equation 6 with consideration of the perturbed-state charge density ($n_{ps} = n_{bs} + \Delta n_{bs}$) and drift velocity ($\vec{v}_{ps} = \vec{v}_{bs} + \Delta \vec{v}_{bs}$):

$$\Delta \vec{v}_{bs} = \frac{\text{sgn}(z_{bs})(V_{bs} - 0.048)}{10^8 A(n_{bs} + \Delta n_{bs})} - \vec{v}_{bs} \tag{11}$$

It should be noted that both the change in charge density ($\Delta n_{bs}$) and change in velocity ($\Delta \vec{v}_{bs}$) are dependent on the baseline conditions ($n_{bs}$ and $\vec{v}_{bs}$), indicating that the magnitude of the molecular signals are modulated by the baseline-state.

FIG. 10 shows the baseline and perturbed supporting charge density ($n_{bs}$, $\Delta n_{bs}$) and drift velocity ($\vec{v}_{bs}$, $\Delta \vec{v}_{bs}$) as predicted by this model. These predictions are included to illustrate the internal conditions of the model linking the perturbed-state signals to the baseline-state and to discuss the limitations of this model. The predicted baseline drift velocity ($\vec{v}_{bs}$) and charge density ($n_{bs}$) are considered to have uniform distributions within the nanopore, despite the fact that the drift velocity is due to a combination of electrophoretic, electroosmotic, and diffusive transport mechanisms and that the charge distribution is known to have a non-uniform distribution in the EDL. While these predicted values are internally consistent with the model developed in this study, they are not necessarily intended to be interpreted as strictly valid from a physical point of view.

At high concentrations, the magnitude of the net density of charges ($n_{bs}$, FIG. 10a) increases, while the magnitude of the drift velocity ($\vec{v}_{bs}$, Figure b) decreases, resulting in the overall decrease in magnitude of the ionic current and double layer potential in the baseline-state ($I_{bs}$ and $V_{bs}$, respectively). The baseline drift velocity ($\vec{v}_{bs}$, FIG. 10b) is negative, which is consistent with the polarity of the driving electric field associated with both positive and negative ions in our spatial reference frame. The drift velocity ($\vec{v}_{bs}$) and charge density ($n_{bs}$) are dependent on the size of the majority ion (via the partition coefficient, $P_{bs}$) and the driving potential ($V_{bs}$).

Figure 10A:
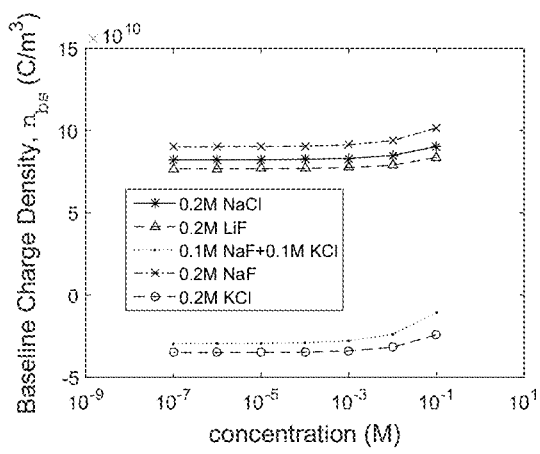
FIG. 10A The charge density within the nanopore predicted as a function of the concentration of the supporting electrolyte.
Figure 10B:
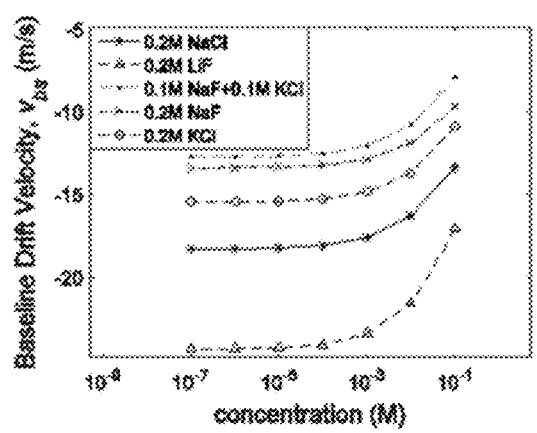
FIG. 10B The average drift velocity of the supporting ionic current predicted as a function of the concentration of the supporting electrolyte.
Figure 10C:
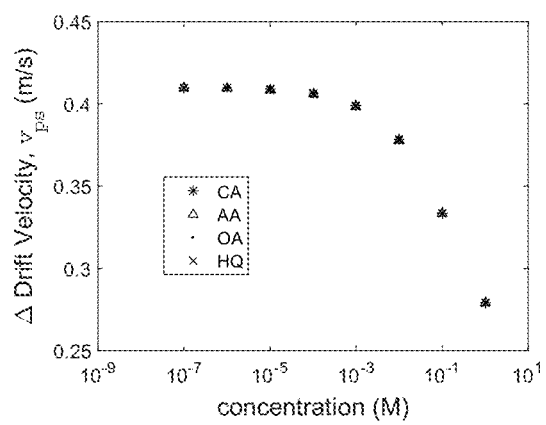
FIG. 10C The change to the supporting ion drift velocity due to the analyte molecule predicted in this model.
Figure 10D:
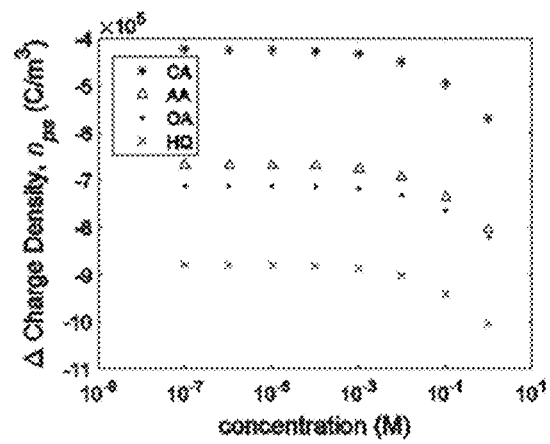
FIG. 10D The change to the supporting electrolyte charge density within the nanopore predicted to be due to the analyte molecule.

The change in velocity ($\Delta \vec{v}_{bs}$) and charge density ($\Delta n_{bs}$) in the perturbed-state are both small compared to the baseline drift velocity ($\vec{v}_{bs}$) and charge density ($n_{bs}$), respectively (FIG. 10c,d). While the change to the supporting electrolyte velocity ($\Delta \vec{v}_{bs}$) has relatively large magnitude at low concentrations, the change in velocity itself does not contribute much to the difference between analyte signals (FIG. 10c). Rather, the change to the drift velocity acts ($\Delta \vec{v}_{bs}$) as a multiplier to enhance the effects of the change in supporting charge density ($\Delta n_{bs}$) in the ionic current signal ($I_{ps}$, see Equation 15). The change in supporting charge density in the perturbed-state ($\Delta n_{bs}$) tends to increase proportionally to the valence of the analyte, indicating that the charge accumulation effect ($\Delta n_{bsE}$) is primarily responsible for the differences between analyte signals (FIG. 10d).

Linking Ionic Current Signal to Analyte Species:

In the perturbed-state (FIG. 1c), where a single analyte molecule passes through the nanopore, spike signals are experimentally observed in the ionic current and double layer potential. The magnitudes of the spike signals measured from respective baselines are expected to be related to the size and charge of the analyte. The direct contribution of the analyte to molecular signals ($I_{ps}$ and $V_{ps}$) may be considered separately from the effect of the analyte on the baseline charge density and velocity. To show the method of calculating the direct contribution of the analyte on the ionic current signal ($I_{ps}$), the analyte ionic current signal is considered as due to the charge density and drift velocity of the analyte. The ionic current due to the direct contribution of the analyte is described with a form similar to the baseline ionic current (Equation 4):

$$I_{analyte} = \text{sgn}(z_{analyte}) n_{analyte} \vec{v}_{analyte} A \quad (12)$$

where the valence charge of the analyte ($z_{analyte}$) and nanopore cross-sectional area (A) are considered as known quantities. By considering the analyte as a single charged particle within the nanopore, the analyte charge density ($n_{analyte}$) is calculate as:

$$n_{analyte} = \frac{z_{analyte} e}{V_{total}} \quad (13)$$

The four analytes evaluated in the development of this model (Citric Acid, Ascorbic Acid, Oxalic Acid, and Hydroquinone) exhibit only three valence charge levels, $Z_{analyte}=-3, -2, -1, -1$, respectively, and therefore only produce three distinct charge densities. The drift velocity of the analytes is calculated directly by dividing the total length of the nanopore (L=55 nm) by the translocation times measured as full duration at half maximum (FDHM) of the ionic current signal:

$$\vec{v}_{analyte} = -\frac{L}{t_{IC}} \quad (14)$$

The analyte contribution to the ionic current signal (Equation 12) is calculated from these values, which are found to be several orders of magnitude smaller than the total ionic current signal observed in experiment. The change in charge density due to the analyte valence charge ($n_{analyte}$) is relatively large and contributes to the double layer potential signal. However the analyte drift velocity ($\vec{v}_{analyte}$) is very small, and the product of drift velocity and analyte charge density in Equation 12 results in a negligible direct contribution to the ionic current signal ($I_{ps}$). Because the direct contribution of the analyte is orders of magnitude smaller than the detected ionic current signal, it is treated as negligible in this analysis and the ionic current signal ($I_{ps}$) is considered arising solely from the change to the supporting ionic current ($\Delta I_{bs}$). However, the charge density of the analyte ($n_{analyte}$) still contributes to the double layer potential signal and should not be neglected.

Molecular Signals in the Perturbed-State:

The perturbation of the ionic current (the ionic current signal) is governed by changes in the supporting electrolyte current ($\Delta I_{bs}$) caused by alteration of the supporting charge density ($\Delta n_{bs}$) and alterations to the velocity of the supporting charge ($\Delta \vec{v}_{bs}$) within the nanopore (FIG. 7b). The ionic current signal due to the changes in supporting electrolyte current is expressed with a modification to the form of Equation 4:

$$I_{ps} = \Delta I_{bs} = \text{sgn}(z_{bs}) \Delta n_{bs} \Delta \vec{v}_{bs} A \quad (15)$$

The perturbed double layer potential can be calculated from the capacitance of the electrical double layer and changes to the total charge in the nanopore as:

$$V_{ps} = \frac{V_{total}(\Delta n_{bs} + n_{analyte})}{C_{EDL}} \quad (16)$$

where $n_{analyte}$ is the charge density of the analyte within the nanopore.

Figure 11A:
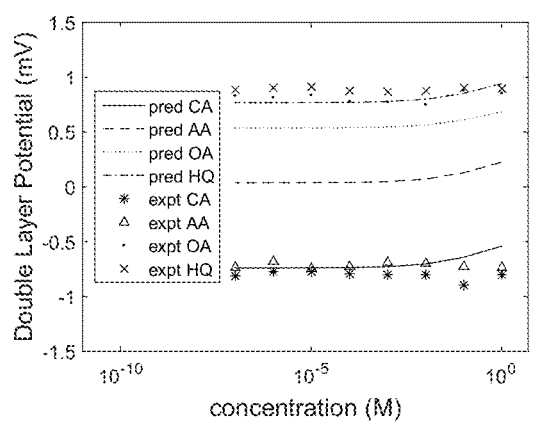
FIG. 11A Predicted double layer potential signal compared to experimental measure. Range, signal order, and magnitude are similar between predicted and experimental values.
Figure 11B:
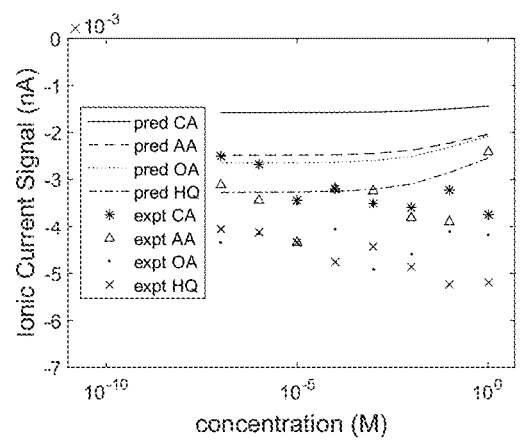
FIG. 11B The predicted ionic current signals compared with the measured ionic current signals for the four analytes used for validation. There are no clear trends in the ionic current signal, but the most negative experimental signals tend to come from hydroquinone and the most positive (closest to 0 nA) tend to be produced by citric acid in both the predicted and experimental results.

The predicted double layer potential signal ($V_{ps}$, FIG. 11a) and ionic current signal ($I_{ps}$, FIG. 11b) have similar trends and magnitudes to the measured values. The order of the signals in the double layer potential signal is consistent with experiment, with the most positive signals from Hydroquinone (HQ), smaller positive signal from Oxalic Acid (OA), small negative signal from Ascorbic Acid (AA), and most negative signal from Citric Acid (CA). The range of the predicted double layer potentials signals ($V_{ps}$) is similar to what is observed experimentally, falling between −1 mV and 1 mV in this device. While the trends in the measured ionic current signal are weak (FIG. 11b), hydroquinone tends to appear often in the most negative current signals and citric acid tends to produce signals with smaller negative magnitudes (this trend is reversed from the order of signals from the double layer potential). Comparing the predicted signals to the measured ionic current signals is problematic because of the lack of clear trends in the measurement, so the general trend was established while the predicted signals were close to the experimental range. Because of this difficulty, model validation relies much more heavily on the baseline ionic current ($I_{bs}$) and double layer potentials ($V_{bs}$), as well as the double layer potential signal ($V_{ps}$). The high level of variability in the ionic current signal ($I_{ps}$) may be the source of difficulty that has been encountered in developing nanopore sensors since the origination in 1998.

Resolving the Kinetic Parameters of the Analytes:

Taking advantage of measurements of translocation time ($t_{IC}$), Equation 5 is rearranged and the model definition of the driving electric field ($E=V_{bs}/L_{Au}$) is substituted to solve for the mobility of single molecules as a function of the translocation time and baseline double layer potential:

$$\mu = \frac{\vec{v}_{bs}}{EF} \quad (17)$$

which can be stated explicitly in terms of the baseline potential and translocation time as $$\mu = \frac{L^2}{V_{bs} F t_{lC}}.$$

From this calculated value for the mobility, the Stokes-Einstein relationship is employed to determine the corresponding diffusion coefficient, which is also a function of the analyte valence:

$$D = \frac{\mu k_B T N_{Av}}{z_{analyte}} \quad (18)$$

The magnitudes of these calculated values are independent of the double layer potential signal ($V_{ps}$) and ionic current signal ($I_{ps}$) magnitudes and may be useful as additional signals for identification of single molecule analytes.

Figure 12A:
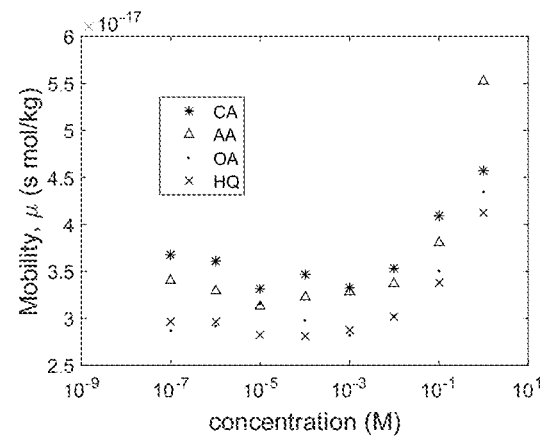
FIG. 12A includes a graph of mobilities and FIG. 12B includes a graph of diffusion coefficients of the analytes and ions are dependent on analyte species and orders of magnitude smaller than when measured in bulk solution. The low values are to be expected as the analytes are impeded in translocation by the size and charge selecting effects of the nanopore.
Figure 12B:
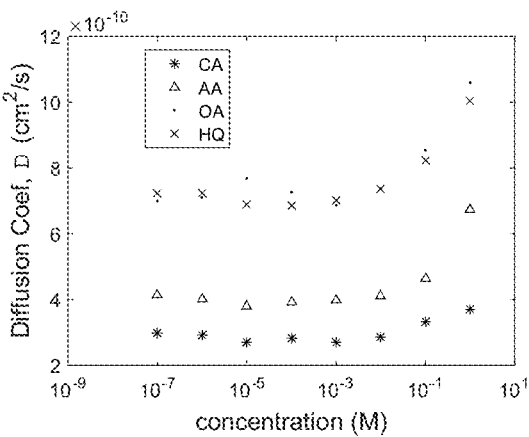

The values calculated for the mobilities (FIG. 12a) and diffusion coefficients (FIG. 12b) of the analyte molecules are 2 orders of magnitude smaller than is typically reported for these analytes in unconstrained volumes. However, it is not entirely surprising that the diffusion coefficients and mobilities are small, since the analytes must move through the charge and size selecting region of the nanopore which restricts freedom of movement. Separation of signals is more apparent in the diffusion coefficients than in the mobilities, but calculation of the diffusion coefficient requires knowledge of the valence charge of the analyte. However, even in the less pronounced signal separation observed in the mobility measurement, the signals from different analytes remain distinct in a wide range of supporting electrolyte concentrations. The mobility (which is calculated from experimental measurements of translocation time with no prior knowledge of the analyte valence charge, Equation 17), may be useful in identifying unknown analytes, especially when used alongside the ionic current and double layer potential signals.

Case Study: Predicting Cerium Oxide Nanoparticle Properties

In order to explore the capabilities of this model, properties of $CeO_2$ nanoparticles were predicted from experimental measurements. The small nanoparticle was evaluated in a nanopore with a radius of $r_{np}$=2.8 nm and the large nanoparticle in a nanopore with radius of $r_{np}$=4 nm, where the nanopore radii were determined by fitting the model to the baseline ionic current and double layer potentials. The predicted ionic current ($I_{ps}$) and double layer potential ($V_{ps}$) signals were fitted to the measured ionic current and double layer potential signals for Cerium Oxide nanoparticles by adjusting the expected values for analyte radius ($r_{analyte}$) and analyte charge ($z_{analyte}$) while the solution composition and nanopore geometry were matched to experimental conditions.

Prior to conducting nanopore measurements, the obtained ceria samples were characterized using a set of physicochemical techniques. The results are presented in Table 6.

TABLE 6

Physicochemical characteristics of the studied ceria samples

| | Particle radius, nm | |
|---|---|---|
| Sample | DLS | TEM |
| «Small» | 1.2 ± 0.2 | 1.7 ± 0.2 |
| «Large» | 2.3 ± 0.8 | 3.5 ± 0.4 |

The results suggest significant difference in particle sizes when comparing two ceria samples as measured by DLS and TEM ($p<0.05$).

Figure 13A:
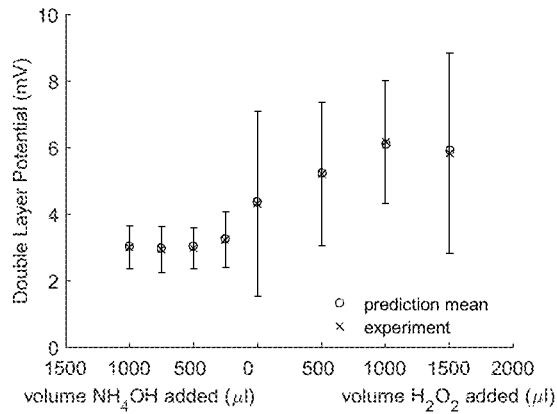
FIG. 13A The double layer potential signal from the small Cerium Oxide nanoparticle from a 2.3 nm radius nanopore in various concentrations of either ammonium hydroxide ($NH_4OH$) or hydrogen peroxide ($H_2O_2$). The predicted signal was made to closely match the observed signal by altering the predicted nanoparticle radius and charge in the model.
Figure 13B:
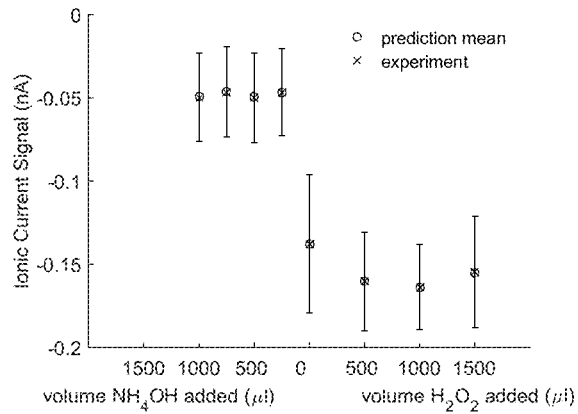
FIG. 13B The ionic current signal for the small Cerium Oxide nanoparticle that was obtained simultaneously with the double layer potential signal and fitted by the model in the same way.
Figure 13C:
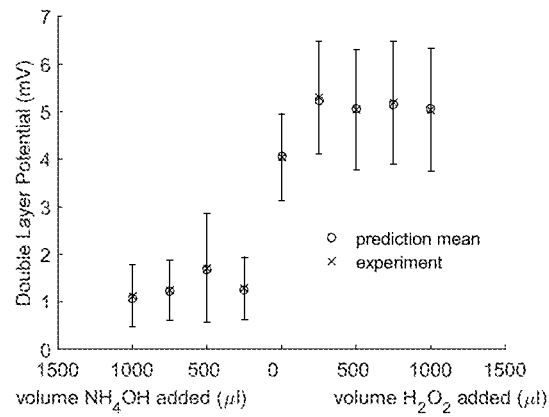
FIG. 13C The double layer potential signal from the large Cerium Oxide nanoparticle from a 4 nm radius nanopore in various concentrations of either ammonium hydroxide ($NH_4OH$) or hydrogen peroxide ($H_2O_2$). The predicted signal was fit to the experiment by adjusting the expected nanoparticle radius and charge.
Figure 13D:
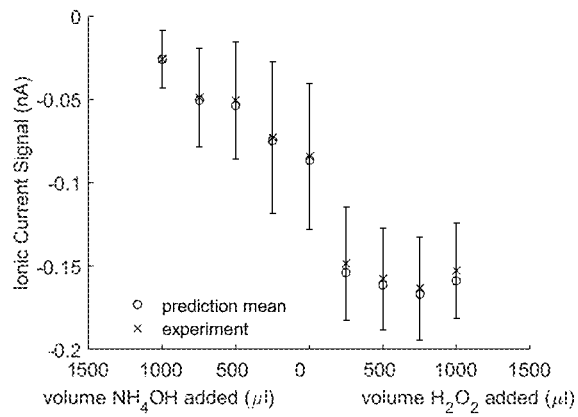
FIG. 13D The ionic current signal for the large Cerium Oxide nanoparticle that was obtained simultaneously with the double layer potential signal and fitted by the model in the same way.

The predicted double layer potential signals ($V_{ps}$) and ionic current signals ($I_{ps}$) of both the small (1-1.5 nm radius, FIG. 13a,b) and larger (2-3 nm radius, FIG. 13c,d) cerium oxide nanoparticles match the experimentally measured signals. The double layer potential signals of both nanoparticles (FIG. 13a,c) increase with addition of $H_2O_2$ and quickly reach a maximum level, while addition of $NH_4OH$ results in a decrease in signal magnitude to a minimum level. The ionic current signals of both nanoparticles (FIG. 13b,d) have the opposite relationship to the added reagents, decreasing in value with $H_2O_2$ and increasing with $NH_4OH$.

Figure 13E:
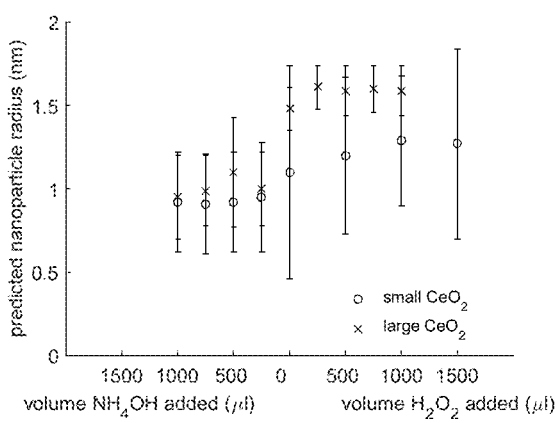
FIG. 13E The radius of the Cerium Oxide nanoparticles predicted from the model appears to increase with additional oxidizing agent and falls within the expected range of nanoparticle radii. The radius of the small Cerium Oxide nanoparticle predicted from the model appears to increase with additional oxidizing agent but is smaller than expected based on DLS and TEM measurements.

The radius of the small nanoparticle is predicted to be between 0.92 nm (1.84 nm diameter) in $NH_4OH$ and 1.27 nm (2.54 nm diameter) in $H_2O_2$, which is consistent with the expected size of these nanoparticles (FIG. 13e). The radius is predicted to increase by 0.35 nm, which could be due to the formation of ceria-peroxo complexes on the particle surface. Moreover, an increase in particle size can be caused by the partial reduction of $Ce^{4+}$ to $Ce^{3+}$. The latter ions possess substantially higher ionic radius, which affects lattice parameter of the compound, leading to the particle size increase.

The predicted charge associated with the small nanoparticle (FIG. 13f) varies between $z_{analyte}$=28 in $NH_4OH$ solution to $z_{analyte}$=112 in $H_2O_2$ solution. The increase in predicted charge is exactly 4× in the small nanoparticle, which is consistent with oxidation of exposed Cerium on the nanoparticle surface which carries a maximum charge of +4 per atom ($Ce^{+4}$). It is likely that the charge predicted by these measurements is primarily due to modification of surface charge, rather than changes to the crystalline structure of the nanoparticles. Another point to be discussed is that citrate ions that cover ceria nanoparticles are partially dissociated when exposed to the acidic environment ($H_2O_2$). This effect can also cause the change of surface charge measured in the present study. However, additional studies are required to determine the effect of citrate dissociation on surface charge alterations.

Figure 13F:
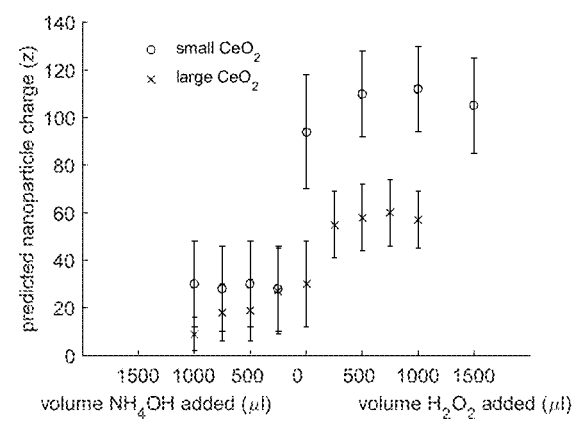
FIG. 13F The predicted charge of the Cerium Oxide nanoparticles with additional oxidizing agent with an increase of about 4× and corresponds to the expected maximum oxidation state of Cerium, which is +4.

The predicted nanoparticle radius for the larger nanoparticle in a 4 nm radius nanopore varies between 0.85 nm and 1.4 nm (1.7-2.8 nm diameter, FIG. 13e) and the predicted charge is between 8 and 51 (FIG. 13f). In the evaluation of the larger nanoparticle, rather than consider the Stokes radius of the particle in the calculation of the perturbed-state volume effect ($\Delta n_{bs}$, Equation 8), the analyte radius ($r_{analyte}$) without a water layer is considered. Considering the Stokes radius of this larger nanoparticle in a larger nanopore results in dramatic under-prediction of the nanoparticle size (0.15-0.7 nm radius) compared to the size estimated from dynamic light scattering. Two effects could result in the under-prediction of the size of this nanoparticle. Due to the increased radius of the nanoparticle, the water layer considered in the Stokes radius may be modified in such a way that it is no longer consistent with the assumptions of this model.

Additionally, within the larger nanopore the non-uniformity of the diffuse layer of the EDL will induce error in the calculation of the baseline charge density, where smaller nanopores should have a more uniform charge density ($n_{bs}$). Because of the simplifying assumptions of this model (small analytes, uniform charge density within the nanopore), predictions and applications may only be accurate for a narrow range of nanopore sizes (<4 nm radius). However, such limitations are not an unacceptable tradeoff given the simplicity of the model and the accuracy of the model within the limited scope.

A new method of modeling nanopore transport and signaling phenomena is developed from empirical nanopore behavior. It is shown that all interactions and measurements in a nanopore can be related as functions of the size, charge, and concentration of the ions and molecules in the supporting solution. By considering the electrophysical properties of an electrolyte solution, the interactions governing the steady state ionic current and double layer potential in a nanopore by way of the activity coefficient of the solution can be described. A basis for the ionic current and double layer potential signals can be formed by calculating changes to the steady state condition that must occur during the translocation of an analyte molecule. In this analysis, fundamental nanoscale properties of nanopore translocation are calculated from experimental measurements, including diffusion coefficients and mobilities in confined volumes, electrical interactions, and volumetric interactions. By taking this analytical and empirical approach to nanopore behavior, we demonstrate an analytical model of nanopore behavior from an empirical basis. When a group of substituents is disclosed herein, it is understood that all individual members of those groups and all subgroups and classes that can be formed using the substituents are disclosed separately. When a Markush group or other grouping is used herein, all individual members of the group and all combinations and subcombinations possible of the group are intended to be individually included in the disclosure.

Conclusion:

A set of empirical relationships were developed for elucidating the operational mechanisms of a nanopore fluidic device from experimental observations. These relationships have the capability to predict the ionic current and double layer potential signals of analyte species based on experimental conditions including size, charge, and solution strength of the supporting electrolyte. Moreover, the mobility and diffusion coefficients of analyte molecules were found to be quantifiable parameters to serve as additional molecular identifiers when interrogated by a nanopore. In demonstrating the newly developed molecular detection capabilities, quantitative predictions were made for the size and charge of the analyte.

The model developed here is powerful in that it allows for both the prediction of baseline-state behavior and molecular signals from arbitrary analytes in a given system and for quantitative prediction of analyte size and charge from simple experiments. No complex and resource heavy computation is needed to adapt this analytical model to a specific system. This is an improvement over many computational models, which allows for quick evaluation of experiments. This collection of relationships offers unique insight into the behavior of nanopore devices and relates all measurements and signals to the size, charge, and concentration of the supporting electrolytes and analyte ions.

Example 3

Improved molecular characterization from multi-signal combinations in a solid-state nanopore is described herein. With a ring-electrode nanopore, it is possible to collect multiple predictive signals from single molecule events. Mixtures of small molecules were analyzed and DNA fragments were sequenced in such a nanopore with measurements of ionic current, double layer potential, and mobility combined as composite signals. The characteristics of small molecules in mixtures were classified with a hierarchical clustering algorithm and found to be comparable to expected values. Short DNA segments were sequenced by training a hidden Markov model with the ionic current, double layer potential, or composite signals and expected sequences were accurately predicted from single molecule measurements. Considering multi-signal combinations increased the robustness of the nanopore sensor system against variation in the signal measurements. The accuracy of characteristic predictions was found to be highest when multiple nanopore signal-types were considered, while high precision predictions were obtained with the double layer potential signal alone.

Figure 14A:
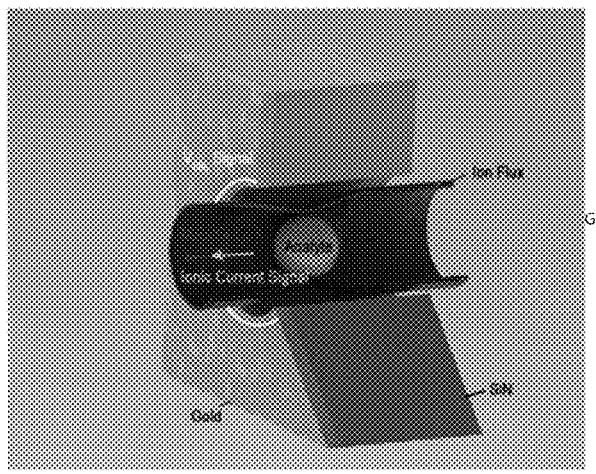
FIG. 14A A visualization of the nanopore, generic analyte, and three signals. The double layer potential signal ($V_{edl}$, yellow) is measured in changes to the charging potential of the gold ring electrode. The restriction of supporting ion flux as the analyte occludes the nanopore results in the ionic current signal ($I_c$, orange). The velocity of the translocating analyte is normalized to the driving electric field, allowing a single molecule mobility signal to be calculated ($\mu$, red).
Figure 14B:
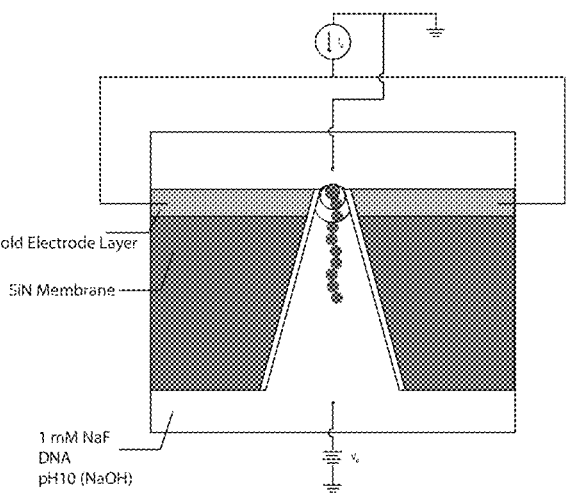
FIG. 14B A diagram of the experimental setup. The nanopore chip was placed between two fluid reservoirs containing the DNA analyte and a supporting electrolyte. A small current was supplied to the gold electrode of the nanopore while the potential between the reservoirs was held constant. The possibility that the nanopore would detect 1, 2, or 3 nucleotide segments of DNA as the strand translocated the nanopore was considered.
Figure 14C:
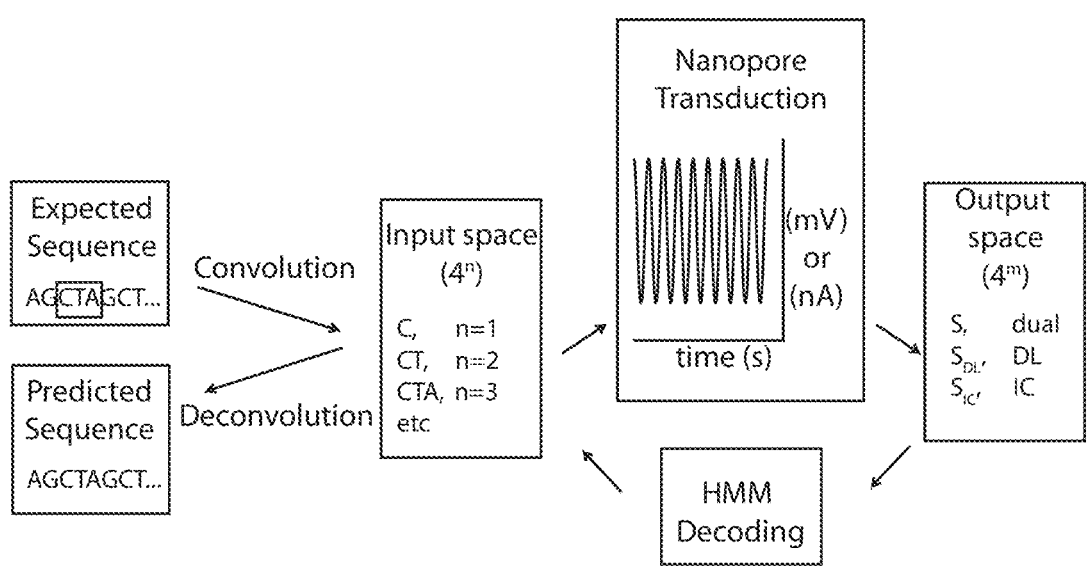
FIG. 14C The flow of information in the nanopore sequencing system. The expected (known) DNA sequence is transformed into $4^n$ space while the output sensor data is quantized into $4^m$ space. The hidden Markov model is trained by comparing the input and output spaces for DNA with known sequences. To determine the sequence of an unknown DNA sample from the sensor output, the observed output is decoded with a Viterbi algorithm and HMM, then deconvolved with the appropriate vector, $f(n)$.

Methods:

Nanopore Design and Experimental Setup:

A nanopore was fabricated in a 50 nm thick suspended silicon nitride membrane overlaid with a 5 nm thick gold ring electrode (FIG. 14) as has been reported in earlier work. The nanopore was positioned between two fluid reservoirs so that the nanopore was the only fluidic connection between reservoirs. An ionic current was driven through the nanopore by an applied electric potential (10 mV between reservoirs) and measured with a voltage-clamp amplifier (Axopatch 200B, Molecular Devices, CA). The gold, nanoscale ring-electrode on the mouth of the nanopore was charged with a small electrical current (37.4±3.2 pA, Versastat MC, Princeton Applied Research, TN) and the charging potential was recorded as the double layer potential. These two signal-channels (ionic current and double layer potential) were recorded at 80,000 samples per second (National Instruments, NI PCI-6221, TX) and spike signals associated with analyte translocation were considered as the ionic current signals and double layer potential signals. The steady-state, baseline double layer potential was recorded along with the molecular translocation time of detected analytes (full duration at half maximum of the spike signals in the ionic current), which allowed calculation of single-molecule mobility using a relationship developed in previous work $$\left(\mu = \frac{L^2}{V_{ss} F t_{IC}}\right),$$

where L is the length of the nanopore (55 nm), $V_{ss}$ is the steady-state double layer potential, F is Faraday's constant, and $t_{IC}$ is the translocation time. These three signals (ionic current, double layer potential, and mobility) are simultaneous measurements obtained from single molecules as they translocate the nanopore and are related to the size and charge of the individual analyte molecules (FIG. 14).

Small Molecule and Mixture Measurements:

Nanopore measurements were taken from solutions containing single-types of analytes or mixtures of several types of analytes. Mixtures of analytes contained from 2 to 8 different analytes each at 10 nM concentration. All solutions included a supporting electrolyte of 1 mM NaF. Analyte species considered in this study included citric acid, ascorbic acid, oxalic acid, hydroquinone, glucose, acetaminophen, urea, and cholesterol. These analytes were considered due to their range of valence charge and size, as well as for their biological, chemical, and medical relevance.

Measurements from solutions containing only one analyte were concatenated to create artificial datasets that replicated the content of the mixtures for validation purposes. The artificial mixtures contained the same 2 to 8 analytes as in the solution mixtures with 1000 signal vectors per analyte (comparable to the rate of detection in multi-analyte mixtures). The order of translocation signals within each artificial dataset was randomized to simulate the unordered analyte detection in measurements from mixtures. The identities of the analyte species associated with each set of translocation signals in the artificial datasets were retained throughout randomization so that the analyte identity predicted by clustering could be directly compared. Clustering of artificial datasets was blind to the retained identities.

DNA Measurements:

DNA samples consisting of purified dsDNA PCR product with known sequence and lengths between 154 bp and 463 bp were prepared in 1 mM NaF solution at pH 10. The pH was adjusted by titration with aqueous NaOH in order to denature the DNA. Only one type of DNA was considered per acquisition experiment. Signal acquisition conditions were otherwise identical to the case of acquisition from mixtures, differing only in the composition of the test solution. The ionic current and double layer potential traces were further filtered with a digital passband filter (70-1500 Hz, 50 dB/dec) where the selected passband was selected to contain 4 peaks in the power spectrum analysis of measurement traces. The two-channel data acquisition was evaluated in post-processing with a custom basecaller algorithm (as described in the following sections). Hidden Markov model (HMM) training was processed on the Clemson Palmetto Cluster with up to 550 GB of memory.

Clustering Methods:

In order to identify characteristic signals of small molecule analytes in a mixture, all artificial mixture datasets and mixture measurement datasets were evaluated by a hierarchical clustering algorithm with a normalized Euclidean distance metric and Ward's objective function. The Euclidean distance metric is normalized to better handle the variation in scale between signal types. Ward's method minimizes the internal variance of the predicted clusters in order to produce signal distributions with good internal similarity. In this study, hierarchical clustering was chosen for its deterministic operation and the capability of selecting the optimal number of clusters post-clustering.

Three aspects of clustering were considered in this study: prediction of the number of analytes in a mixture, prediction of the distributions of characteristic signals, and prediction of characteristic signal centroids. The number of analytes in a mixture was predicted from internal validation criteria and compared to the number of analytes in solution. The internal validation criteria were obtained by first clustering mixture signals into 2 to 20 clusters using a variety of algorithms (hierarchical clustering, Gaussian mixture modeling, and kmeans), then evaluating the fit for each division. For each clustering method and expected number of clusters, the Calinski-Harabasz, Davies-Bouldin, gap, and silhouette criteria were evaluated. Over the range of clusters considered, the index of the first local maximum criteria value (or local minimum in the case of Davies-Bouldin criteria) was selected as the predicted number of clusters. A composite prediction was generated by averaging the predictions from several clustering methods and criteria.

Validation of the clustering method in mixture measurements was assessed by comparing the residual error of predictions with the residual error from clustering the artificial datasets. The residual error of the predictions was calculated by determining the difference between the predicted cluster centroids and signal centroids from individually sampled analytes. In order to detect a particular target analyte in a mixture (as in a toxin, biomarker, etc), the characteristic signals of the target species were compared to each cluster centroid predicted from the mixtures. Residual errors between the characteristic signals of the target and the predicted cluster centroids were determined for each combination of nanopore signals (double layer potential, ionic current, and mobility) and compared to the mean error of the clustering algorithm.

Definition of Sensor Input and Output Spaces for DNA Sequencing:

In order to develop a method of sequencing DNA, the nanopore sensor system is considered as analogous to a model communications system for transmitting a quaternary digital message (DNA) as a decodable signal. In this application, the transmitted message is the total DNA sequence which is sampled by the nanopore as segments of n-nucleotides, where the nanopore sensor has a capability of detecting at minimum n-nucleotides in a given instant (ideally n=1). The electrical signals from the nanopore (ionic current and double layer potential) are quantized and considered as the received encoded message (FIG. 14($c$)). In order to properly map the signal source (n-nucleotide segments) to sensor output space (quantized electrical signals), one must have an idea of the size of each space.

In an ideal situation, the signal source would be the 4 nucleotide bases (Adenine, Guanine, Cytosine, and Thymine) and the output signal would be quantized to 4 levels with a one-to-one mapping, however, this is often prohibited by high noise levels. It has been shown that considering a multi-nucleotide signal source (where the input signal is obtained from a short segment of DNA, (FIG. 14($b$)) can increase the sequencing accuracy of the ionic current signal in determining the correct sequence of the input strand. When DNA is the signal source with 4 base nucleotides, the DNA sequence is considered as a message in a base 4 (quaternary) number system and the size of the input space increases by powers of 4. With n-nucleotide resolution, there must be $4^n$ input symbols and at least as many output symbols. For example, if n=1, the $4^1$ symbols in the input space are {'A', 'G', 'C', 'T'}. If n=2, the $4^2$=16 symbols in the input space are {'AG', 'AC', 'AT', 'GA', 'GG', 'GC', 'GT', 'CA', 'CG', 'CC', 'CT', 'TA', 'TG', 'TC', 'TT'}, and for n=3, there are $4^3$=64 input symbols consisting of triplets like 'AAA'. When DNA sequences were numerically encoded using an arbitrary key-value pairing such as T=0, G=1, A=2, C=3, the larger n-nucleotide spaces may be calculated by convolving the numerical sequence with the discrete function $f(x)=4^x$ where x is an integer in the range [0, n−1]. When training the HMM, the known sequences of sampled DNA were transformed into the appropriate $4^n$-space and compared to the quantized sensor output. When evaluating the sensor design, the quantized output would be mapped to the $4^n$-space of the input, and then deconvolved to obtain the predicted nucleotide sequence (FIG. 14($c$)).

In order to unambiguously reconstruct the transmitted message (the full DNA sequence), the output space (quantized nanopore signals) must have at least as many symbols as the input space. It is desirable to increase the number of symbols in the output space over the size of the input space to reduce the probability of collisions, where multiple inputs map to the same output. The number of quantization levels may be arbitrarily chosen within a range, where the minimum number of levels is equal to the size of the input space and the maximum number is limited by the system noise level. At some large number of quantization levels, the step size between adjacent quantization levels (the resolution of the sensor signals) will fall below the system noise level and similar outputs will be statistically indistinguishable. Thus the number of quantization levels is bounded on the lower end by the size of the input space ($4^n$) and on the upper end by the noise of the system.

Since measurements are made of two simultaneous signals (ionic current and double layer potential), any signal of one type may be paired with the corresponding signal to produce a dual-channel signal. If the output of each signal type is quantized into $4^m$ levels, the total number of levels in the combined output space is $4^{m_i+m_v}$, where $m_i$ is the exponent in the ionic current channel and my is the exponent in the double layer potential channel (base 4 is used here to simplify size comparisons between the input and output spaces). For example if $m_i=m_v=1$, then the 4 symbols in each output space may be combined in $4^{1+1}=16$ ways (using the symbols W, X, Y, and Z, the combined output space contains the elements {WW, WX, WY, WZ, XW, XX, XY, XZ, YW, YX, YY, YZ, ZW, ZX, ZY, ZZ}). Thus, the total size of the dual channel output space is the product of the size of the spaces of the individual channels. In order to satisfy the minimum requirements of 1 to 1 mapping, the relationship between output exponents ($m_i+m_v$) and the input exponent n must be such that $(m_i+m_v)>=n$, where a value of $(m_i+m_v)$ much greater than n is desirable. By increasing the quantization level of the output, the multi-nucleotide resolution of this nanopore sensor can be accommodated and the probability of collisions reduced to a negligible level.

DNA Signal Feature Characterization:

In order to obtain the quantized output space, the digitized and filtered electrical measurements of DNA-containing solutions in the nanopore device were processed to obtain translocation signals. Within the two signal types (ionic current and double layer potential), the beginning and end of DNA strand translocation events were identified by an edge detection algorithm. The time duration of translocation events was used as a criterion to identify data segments which likely contain DNA signals. Time segments which were aligned in the ionic current and double layer potential channels and fell within an empirically determined range were identified as full translocation events (FIG. 20), second peak, see Results and Discussion). These data segments were further sub-divided into n-nucleotide regions, where n-nucleotide regions were demarcated by local extrema within the data segment (the series of local maxima in the double layer potential channel or minima in the ionic current channel). In each data segment and nucleotide region, simultaneity of edges and extrema between the ionic current and double layer potential was considered as a requirement for further evaluation. Essentially, simultaneously occurring data segments with similar duration were identified in the ionic current and double layer potential channels. The positions of extrema within pairs of data segments were compared and data segments with similar duration and aligned extrema positions were retained. Each data segment was converted to a vector of signal values consisting of the value at the midpoint of each nucleotide event. The signal vectors (in units of mV or nA) were then quantized to values in the range of 1 to $4^{m_i}$ or 1 to $4^{m_v}$ levels using a least squares method. The quantization levels were determined by dividing a fixed, empirically determined range into $4^{m_i}$ or $4^{m_v}$ levels (30 mV range for the double layer potential signal and 1.2 nA range for the ionic current signal, where all observed signals fall within these ranges). With the ionic current and double layer potential signals quantized, the dual channel output space was calculated using the formula: $S=4^{m_i}(S_{DL}-1)+S_{IC}$, where S is the quantized dual channel signal, $S_{DL}$ is the quantized double layer potential signal, and $S_{IC}$ is the quantized ionic current signal. The quantized output signals were decoded into $4^n$ space with a hidden Markov model (HMM) using a Viterbi algorithm to reconstruct the input space. A separate HMM was trained for each combination of n, $m_i$, and $m_v$.

Hidden Markov Model Training for DNA Sequencing:

DNA samples with known sequence were used to train HMMs for a range of values of n, $m_i$, and $m_v$. The training data consisted of 96 datasets from 32 DNA samples (PCR amplified DNA, 154-463 bp in length) with over $10^5$ reads obtained in total. The HMMs were evaluated on 3 data sets from 3 DNA samples. Training consisted of obtaining the sensor output via experiment (as described in the methods section 'DNA measurements') and estimating the transition and emission probability distribution of the HMMs with a commercially available training algorithm (Mathworks, Matlab 2013a, MA). In evaluation of a wide range of values for $m_i$ and $m_v$, some cases for large values ($m_i$ or $m_v>7$) were not able to be completed with the computational resources available. The known, encoded, and convolved sequence of each DNA sample was considered as the sensor input for HMM training purposes while the quantized electrical signals were considered the sensor output. The predicted input space was obtained by parsing the sensor output from the evaluation DNA samples with a Viterbi algorithm for a given HMM. The predicted $4^n$ sensor input obtained from the HMM was deconvolved with the appropriate n-element convolution vector ($f(x)=4^x$ where x is an integer in the range [0, n−1]) to obtain the predicted sequence. Sequencing accuracy of the predicted sequence was evaluated by finding the proportion (as a percentage) of aligned, matching bases between the predicted and expected sequences, where the expected sequences were provided by the DNA supplier.

Results

Figure 15A:
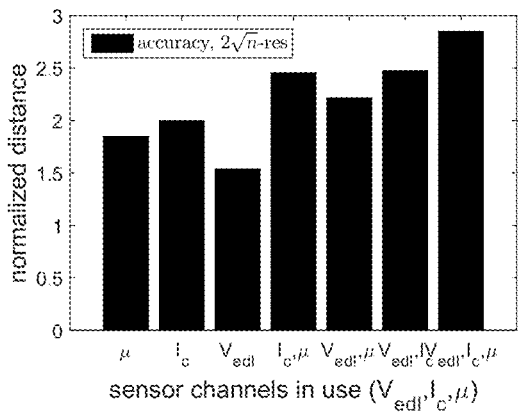
FIG. 15A The accuracy of the signal channels increases when more signal channels are considered. Combining individual channels increases the accuracy over the accuracy of any of the constituent channels. Since the goal of clustering is to accurately predict cluster centroids, it is only the accuracy of the methods that contributes to clustering validity.
Figure 15B:
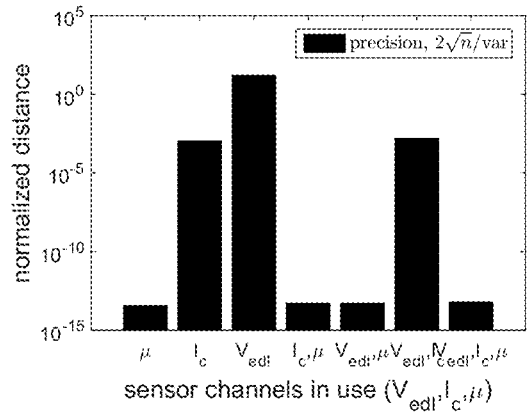
FIG. 15B The precision of the signal channels varies by orders of magnitude, with the double layer potential offering the highest observed level of precision. When comparing centroids between separate measurements, it is the precision of the measurements that affects error levels. In these situations, it is best to consider the double layer potential alone.

Accuracy and Precision of Signals and Signal Combinations:

In considering the predictive properties of these nanopore signals, the accuracy and precision for characterizing molecular analytes can be quantified. The use of multiple signals offers advantages in that the accuracy of the signal combinations will increase when more types of signals are considered in combination ((FIG. 15(a)). The precision for each combination of signals in (FIG. 15(b)), demonstrates that precision varies by orders of magnitude across all signal channel combinations and the double layer potential signal alone (Vex) has the highest value. In single analyte characterization where results will depend on repeatability, high precision measurements are desired. The algorithmic approach may be tuned for a given task by optimizing for high accuracy (using a multi-signal approach) or high precision (using the double layer potential alone).With this flexibility, a single nanopore device can be useful for a wide variety of applications.

Figure 16A:
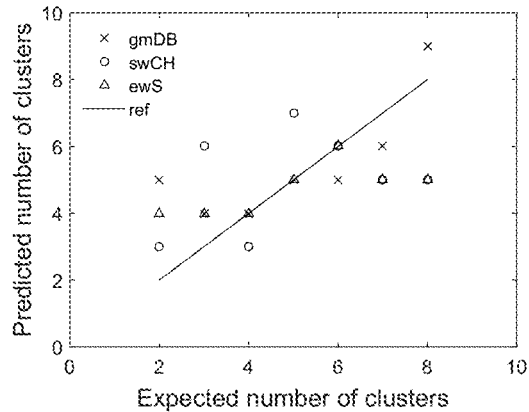
FIG. 16A The predicted number of clusters using various techniques. While some individual algorithms correctly predict the number of clusters over a small range, none predict the number of clusters accurately over the whole range.
Figure 16B:
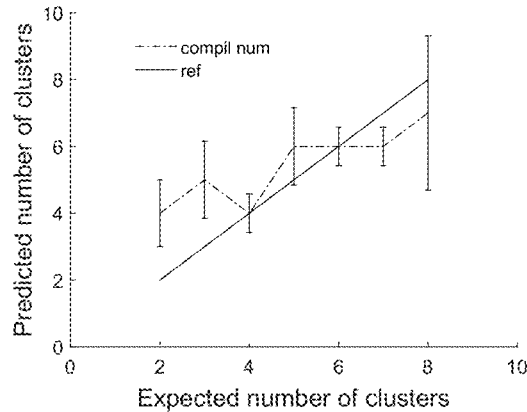
FIG. 16B By averaging the predictions and rounding to the nearest integer with a ceiling function, a compiled prediction by calculated. While individual techniques can be correct over small ranges, the compiled prediction has a lower overall error across the whole range.
Figure 17A:
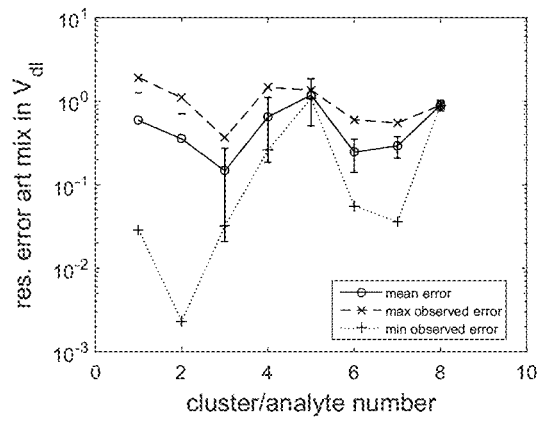
FIG. 17A-17G detail the residual error between expected and predicted signal values for FIG. 17A the double layer potential signal, FIG. 17B the ionic current signal, and FIG. 17C the mobility signal in pseudo-mixture clusters generated with Seuclidean ward hierarchical clustering. The level of error is consistent across mixtures within each signal modality.
Figure 17B:
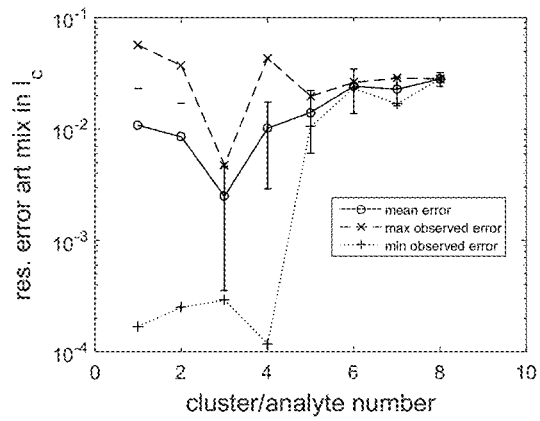
Figure 17C:
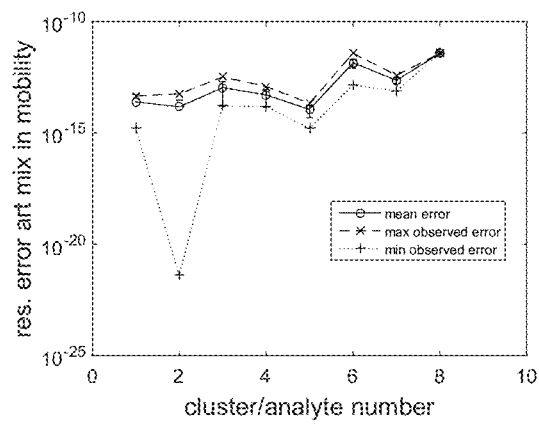
Figure 17D:
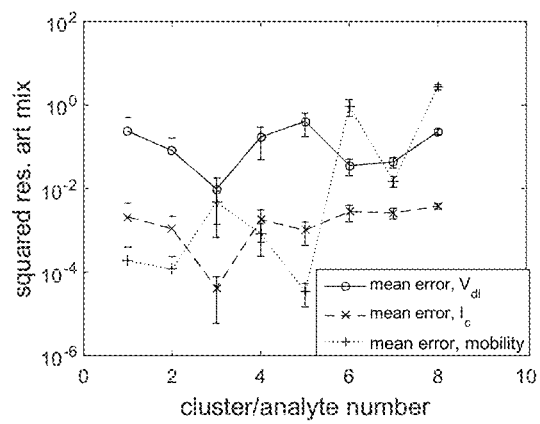
Figure 17E:
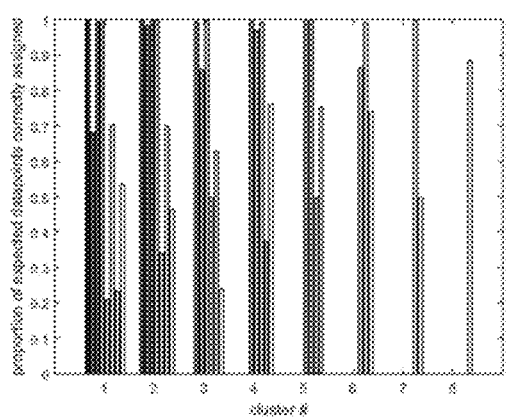
Figure 17F:
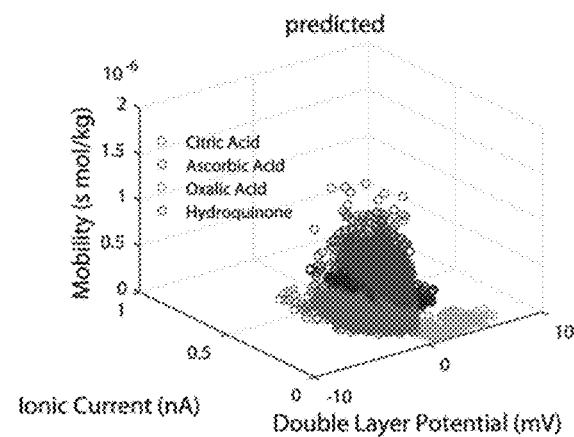
Figure 17G:
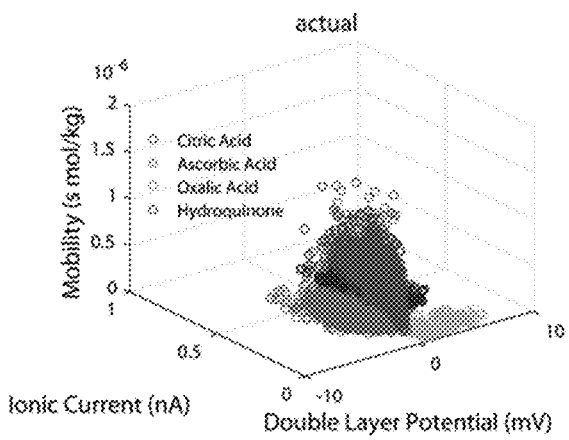
Figure 18A:
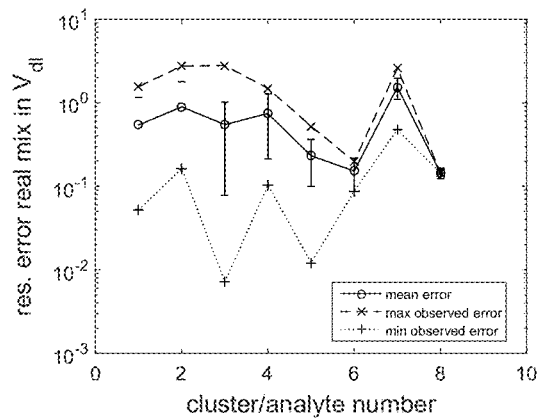
FIG. 18A-18D detail the residual error between expected and predicted signal values for FIG. 18A the double layer potential signal, FIG. 18B the ionic current signal, and FIG. 18C the mobility signal in real-mixture clusters generated with Seuclidean ward hierarchical clustering. The level of error is consistent across mixtures within each signal modality and comparable to the residual error in the pseudo-mixture analysis.
Figure 18B:
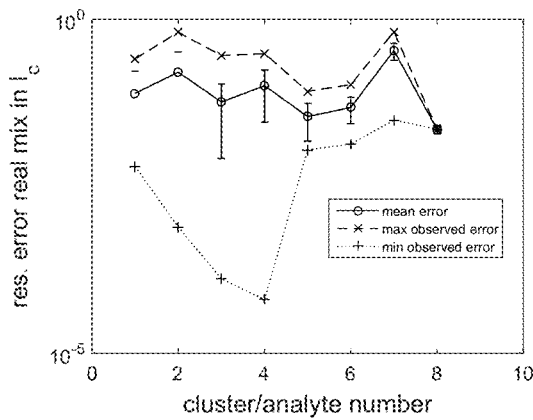
Figure 18C:
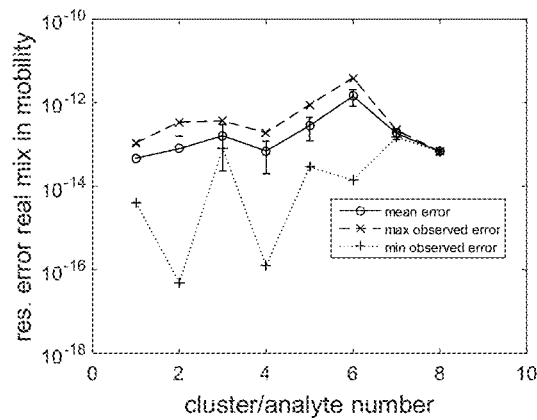
Figure 18D:
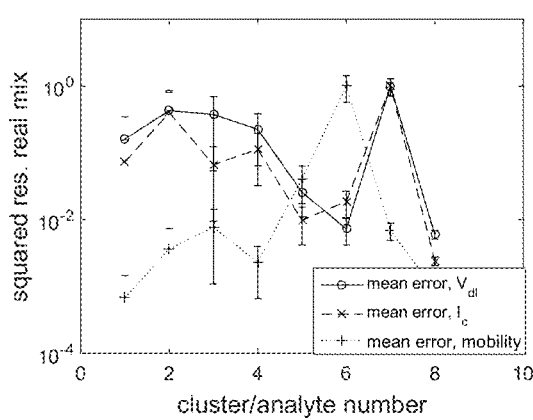

Clustering Results:

Predicting the Number of Clusters Mixtures:

FIG. 16 shows results of predicting the number of characteristic signals from measurements of mixtures. Perfect prediction accuracy would result in predictions along the reference line, where the predicted number of characteristic signals is equal to the number of analytes in the mixture solution. It was observed that the most consistently accurate predictions were generated when three methods (gaussian mixture modeling with the Davies-Bouldin criterion, hierarchical clustering with the Calinski-Harabasz criterion, and hierarchical clustering with the Silhouette criterion) were considered and the mean predicted number of clusters was calculated. When individual prediction algorithms were considered (FIG. 16(a)), the predicted number of clusters matches the expected number of analytes in the middle of the experimental range (4 to 6 analytes) with a wider variation when very few and very many analytes were present in solution. FIG. 16b shows that the mean predictions are much more useful than the individual criteria and correctly predict the number of analytes in solution within one or two standard deviations throughout the range.

Clustering of Artificial Datasets:

Artificial mixture datasets were evaluated for the predicted cluster centroid and distribution (FIG. 17). FIG. 17a-c shows the residual error between expected and predicted characteristic signal centroids for artificial datasets containing 2-8 analytes, while FIG. 17d displays the normalized residual error in each signal-channel. The residual error is insensitive to the number of species in solution for the double layer potential (FIG. 17(a)), ionic current (FIG. 17(b)) and mobility (FIG. 17(c)). Since the same number of datapoints were considered for each species in the artificial dataset (1000 datapoints/analyte) and the order of datapoints was randomized, the error is due to the characteristics of the signal-channels and clustering method. FIG. 17e shows the proportion of datapoints correctly assigned to a characteristic signal distribution for each artificial dataset. The number of datapoints assigned to the correct distribution decreases as the number of species in the dataset increases (FIG. 17(e)). The fact that the centroid error remains small and relatively constant within each signal channel (FIG. 17(a-d)) while the number of correctly assigned datapoints decreases for more complex solutions (FIG. 17(e)) indicates that the mis-assigned datapoints do not heavily weight the predicted centroids. The mis-assigned datapoints likely occur in areas where clusters overlap or coincide, which is supported by visual examination of the expected and predicted characteristic signal distributions for a 4-analyte artificial mixture (FIG. 17(f,g)). While the clustering algorithm may not correctly predict the identity of individual datapoints, especially when the signals occur on the edge of a cluster or when a large number of analytes are present in a mixture, the prediction of the cluster centroids remains accurate, even in complex mixtures.

Clustering of Mixture Measurements:

FIG. 18 shows the residual error between the predicted and expected signal centroids obtained from measurements of mixtures of analytes. Within the double layer potential (FIG. 18(a)), ionic current (FIG. 18(b)), and mobility (FIG. 18(c)), the residual error is insensitive to the number of analytes present, as in the clustering of artificial mixtures. FIG. 18d illustrates that the normalized residual errors are comparable across the three nanopore signal-channels. In all signal-channels, the residual error of the predicted centroids is comparable to the residual error in artificial mixtures (FIG. 17(a-d)). Given the small error, comparability with the artificial mixture clustering results, and the strength of the artificial mixture clustering results, centroid predictions from mixture measurements appear to very similar to the characteristic signals from single-analyte measurements.

Figure 19A:
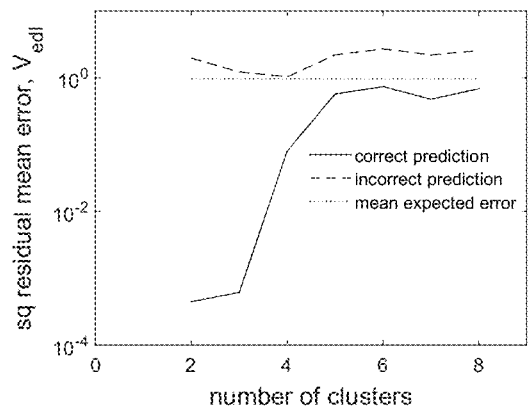
Figure 19B:
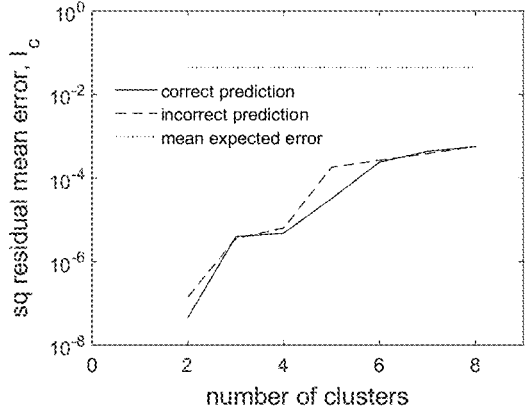

Targeted Analyte Detection:

Clustering of a mixture allows the nanopore sensor to be used as a non-functionalized, targeted detection method. The presence of a target analyte may be evaluated by calculating the residual error between the characteristic target centroid and each centroid predicted from clustering the mixture, and comparing the errors against mean clustering error. FIG. 19 shows the mean residual error for the double layer potential (FIG. 19(a)), ionic current (FIG. 19(b)), and mobility (FIG. 19(c)), when comparing the targets to the predicted clusters. Of the 3 signal types produced by this nanopore, only the double layer potential signal ($V_{edl}$) has the capability to unambiguously predict the presence of an analyte in a mixture and reject non-matching comparisons. The mean error in the double layer potential channel (FIG. 19(a)) between an analyte's characteristic signal and clustered mixture signal is always less than the mean expected clustering error. Similarly, the mean error of mis-matches in the double layer potential signal produce error that is larger than the mean clustering error. In the ionic current (FIG. 19(b)) and mobility ((FIG. 19(c)) signals, the error of correct and incorrect predictions is not sufficiently different to determine that characteristic signals match for all numbers of analytes. Based on the comparisons in FIG. 19, considering the double layer potential signal alone offers the best results for single analyte identification. By comparing the signal centroid of a target analyte to the centroids of predicted clusters, the presence or absence of the target analyte in the mixture may be quantitatively assessed.

DNA Results

Translocation Time:

Translocation events were detected by identifying paired transitions in the ionic current and double layer potential. FIG. 20a shows a typical distribution of the time duration of translocation events detected in the double layer potential channel. The distribution of the durations is bimodal with a first peak centered at 20.8 ms while the location of the second peak is dependent on the length of the DNA strand under investigation. A bimodal distribution of translocation events is consistent with the observations of DNA translocation studies, where the first peak is typically considered as noise or incomplete translocation events. The time duration associated with the second peak in the histogram is variable and linearly correlated to the length of the DNA strand (t=0.0112+0.0002 L, $R^2$=0.9744), where t is time in seconds and L is the length of the DNA strands in nucleotides (FIG. 20(b)). The duration of events captured in the first peak of the histogram is not proportional to the length of the DNA sample. The linear relationship between the length of the DNA strand and translocation time indicates that the translocation is relatively slow, with an average rate of 200 μs/nucleotide, which is consistent with translocation rates observed in this type of ring-electrode nanopore. The time resolution of measurements was 12.5 μs (80,000 samples/s), so the translocation events and nucleotide signals are well sampled at this translocation rate. In the case of the two layer (SiN/Au) nanopore considered in this study, antagonistic effects of differing surface potential polarities are believed to be responsible for the capture and slow translocation rate of ssDNA. The positive baseline surface potential of the gold (Au) layer supports capture of the negatively charged DNA. However the transition between the positive gold surface and the negative SiN surface creates an electrical barrier which impedes translocation of the nanopore. Previously we have observed that this potential difference results in charge exclusion regions which can eliminate any baseline ionic current.

Figure 21C:
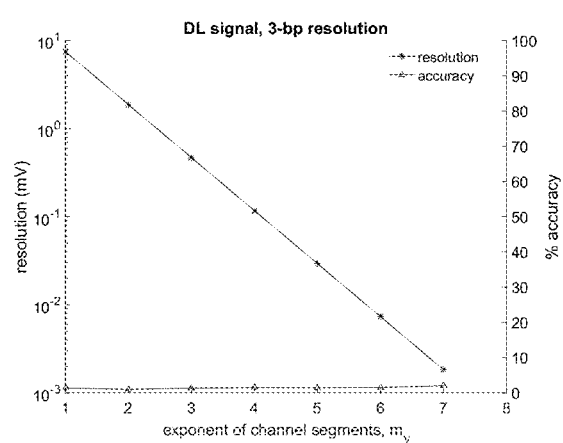

Evaluation of the Double Layer Potential Signal in DNA Sequencing:

FIG. 21a-c shows the signal resolution and the sequencing accuracy of the double layer potential signals from the evaluation data set for n=1, 2, and 3 nucleotide input resolutions. FIG. 21 indicates that the accuracy of the double layer potential is not proportional to the number of quantization levels when the output space is quantized to fewer than $4^5$ levels (1024 levels). Above $4^5$ levels in the output space, the accuracy of the double layer potential signal rapidly increases with increased quantization for the n=1 and n=2 cases. Quantization of the double layer potential signal was increased up to $4^9$ levels, at which point the sequencing accuracy approaches 100% for 1 and 2 nucleotide resolutions. The maximum accuracy observed is 99.3% for 1 nucleotide resolution (FIG. 21a), 94.9% for 2 nucleotide resolution (FIG. 21b), and 2% for 3 nucleotide resolution (FIG. 21c), each maximum occurring at the $4^9$ quantization level. The accuracy of the double layer potential was higher when considering the 1 nucleotide resolution case compared to the 2 or 3 nucleotide resolution case, suggesting that the double layer potential signal is generated by single nucleotide segments of the DNA sample. The quantization step size (output resolution) of the sensor decreases with increasing quantization level, since the maximum range of the electrical output is fixed in this study. For quantization levels from $4^1$ to $4^9$, the output resolution of the double layer potential decreased from 4.25 my to 114 nV (where the output resolution is the signal range divided by the number of quantization levels). The accuracy of the basecalls rapidly increase in proportion to quantization at levels greater than $4^5$ (corresponding to an output resolution of 29 μV). The smallest output resolution (at $4^9$ quantization levels) is much smaller than expected due to the typical noise level of the signal, however, the HMM method is expected to be error tolerant and clearly offers advantages in this case.

Figure 21D:
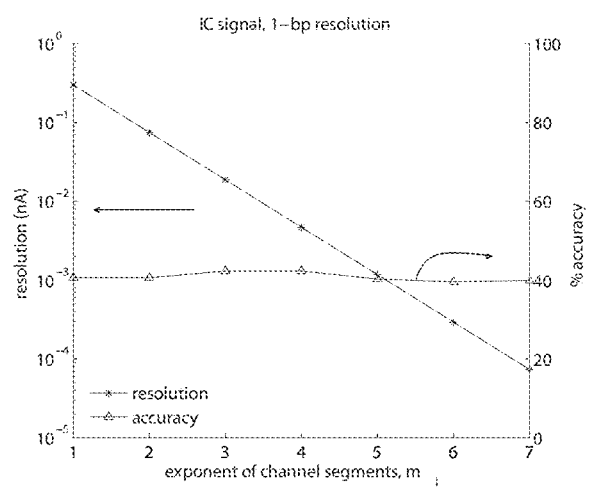
Figure 21E:
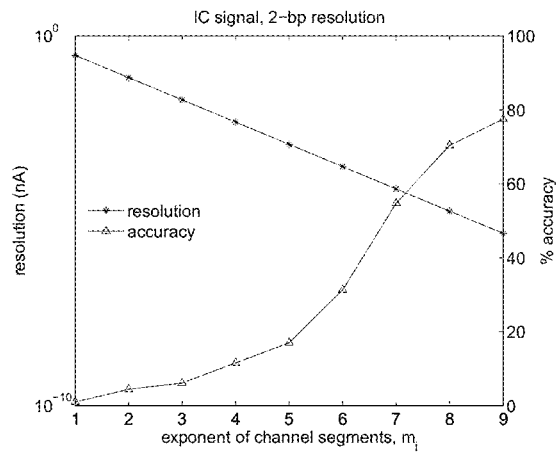
Figure 21F:
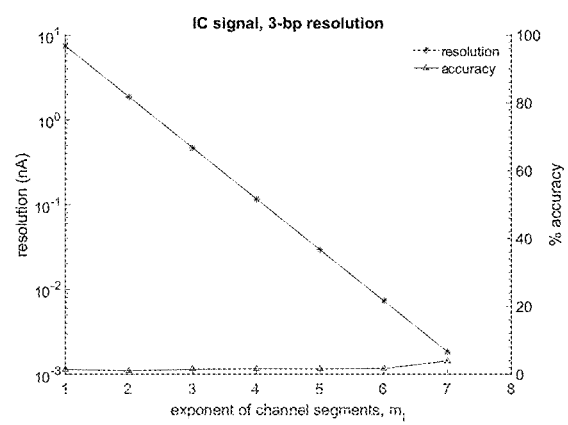

Evaluation of the Ionic Current Signal in DNA Sequencing:

FIG. 21d-f shows the percent accuracy of the evaluation data set when the ionic current channel is evaluated alone. For the 1 and 3 nucleotide resolution cases (FIG. 21d,f), the accuracy shows no proportionality to the quantization level of the output. The 2 nucleotide resolution case (FIG. 21e) is proportional to the quantization level of the output, and accuracy increases up to 77.6% ($4^{mi}=4^9$, corresponding to a 4.6 fA output resolution). Previous studies have shown that considering nucleotide resolution similar to the actual nanopore source will increase the accuracy of the basecalls when using a HMM method. The higher accuracy of the 2 nucleotide resolution case (FIG. 21e) compared to the 1 or 3 nucleotide cases (FIG. 21d,f), indicates that the ionic current signal is likely related to 2 nucleotide segments of the translocating DNA in this nanopore.

The different nucleotide resolutions in the ionic current signal and the double layer potential signal suggests that the physical region interrogated by the ionic current signal is larger than the region interrogated by the double layer potential signal. Since the ionic current signal may be generated in a sub-section of the total thickness of the nanopore membrane (55 nm) and the double layer potential signal is generated within the thickness of the metal ring electrode (5 nm), it follows that the ionic current signal would have a larger nucleotide resolution (n=2) than the double layer potential signal (n=1). DNA will stretch to more than twice the relaxed distance between bases (stretch to 0.58-0.75 nm from 0.34 nm) in a small nanopore under a moderate electrical field. The thickness of the narrow, metallic region of this nanopore is in the range of 4-6 nm, which is much larger than the expected length of 1 or 2 bp segments of DNA. However, previous modeling work has indicated that the nanopore signals are generated in the narrowest portion of the nanopore (the region with the smallest cross sectional area) such that the actual sensing volume is much smaller than the total volume of the nanopore.

Figure 21G:
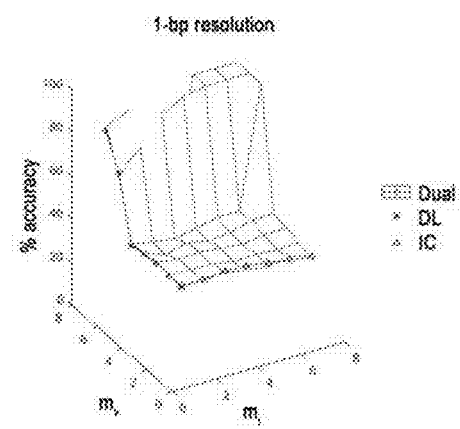
Figure 21H:
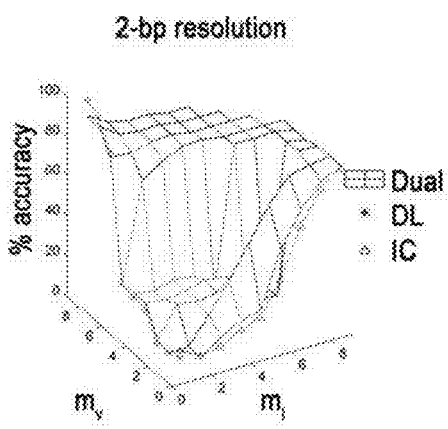
Figure 21I:
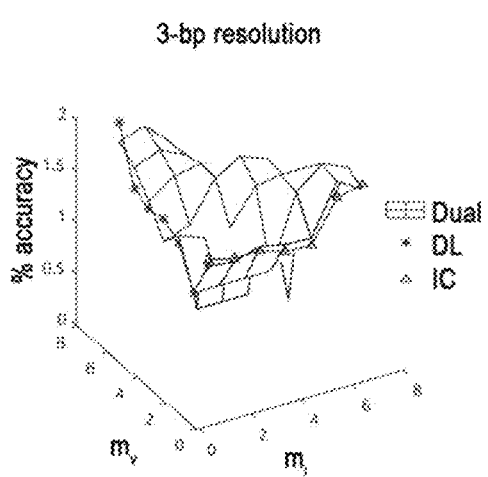

Evaluation of the Dual Channel Signal in DNA Sequencing:

FIG. 21g-i shows the results of considering the dual encoded measurements of the ionic current and double layer potential signals. The dual channel outputs tend to produce higher accuracy than the individual channels when the quantization of the individual channels is less than $4^7$. The highest accuracy observed in the dual channel method (97.9%) occurred for the n=1 nucleotide resolution case where $m_i=1$ and $m_v=9$, implying that the high accuracy was primarily due to the double layer potential signal. For the individual signal channels at n=1 nucleotide resolution (FIG. 21g), the double layer potential ($m_v=9$) produced accuracy of 99.3%, and the ionic current ($m_i=1$) produced accuracy of 40.6%. When the accuracy of one channel is much lower than the other, the accuracy of the dual measurement tends to fall between the accuracy of the individual channels. The dual channel method offers a trade-off in terms of quantization requirements, where evaluation of lower quantization-level signals can produce relatively high accuracy. For example, in the case where n=1, $m_i=7$, and $m_v=5$, the ionic current signal alone produces accuracy of 62.1%, the double layer potential signal alone produces accuracy of 50.2%, and the dual channel approach produces an accuracy of 97.6%. The transition from higher accuracy in the dual channel approach to the higher accuracy in the double layer potential signal occurs when the additional output space in the dual channel signal (which reduces collisions) is outweighed by a high error rate from the ionic current signal. However, the capability of obtaining high accuracy sequences with the low quantization-level dual channel method offers advantages in error tolerance and computational efficiency.

Conclusion:

By adapting clustering techniques to measurements of mixtures of small molecules obtained in a solid-state nanopore, the ability to reliably identify the component species is demonstrated. By considering internal validation techniques, it is possible to estimate the number of analytes present in a mixture. Clustering of artificial datasets demonstrates that while it is difficult to predict the distribution of signal clusters within mixtures, the cluster centroids can be accurately predicted. When mixture measurements are assessed with clustering techniques, the predicted centroids are similar to the expected centroids and the error level of the clustering algorithm is comparable to that of the artificial mixtures. By considering the double layer potential signals alone, highly precise comparisons can be made between expected and predicted signal cluster centroids. The mean error associated with the clustering algorithm provides a straightforward standard to determine when the comparison between expected and predicted centroids come from the same analyte.

By considering double layer potential, ionic current, and dual channel signals with multi-nucleotide inputs, attain high accuracy and resolution is obtained when sequencing individual DNA molecules. The non-functionalized method developed here may be improved by further reducing systemic noise, decreasing the physical n-nucleotide resolution of the nanopore, or increasing the number of data channels obtained from the sensor. However, the double layer potential signal offers extremely high (>99%) sequencing accuracy in single-molecule, single-read DNA sequencing while the dual channel method can offer high sequencing accuracy (>97%) with fewer quantization levels, offering a computational trade-off. The nanopore sequencing device is itself reusable and individual devices have been used over a period of months during the development of this approach. The minimal, low-cost reagents (NaF, NaOH, and $H_2O$) and the high accuracy attained indicate potential for widespread genomic and genetic applications.

Every formulation or combination of components described or exemplified can be used to practice the invention, unless otherwise stated. Specific names of materials are intended to be exemplary, as it is known that one of ordinary skill in the art can name the same material differently. One of ordinary skill in the art will appreciate that methods, device elements, starting materials, and synthetic methods other than those specifically exemplified can be employed in the practice of the invention without resort to undue experimentation. All art-known functional equivalents, of any such methods, device elements, starting materials, and synthetic methods are intended to be included in this invention. Whenever a range is given in the specification, for example, a temperature range, a time range, or a composition range, all intermediate ranges and subranges, as well as all individual values included in the ranges given are intended to be included in the disclosure.

While the terms used herein are believed to be well understood by one of ordinary skill in the art, definitions are set forth herein to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a protein" includes a plurality of such proteins, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

Throughout this document, various references are mentioned. All such references are incorporated herein by reference.

REFERENCES

[1] Timp W, Mirsaidov U M, Wang D, corner J, Aksimentiev A and Timp G 2010 Nanopore sequencing: electrical measurements of the code of life IEEE *Trans. Nanotechnol.* 9 281-94

[2] Postma H W C 2010 Rapid sequencing of individual DNA molecules in graphene nanogaps *Nano Lett.* 10 420-5

[3] Branton D et al 2008 The potential and challenges of nanopore sequencing *Genome Res.* 26 1146-53

[4] Maitra R D, Kim J and Dunbar W B 2012 Recent advances in nanopore sequencing *Electrophoresis* 33 3418-28

[5] Eisenstein M 2012 Oxford Nanopore announcement sets sequencing sector abuzz *Nat. Biotechnol.* 30 295-6

[6] Liu Y, Dong X and Chen P 2012 Biological and chemical sensors based on graphene materials *Chem. Soc. Rev.* 41 2283-307

[7] Kowalczyk S W, Grosberg A Y, Rabin Y and Dekker C 2011 Modeling the conductance and DNA blockade of solid-state nanopores *Nanotechnology* 22 315101

[8] Schneider G F, Kowalczyk S W, Calado V E, Pandraud G, Zandbergen H W, Vandersypen L M K and Dekker C 2010 DNA translocation through graphene nanopores *Nano Lett.* 10 3163-7

[9] Venkatesan B M, Estrada D, Banerjee S, Jin X, Dorgan V E, Bae M-H, Alum N R, Pop E and Bashir R 2012 Stacked graphene-Al2O3 nanopore sensors for sensitive detection of DNA and DNA-protein complexes *ACS Nano* 6 441-50

[10] Ivanov A P, Instuli E, McGilvery C M, Baldwin G, McComb D W, Albrecht T and Edel J B 2011 DNA tunneling detector embedded in a nanopore *Nano Lett.* 11 279-85

[11] Ohshiro T and Umezawa Y 2006 Complementary base-pair-facilitated electron tunneling for electrically pinpointing complementary nucleobases *Proc. Natl Acad. Sci. USA* 103 10-4

[12] Min S K, Kim W Y, Cho Y and Kim K S 2011 Fast DNA sequencing with a graphene-based nanochannel device *Nat. Nanotechnol.* 6 162-5

[13] Nelson T, Zhang B and Prezhdo O V 2010 Detection of nucleic acids with graphene nanopores: ab initio characterization of a novel sequencing device *Nano Lett.* 10 3237-42

[14] Apel P Y, Korchev Y, Siwy Z, Spohr R and Yoshida M 2001 Diode-like single-ion track membrane prepared by electro-stopping *Nucl. Instrum. Methods Phys. Res. B* 184 337-46

[15] Kalman E B, Sudre O, Vlassiouk I and Siwy Z S 2009 Control of ionic transport through gated single conical nanopores *Anal. Bioanal. Chem.* 394 413-9

[16] Vlassiouk I, Smirnov S and Siwy Z 2008 Ionic selectivity of single nanochannels *Nano Lett.* 8 1978-85

[17] Siwy Z S 2006 Ion-current rectification in nanopores and nanotubes with broken symmetry *Adv. Funct. Mater.* 16 735-46

[18] Siwy Z, Heins E, Harrell C C, *Kohli* P and Martin C R 2004 Conical-nanotube ion-current rectifiers: the role of surface charge *J. Am. Chem. Soc.* 126 10850-1

[19] Pang P, He J, Park J H, Krstić P S and Lindsay S 2011 Origin of giant ionic currents in carbon nanotube channels *ACS Nano* 5 7277-83
[20] Bearden S and Zhang G 2013 The effects of the electrical double layer on giant ionic currents through single-walled carbon nanotubes *Nanotechnology* 24 125204
[21] Hückel E and Debye P 1923 The theory of electrolytes: I. lowering of freezing point and related phenomena *Phys. Z.* 24 185-206
[22] Grahame D C 1947 The electrical double layer and the theory of electrocapillarity *Chem. Rev.* 41 441-501
[23] Bearden S, Simpanen E and Zhang G 2015 Active current gating in electrically biased conical nanopores *Nanotechnology* 26 185502
[24] Yang X and Zhang G 2008 The effect of an electrical double layer on the voltammetric performance of nanoscale interdigitated electrodes: a simulation study *Nanotechnology* 19 465504
[25] Yang X and Zhang G 2007 Simulating the structure and effect of the electrical double layer at nanometre electrodes *Nanotechnology* 18 335201
[26] Bard A J and Faulkner L R 2001 *Electrochemical Methods: Fundamentals and Applications* (New York: Wiley)
[27] Zhang G 2010 Simulating the electrical double layer capacitance *COMSOL Conf.* (Boston, Mass.)
[28] Kalman, E. B.; Sudre, O.; Vlassiouk, I.; Siwy, Z. S. Control of Ionic Transport through Gated Single Conical Nanopores. Anal. Bioanal. Chem. 2009, 394, 413-419
[29] Bacri, L.; Oukhaled, a G.; Schiedt, B.; Patriarche, G.; Bourhis, E.; Gierak, J.; Pelta, J.; Auvray, L. Dynamics of Colloids in Single Solid-State Nanopores. J. Phys. Chem. B 2011, 115, 2890-2898.
[30] Ali, M.; Mafe, S.; Ramirez, P.; Neumann, R.; Ensinger, W. Logic Gates Using Nanofluidic Diodes Based on Conical Nanopores Functionalized with Polyprotic Acid Chains. Langmuir 2009, 25, 11993-11997.
[31] Pintilie, F.; Luchian, T. Transport and Kinetic Features of Gold-Functionalized Artificial Nanopores. Romania 16, 273-281.
[32] Siwy, Z. S. Ion-Current Rectification in Nanopores and Nanotubes with Broken Symmetry. Adv. Funct. Mater. 2006, 16, 735-746.
[33] Bearden, S.; Simpanen, E.; Zhang, G. Active Current Gating in Electrically Biased Conical Nanopores. Nanotechnology 2015, 26, 185502.
[34] Yan, Y.; Wang, L.; Xue, J.; Chang, H.-C. Ion Current Rectification Inversion in Conic Nanopores: Nonequilibrium Ion Transport Biased by Ion Selectivity and Spatial Asymmetry. J. Chem. Phys. 2013, 138, 44706.
[35] Vlassiouk, I.; Smirnov, S.; Siwy, Z. Ionic Selectivity of Single Nanochannels. Nano Lett. 2008, 8, 1978-1985.
[36] Pang, P.; He, J.; Park, J. H.; Krstić, P. S.; Lindsay, S. Origin of Giant Ionic Currents in Carbon Nanotube Channels. ACS Nano 2011, 5, 7277-7283.
[37] Nelson, T.; Zhang, B.; Prezhdo, O. V. Detection of Nucleic Acids with Graphene Nanopores: Ab Initio Characterization of a Novel Sequencing Device. Nano Lett. 2010, 10, 3237-3242.
[38] Timp, W.; Mirsaidov, U. M.; Wang, D.; Comer, J.; Aksimentiev, A.; Timp, G. Nanopore Sequencing: Electrical Measurements of the Code of Life. IEEE Trans. Nanotechnol. 2010, 9, 281-294.
[39] Bearden, S.; Zhang, G. A Solid-State Nanopore as Biosensor. In Computational Bioengineering; Zhang, G., Ed.; CRC Press, 2015; pp. 355-376.
[40] Bearden, S.; McClure, E.; Zhang, G. Detecting and Identifying Small Molecules in a Nanopore Flux Capacitor. Nanotechnology 2016, 27, 75503.
[41] Cervera, J.; Schiedt, B.; Ramirez, P. A Poisson/Nernst-Planck Model for Ionic Transport through Synthetic Conical Nanopores. Europhys. Lett. 2005, 71, 35-41.
[42] Majumder, M.; Chopra, N.; Andrews, R.; Hinds, B. J. Enhanced Flow in Carbon Nanotubes. Nature 2005, 438, 43-44.
[43] Kowalczyk, S. W.; Grosberg, A. Y.; Rabin, Y.; Dekker, C. Modeling the Conductance and DNA Blockade of Solid-State Nanopores. Nanotechnology 2011, 22, 315101.
[44] Bearden, S.; Zhang, G. The Effects of the Electrical Double Layer on Giant Ionic Currents through Single-Walled Carbon Nanotubes. Nanotechnology 2013, 24, 125204.
[45] Bearden, S.; Zhang, G. Actively Controlled Ionic Current Gating In Nanopores. COMSOL Conf. 2013, 3-7.
[46] Gil, D.; Rodriguez, J.; Ward, B.; Vertegel, A.; Ivanov, V.; Reukov, V. Antioxidant Activity of SOD and Catalase Conjugated with Nanocrystalline Ceria. Bioengineering 2017, 4, 18.
[47] Hanwell, M. D.; Curtis, D. E.; Lonie, D. C.; Vandermeerschd, T.; Zurek, E.; Hutchison, G. R. Avogadro: An Advanced Semantic Chemical Editor, Visualization, and Analysis Platform. J. Cheminform. 2012, 4, 1-17.
[48] BROOKS, B. R.; III, C. L. B.; A. D. MACKERELL, J.; NILSSON, L.; PETRELLA, R. J.; ROUX, B.; WON, Y.; ARCHONTIS, G.; BARTELS, C.; BORESCH, S.; et al. CHARMM: The Biomolecular Simulation Program. J. Comput. Chem. 2009, 30, 2967-2970.
[49] MacKerell, A. D.; Bashford, D.; Bellott, M.; Dunbrack, R. L.; Evanseck, J. D.; Field, M. J.; Fischer, S.; Gao, J.; Guo, H.; Ha, S.; et al. All-Atom Empirical Potential for Molecular Modeling and Dynamics Studies of Proteins. J. Phys. Chem. B 1998, 102, 3586-3616.
[50] Heinz, H.; Vaia, R. A.; Farmer, B. L.; Naik, R. R. Accurate Simulation of Surfaces and Interfaces of Face-Centered Cubic Metals Using 12-6 and 9-6 Lennard-Jones Potentials. J. Phys. Chem. C 2008, 112, 17281-17290.
[51] Martyna, G. J.; Tuckerman, M. E.; Tobias, D. J.; Klein, M. L. Explicit Reversible Integrators for Extended Systems Dynamics. Mol. Phys. 1996, 87, 1117-1157.
[52] Nosé, S. A Molecular Dynamics Method for Simulations in the Canonical Ensemble. Mol. Phys. 1984, 52, 255-268
[53] Andersen, H. C. Rattle: A "velocity" Version of the Shake Algorithm for Molecular Dynamics Calculations. J. Comput. Phys. 1983, 52, 24-34
[54] Hückel, E.; Debye, P. The Theory of Electrolytes. I. Lowering of Freezing Point and Related Phenomena. Phys. Zeitschrift 1923, 24, 185-206.
[55] Debye, P. On Ions and Their Activity. Chem. Weekbl. 1923, 20, 562-568
[56] Akeson, M.; Branton, D.; Church, G.; Deamer, D. W. CHARACTERIZATION OF INDIVIDUAL POLYMER MOLECULES BASED ON MONOMER-INTERFACE INTERACTIONS.
[57] Church, G.; Deamer, D. W.; Branton, D.; Baldarelli, R.; Kasianowicz, J. J. CHARACTERIZATION OF INDIVIDUAL POLYMER MOLECULES BASED ON MONOMER-INTERFACE INTERACTIONS. U.S. Pat. No. 5,795,782, 1998.

[58] Baranchikov, A. E.; Polezhaeva, O. S.; Ivanov, V. K.; Tretyakov, Y. D. Lattice Expansion and Oxygen Non-Stoichiometry of Nanocrystalline Ceria. CrystEngComm 2010, 12, 3531.

[59] Timp, W.; Mirsaidov, U. M.; Wang, D.; Comer, J.; Aksimentiev, A.; Timp, G. Nanopore Sequencing: Electrical Measurements of the Code of Life. IEEE Trans. *Nanotechnol.* 2010, 9, 281-294.

[60] Postma, H. W. C. Rapid Sequencing of Individual DNA Molecules in Graphene Nanogaps. *Nano Lett.* 2010, 10, 420-425.

[61] Branton, D.; Deamer, D. W.; Marziali, A.; Bayley, H.; Benner, S. a; Butler, T.; Ventra, M. Di; Garaj, S.; Hibbs, A.; Jovanovich, S. B.; et al. The Potential and Challenges of Nanopore Sequencing. *Genome Res.* 2008, 26, 1146-1153.

[62] Maitra, R. D.; Kim, J.; Dunbar, W. B. Recent Advances in Nanopore Sequencing. Electrophoresis 2012, 33, 3418-3428.

[63] Eisenstein, M. Oxford Nanopore Announcement Sets Sequencing Sector Abuzz. Nat. Biotechnol. 2012, 30, 295-296.

[64] Wilson, J.; Sloman, L.; He, Z.; Aksimentiev, A. Graphene Nanopores for Protein Sequencing. Adv. Funct. Mater. 2016, 26, 4830-4838.

[65] Kolmogorov, M.; Kennedy, E.; Dong, Z.; Timp, G.; Pevzner, P. Single-Molecule Protein Identification by Sub-Nanopore Sensors. PLoS Comput. Biol. 2016, 13, 1-12.

[66] Di Ventra, M.; Taniguchi, M. Decoding DNA, RNA and Peptides with Quantum Tunnelling. Nat. Nanotechnol. 2016, 11, 117-126.

[67] Chang, H.; Kosari, F.; Andreadakis, G.; Alam, M. a.; Vasmatzis, G.; Bashir, R. DNA-Mediated Fluctuations in Ionic Current through Silicon Oxide Nanopore Channels. Nano Letters, 2004, 4, 1551-1556.

[68] Kowalczyk, S. W.; Grosberg, A. Y.; Rabin, Y.; Dekker, C. Modeling the Conductance and DNA Blockade of Solid-State Nanopores. Nanotechnology 2011, 22, 315101.

[69] Ohshiro, T.; Umezawa, Y. Complementary Base-Pair-Facilitated Electron Tunneling for Electrically Pinpointing Complementary Nucleobases. Proc. Natl. Acad. Sci. U.S.A 2006, 103, 10-14.

[70] Ivanov, A. P.; Instuli, E.; McGilvery, C. M.; Baldwin, G.; McComb, D. W.; Albrecht, T.; Edel, J. B. DNA Tunneling Detector Embedded in a Nanopore. Nano Lett. 2011, 11, 279-285.

[71] Pintilie, F.; Luchian, T. Transport and Kinetic Features of Gold-Functionalized Artificial Nanopores. Romania 16, 273-281.

[72] Bearden, S.; McClure, E.; Zhang, G. Detecting and Identifying Small Molecules in a Nanopore Flux Capacitor. Nanotechnology 2016, 27, 75503.

[73] Timp, W.; Comer, J.; Aksimentiev, A. DNA Base-Calling from a Nanopore Using a Viterbi Algorithm. Biophys. J. 2012, 102, L37-9.

[74] Shannon, C. E. A Mathematical Theory of Communication. Bell Syst. Tech. J. 1948, 27, 379-423.

[75] Schneider, G. F.; Kowalczyk, S. W.; Calado, V. E.; Pandraud, G.; Zandbergen, H. W.; Vandersypen, L. M. K.; Dekker, C. DNA Translocation through Graphene Nanopores. Nano Lett. 2010, 10, 3163-3167.

[76] Fan, R.; Karnik, R.; Yue, M.; Li, D.; Majumdar, A.; Yang, P. DNA Translocation in Inorganic Nanotubes. Nano Lett. 2005, 5, 1633-1637.

[77] Carlsen, A. T.; Zahid, O. K.; Ruzicka, J.; Taylor, E. W.; Hall, A. R. Interpreting the Conductance Blockades of DNA Translocations through Solid-State Nanopores. ACS Nano 2014, 8, 4754-4760.

[78] Bearden, S.; Simpanen, E.; Zhang, G. Active Current Gating in Electrically Biased Conical Nanopores. Nanotechnology 2015, 26, 185502.

[79] Heng, J. B.; Aksimentiev, A.; Ho, C.; Marks, P.; Grinkova, Y. V; Sligar, S.; Schulten, K.; Timp, G. Stretching DNA Using the Electric Field in a Synthetic Nanopore. Nano Lett. 2005, 5, 1883-1888.

[80] Clausen-Schaumann, H.; Rief, M.; Tolksdorf, C.; Gaub, H. E. Mechanical Stability of Single DNA Molecules. Biophys. J. 2000, 78, 1997-2007.

[81] Smith, S. B.; Cui, Y.; Bustamante, C. Overstretching B-DNA: The Elastic Response of Individual Double-Stranded and Single-Stranded DNA Molecules. Science 1996, 271, 795-799.

We claim:

1. An electrical double layer (EDL) nanopore device comprising:
   an insulating substrate defining a nanopore therethrough;
   a nanopore electrode exposed in a portion of the nanopore wherein the nanopore electrode defines a conductive ring surface exposed around an inner surface of the nanopore along its depth in a conductive ring;
   an electrolyte in contact with the nanopore electrode;
   a reference electrode in contact with the electrolyte; and
   a meter electrically coupled between the nanopore electrode and the reference electrode,
   wherein the meter is configured to measure a charging potential of an EDL capacitance, ionic current, analyte mobility, or combinations thereof and to correlate the measurements with one or more properties of an analyte and/or an identity of the analyte.

2. The EDL nanopore device of claim 1, wherein the conductive ring has a thickness in a range of about 0.1 to 10 nm.

3. The EDL nanopore device of claim 1, wherein the nanopore diameter is between about 0.1 nm and 1000 nm.

4. The EDL nanopore device of claim 1 wherein the analyte is selected from polymers, polynucleotides, peptides, small molecules, toxins, and viruses.

5. The EDL nanopore device of claim 1 wherein the analyte is a polynucleotide.

6. The EDL nanopore device of claim 1 wherein the conductive ring is axisymmetric.

7. The EDL nanopore device of claim 1 wherein the electrolyte is NaF, KCl, NaCl, LiF, or a mixture of NaF and KCl.

8. A plurality of EDL nanopore devices of claim 1.

9. The EDL nanopore device of claim 1, wherein the insulating substrate comprises a first insulating layer, and wherein the nanopore electrode comprises a conductive layer on the first insulating layer, and the EDL nanopore device further comprises:
   a second insulating layer on the conductive layer so that the conductive layer is between the first and second insulating layers, and wherein the nanopore extends through the first and second insulating layers and through the conductive layer so that portions of the conductive layer are exposed in the nanopore between the first and second insulating layers.

10. The EDL capacitive nanopore device of claim 9, wherein each of the first and second insulating layers comprises at least one insulating material selected from the group consisting of silicon dioxide, silicon nitride and polyxylylene polymers.

11. The EDL nanopore device of claim 9, wherein the conductive layer comprises at least one material selected from the group consisting of platinum, gold, titanium, copper, carbon, indium tin oxide and a conductive polymer.

12. A method of determining physical properties of an analyte comprising:
   inducing an analyte to translocate through a nanopore of the EDL nanopore device of claim 1;
   measuring the signals comprising double layer potential, ionic current, mobility signals, or a combination thereof;
   quantitatively determining the physical properties of size and charge of the analyte by correlating the measured signals to an analytical model.

13. The method of claim 12, wherein the analyte is provided in a mixture of analytes.

14. A method of detecting and identifying a plurality of analytes in a mixture comprising:
   i) inducing each of the plurality of analytes to translocate through the nanopore of the EDL nanopore device of claim 1;
   ii) measuring signals selected from the group consisting of double layer potential, ionic current, mobility signals, or combinations thereof of each analyte that it translocates the nanopore;
   iii) grouping the signals by a clustering algorithm executed by the meter; and
   iv) comparing signals of each analyte with grouped signals from a mixture of analytes.

* * * * *